(12) United States Patent
Moritz et al.

(10) Patent No.: US 12,188,932 B2
(45) Date of Patent: Jan. 7, 2025

(54) METHOD FOR HIGH THROUGHPUT PEPTIDE-MHC AFFINITY SCREENING FOR TCR LIGANDS

(71) Applicant: Immatics Biotechnologies GmbH, Tuebingen (DE)

(72) Inventors: Andreas Moritz, Tuebingen (DE); Dominik Maurer, Moessingen (DE); Sebastian Bunk, Tuebingen (DE); Claudia Wagner, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 342 days.

(21) Appl. No.: 16/569,691

(22) Filed: Sep. 13, 2019

(65) Prior Publication Data

US 2020/0088726 A1   Mar. 19, 2020

Related U.S. Application Data

(60) Provisional application No. 62/873,102, filed on Jul. 11, 2019, provisional application No. 62/731,337, filed on Sep. 14, 2018.

(30) Foreign Application Priority Data

Sep. 14, 2018   (DE) .......................... 102018122546.6

(51) Int. Cl.
| | | |
|---|---|---|
| *A61K 38/17* | (2006.01) | |
| *A61K 39/00* | (2006.01) | |
| *A61K 39/395* | (2006.01) | |
| *C07K 14/74* | (2006.01) | |
| *G01N 33/569* | (2006.01) | |
| *G01N 33/50* | (2006.01) | |

(52) U.S. Cl.
CPC ... *G01N 33/56977* (2013.01); *A61K 38/1774* (2013.01); *A61K 39/00* (2013.01); *A61K 39/39541* (2013.01); *C07K 14/70539* (2013.01); *A61K 2039/505* (2013.01); *A61K 2039/57* (2013.01); *G01N 2333/7051* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 10,538,573 B2 | 1/2020 | Maurer et al. | |
| 2009/0117153 A1 | 5/2009 | Hansen et al. | |
| 2014/0162293 A1* | 6/2014 | Springer .......... | C07K 14/70539 435/325 |

FOREIGN PATENT DOCUMENTS

| | | |
|---|---|---|
| WO | 2003/100432 A2 | 12/2003 |
| WO | 2005/076009 A2 | 8/2005 |
| WO | 2011/101681 A2 | 8/2011 |
| WO | 2011/128448 A1 | 10/2011 |
| WO | 2013/030620 A2 | 3/2013 |
| WO | 2017/098699 A1 | 6/2017 |
| WO | 2017/158103 A1 | 9/2017 |
| WO | 2017/174822 A1 | 10/2017 |
| WO | 2018/029350 A2 | 2/2018 |

OTHER PUBLICATIONS

HLA Nomenclature 2015 (Year: 2015).*
Wurfel et al (Geburshilfe Frauenheilkd, 2020 80(11): 1123-1133, 19 pages) (Year: 2020).*
Yuliasih et al (F1000Research, 2022, 11:1011: 1-13) (Year: 2022).*
Jordier et al (Frontiers in Immunol. 2020, vol. 10, article 2966, pp. 1-7) (Year: 2020).*
Ali-Khan et al (Current Protocols in Protein Science, 2002: 22.1.-22.1.19) (Year: 2002).*
Schumacher and Schrieber (Science, 2015, 384 (6230): 69-74) (Year: 2015).*
Liu et al (MHC Complex: Interaction with Peptides. IN: eLS. John Wiley & Sons, Ltd: Chichester, DOI: 10.1002/9780470015902.a0000922.pub2, 2011, pp. 1-12) (Year: 2011).*
Wieczorek et al (Front. Immunol. 2017, vol. 8, article 292: 1-16) (Year: 2017).*
Allen et al (J. Immunol. May 1, 2017, 198 (1_Supplement): 146.12, one page) (Year: 2017).*
HLA Nomenclature 2023, 2 pages (Year: 2023).*
Rammensee et al (MHC Ligands and Peptide Motifs, 1997, Landes Bioscience, Springer, Austin, TX, pp. 33-37) (Year: 1997).*
Zacharias et al., "Conformational Flexibility of the MHC Class I a1-a2 Domain in Peptide Bound and Free States: A Molecular Dynamics Simulation Study" Biophysical Journal (Oct. 2004) vol. 87: 2203-2214.
Mage et al., "The Peptide-Receptive Transition State of MHC Class I Molecules: Insight from Structure and Molecular Dynamics" Journal of Immunology (2012) vol. 189: 1391-1399.
Jaravine et al., "Assessment of cancer and virus antigens for cross-reactivity in human tissues" Bioinformatics (2017) vol. 33, No. 1: 104-111.
Hansen et al., "Recognition of open conformers of classical MHC by chaperones and monoclonal antibodies" Immunological Reviews (2005) 100-111.

(Continued)

*Primary Examiner* — Michael Szperka
*Assistant Examiner* — Marianne Dibrino
(74) *Attorney, Agent, or Firm* — McBee, Moore & Vanik IP, LLC

(57) ABSTRACT

The present invention relates to a method for high throughput screening for a TCR-binding peptide ligand/MHC molecule complex, comprising a stabilized peptide-MHC molecule and respective uses of said method. The present invention further relates to polypeptides comprising or consisting of stabilized MHC molecules or peptide binding fragments thereof, pharmaceutical compositions comprising said polypeptides, vaccines comprising said pharmaceutical composition and uses of said vaccine for the manufacturing of a medicament and/or in the prevention of cancer The present invention further relates to nucleic acids encoding said polypeptides and vectors comprising said nucleic acids.

11 Claims, 20 Drawing Sheets
(16 of 20 Drawing Sheet(s) Filed in Color)
Specification includes a Sequence Listing.

(56) References Cited

OTHER PUBLICATIONS

International Search Report for Application No. PCT/EP2019/074511 dated Sep. 13, 2019, 19 pages.
Moritz, Andreas, et al., "Rapid generation of peptide-MHC complexes with disulfide-stabilized empty HLA-A *02 molecules for high throughput screening approaches" Science Immunology, p. 1, 2018.
Fritsche, Jens, et al., "Translating Immunopeptidomics to Immunotherapy-Decision-Making for Patient and Personalized Target Selection," Protemics, 2018, vol. 18, No. 12: 1700284. pp. 1-10.
Hein, Zeynep, et al., "Distinct mechanisms survey the structural integrity of HLA-B* 27:05 intracellularly and at the surface," PLoS ONE, 2018, vol. 13, No. 8: e0200811. pp. 1-20.
Altman, John D., et al. "Phenotypic Analysis of Antigen-Specific T Lymphocytes" Science, vol. 274, No. 5284, pp. 94-96, Oct. 4, 1996.
Bakker, Arnold H., et al. "Conditional MHC class I ligands and peptide exchange technology for the human MHC gene products HLA-A1, -A3, -A11, and -B7" PNAS, vol. 105, No. 10, pp. 3825-3830, Mar. 11, 2008.
Bean, Gordon J., et al. Development of Ultra-High-Density Screening Tools for Microbial "Omics" PLOS One, vol. 9, Issue 1, paper e85177, Jan. 2014, pp. 1-8.
Chong, Chloe, et al. High-throughput and Sensitive Immunopeptidomics Platform Reveals Profound Interferon-γ-Mediated Remodeling of the Human Leukocyte Antigen (HLA) Ligandome* Molecular & Cellular Proteomics, vol. 17, No. 3, pp. 533-548, Mar. 1, 2018.
Cochran, Jennifer R., et al. "A diverse set of oligomeric class II MHC-peptide complexes for probing T-cell receptor interactions" Chemistry & Biology, vol. 7, pp. 683-696, Sep. 2000.
Hein, Zeynep, et al. "Peptide-independent stabilization of MHC class I molecules breaches cellular quality control" Journal of Cell Science, vol. 127, No. 13, pp. 2885-2897, Jul. 1, 2014.
Luimstra, Jolien J., et al. "A flexible MHC class I multimer loading system for large-scale detection of antigen- specific T cells" Journal of Experimental Medicine, vol. 215, No. 5, pp. 1493-1504, May 2018.
Newell, Evan W. "Higher Throughput Methods of Identifying T Cell Epitopes for Studying Outcomes of Altered Antigen Processing and Presentation" Frontiers in Immunology, vol. 4, Article 430, Dec. 2013, pp 1-4.
Shao, Wenguang, et al. "The SysteMHC Atlas Project" Nucleic Acids Research, vol. 46, Database issue Jan. 2018, pp. D1237-01247.

* cited by examiner

Figure 13A

| SEQ ID NO: | | | |
|---|---|---|---|
| 15 | HLA-L | GSHSLRYFSTAVSQPGRGEPRFIAVGYVDDTEFVRFDSDSVSPRMERRAPWVEQE------ | 55 |
| 13 | HLA-J | ----------APTP*GISAPPFP--------------GRAAGSPASLPWATWTTRSSCGST | 36 |
| 14 | HLA-K | ----------VPTP*GISAPPCP--------------GRVAGSPGTSQWATWTTRSSCGST | 36 |
| 12 | HLA-H | RSHSMRYFYTTMSRPGRGEPRFISVGYVDDTQFVRFDSDAASQRMEPRAPWMERE------ | 55 |
| 331 | H2Kb | GPHSLRYFVTAVSRPGLGEPRYMEVGYVDDTEFVRFDSDAENPRYEPRARWMEQE------ | 55 |
| 9 | HLA-E | GSHSLKYFHTSVSRPGRGEPRFISVGYVDDTQFVRFDNDAASPRMVPRAPWMEQE------ | 55 |
| 10 | HLA-F | GSHSLRYFSTAVSRPGRGEPRYIAVEYVDDTQFLRFDSDAAIPRMEPREPWVEQE------ | 55 |
| 11 | HLA-G | GSHSMRYFSAAVSRPGRGEPRFIAMGYVDDTQFVRFDSDSACPRMEPRAPWVEQE------ | 55 |
| 6 | HLA-A | GSHSMRYFFTSVSRPGRGEPRFIAVGYVDDTQFVRFDSDAASQKMEPRAPWIEQE------ | 55 |
| 7 | HLA-B | GSHSMRYFYTSVSRPGRGEPRFISVGYVDDTQFVRFDSDAASPREEPRAPWIEQE------ | 55 |
| 8 | HLA-C | CSHSMKYFFTSVSRPGRGEPRFISVGYVDDTQFVRFDSDAASPRGEPRAPWVEQE------ | 55 |

```
                       :  * . *                       . :         *  :.
```

| | | | |
|---|---|---|---|
| | HLA-L | -----------GLEYWDQETRN----------------------------AKGHAQIYRV | 76 |
| | HLA-J | VTP*V*G*RRGRGGWSRRGRSIGTYRHWAPRPRRLTE*TCGPCSATTTRARRGITSSRE | 92 |
| | HLA-K | ATRRLRGCSRSRRGWSRRDRSIGTGAHGTSGPRTD*QR*TCPCRAATTTRARPGLTPSR* | 93 |
| | HLA-H | -----------GPEYWDRNTQI----------------------------CKAQAQTERE | 76 |
| | H2Kb | -----------GPEYWERETQK----------------------------AKGNEQSFRV | 76 |
| | HLA-E | -----------GSEYWDRETRS----------------------------ARDTAQIFRV | 76 |
| | HLA-F | -----------GPQYWEWTTGY----------------------------AKANAQTDRV | 76 |
| | HLA-G | -----------GPEYWEEETRN----------------------------TKAHAQTDRM | 76 |
| | HLA-A | -----------GPEYWDQETRN----------------------------MKAHSQTDRA | 76 |
| | HLA-B | -----------GPEYWDRNTQI----------------------------YKAQAQTDRE | 76 |
| | HLA-C | -----------GPEYWDRETQK----------------------------YKRQAQTDRV | 76 |

```
                        .*.                                :    *
```

| | | | |
|---|---|---|---|
| | HLA-L | NLRTLLRYYNQSEAGSHTIQRKHGCDVGPTGASSAGMNSSPTMARITSP*TRTCTPGPP- | 134 |
| | HLA-J | CLAATWGPTGVSSAGMSSMPTT-------------------ARITSP*TRTCAPGPP- | 129 |
| | HLA-K | CMAATWGMKGASSAGMNSTPTM-------------------ARIT*PGTRTCAPGPR- | 130 |
| | HLA-H | NLRIALRYYNQSEGGSHTMQVM------------------------------YGCDVGPDG | 107 |
| | H2Kb | DLRTLLGYYNQSKGGSHTIQVI------------------------------SGCEVGSDG | 107 |
| | HLA-E | NLRTLRGYYNQSEAGSHTLQWM------------------------------HGCELGPDR | 107 |
| | HLA-F | ALRNLLRYYNQSEAGSHTLQGM------------------------------NGCDMGPDG | 107 |
| | HLA-G | NLQTLRGYYNQSEASSHTLQWM------------------------------IGCDLGSDG | 107 |
| | HLA-A | NLGTLRGYYNQSEDGSHTIQIM------------------------------YGCDVGPDG | 107 |
| | HLA-B | SLRNLRGYYNQSEAGSHTLQSM------------------------------YGCDVGPDG | 107 |
| | HLA-C | SLRNLRGYYNQSEAGSHTLQWM------------------------------CGCDLGPDG | 107 |

```
          :   .*. . :                                      *  *
```

| | | | |
|---|---|---|---|
| | HLA-L | -----------------------RTQRLRSPSTSGKRTNTQSRSGPT*GQV--HGVA---- | 165 |
| | HLA-J | -----------------------RIPRLRPSARMRRPMWLSKGEPTWRAPAWSGSAD---- | 164 |
| | HLA-K | -----------------------RTWRLRSPSARGRQKNLQSRSGPTWRARAWRGSQT--- | 165 |
| | HLA-H | RFLRGYEQHAYDSKKDYIALNEDLRSWTAADMAAQITKRKWEAARQAEQLRAYLEGEFVEW | 167 |
| | H2Kb | RLLRGYQQYAYDGCDYIALNEDLKTWTAADMAALITKHHWEQAGEAERLRAYLEGTCVEH | 167 |
| | HLA-E | RFLRGYEQFAYDGKDYLTLNEDLRSWTAVDTAAQISEQKSNDASEAEHQRAYLEDTCVEH | 167 |
| | HLA-F | RLLRGYHQHAYDGKDYISLNEDLRSWTAADTVAQITQRFYEAEEYAEEFRTYLEGECLEL | 167 |
| | HLA-G | RLLRGYEQYAYDGKDYLALNEDLRSWTAADTAAQISKRKCEAANVAEQRRAYLEGTCVEW | 167 |
| | HLA-A | RFLRGYRQDAYDGKDYIALNEDLRSWTAADMAAQITKRKWEAVHAAEQRRVYLEGRCVDG | 167 |
| | HLA-B | RLLRGHDQYAYDGKDYIALNEDLRSWTAADTAAQITQRKWEAAREAEQRRAYLEGECVEW | 167 |
| | HLA-C | RLLRGYDQYAYDGKDYIALNEDLRSWTAADTAAQITQRKWEAAREAEQRRAYLEGTCVEW | 167 |

```
                                  :              :  .                            .
```

| | | | |
|---|---|---|---|
| | HLA-L | POTPGGEREGDAAARGSPKGTCDPAPHL*P*GHPEVLGPGPLPCGDH----TDLAAGWGGP | 219 |
| | HLA-J | -----TWRTGRRRCSARTPPK-----THV--THP-PL*T*GITRSWVLGFYPAEITLTWQRD | 211 |
| | HLA-K | -----PGEREGDAAAHGPLPQ-----THM--IHHSVSDYKATLRCWALGFYPVEITLAWQQD | 215 |
| | HLA-H | LRRYLENGKETLQRADPPK-----THM--THHPISDHEATLRCWALGFYPAEITLTWQRD | 220 |
| | H2Kb | LRRYLKNGNATLLRTDSPK-----AHV--THHSRPEDKVTLRCWALGFYPADITLTWQLN | 220 |
| | HLA-E | LHRYLEKGKETLLHLEPPK-----THV--THHPISDHEATLRCWALGFYPAEITLTWQQD | 220 |
| | HLA-F | LRRYLENGKETLQRADPPK-----AHV--AHHPISDHEATLRCWALGFYPAEITLTWQRD | 220 |
| | HLA-G | LRRYLENGKEMLQRADPPK-----THV--THHPVFDYEATLRCWALGFYPAEIILTWQRD | 220 |
| | HLA-A | LRRYLENGKETLQRTDPPK-----THM--THHPISDHEATLRCWALGFYPAEITLTWQRD | 220 |
| | HLA-B | LRRYLENGKDKLERADPPK-----THV--THHPISDHEATLRCWALGFYPAEITLTWQRD | 220 |
| | HLA-C | LRRYLENGKETLQRAEHPK-----THV--THHPVSDHEATLRCWALGFYPAEITLTWQWD | 220 |

```
                            *:           .     .::  *
```

| SEQ ID NO: | | | |
|---|---|---|---|
| 15 | HLA-L | DPGHGACGDQACRGRNLPEV-------GGCSGAFRRGAEIHVP---------CAA*GAARAP | 264 |

Figure 13B

| SEQ ID NO: | | | |
|---|---|---|---|
| 13 | HLA-J | G--------EDQTQDMELVET------RPTGDGTFQKWAVVVVPSGEEQRYTCHVQHK-GLP | 258 |
| 14 | HLA-K | G--------EDQTRDMELLET------RPAGDGTFQKWAAVVVPSGEEQRYPCHVQHE-GLP | 262 |
| 12 | HLA-H | G--------EDQTHTRSSWRPGLQGMEPSRSGR--LWWCLLER-SRDTPAMCSMRVC-QSP | 269 |
| 331 | H2Kb | G--------EELIQDMELVET------RPAGDGTFQKWASVVVPLGKEQYYTCHVYHQ-GLP | 267 |
| 9 | HLA-E | G--------EGHTQDTELVET------RPAGDGTFQKWAAVVVPSGEEQRYTCHVQHE-GLP | 267 |
| 10 | HLA-F | G--------EEQTQDTELVET------RPAGDGTFQKWAAVVVPSGEEQRYTCHVQHE-GLP | 267 |
| 11 | HLA-G | G--------EDQTQDVELVET------RPAGDGTFQKWAAVVVPSGEEQRYTCHVQHE-GLP | 267 |
| 6 | HLA-A | G--------EDQTQDTELVET------RPAGDGTFQKWAAVVVPSGEEQRYTCHVQHE-GLP | 267 |
| 7 | HLA-B | G--------EDQTQDTELVET------RPAGDRTFQKWAAVVVPSGEEQRYTCHVQHE-GLP | 267 |
| 8 | HLA-C | G--------EDQTQDTELVET------RPAGDGTFQKWAAVMVPSGEEQRYTCHVQHE-GLP | 267 |
|  |  | .       : :  .  .           .         :            *       * |  |

| | | | |
|---|---|---|---|
| | HLA-L | HPEMGAVFSAHH---PHRG--HRCWPVSPWSCGHWSCGCCCDVEEEKLR*NK-EELCSGC | 317 |
| | HLA-J | KPLILRWEPSPQPTIPIVGIIAGLVLL--------------------------GAV---VTG- | 291 |
| | HLA-K | KPLTLRWEQSSQPTIPIVGIVAGLVLL--------------------------GAV---VTG- | 295 |
| | HLA-H | SP*DGSHLPS--PPSPSWASLLAWFYL*LWSLELWSLL*CGGRRAQIEKEGATLRLQAA- | 323 |
| | H2Kb | EPLTLRWEPPPS-TVSNMATVAVLVVL---------------------------GAA--IVTG- | 300 |
| | HLA-E | EPVTLRWKPASQPTIPIVGIIAGLVLL--------------------------GSV---VSG- | 300 |
| | HLA-F | QPLILRWEQSPQPTIPIVGIVAGLVVL--------------------------GAV---VTG- | 300 |
| | HLA-G | EPLMLRWKQSSLPTIPIMGIVAGLVVL--------------------------AAV---VTG- | 300 |
| | HLA-A | KPLTLRWEQSSQPTIPIVGIIAGLVLL--------------------------GAV---ITG- | 300 |
| | HLA-B | KPLTLRWEPSSQSTVPIVGIVAGLAVL--------------------------AVV---VIG- | 300 |
| | HLA-C | EPLTLRWEPSSQPTIPIVGIVAGLAVL--------------------------AVL--AVLG- | 301 |
|  |  |   *                        .       :                       . |  |

| | | | |
|---|---|---|---|
| | HLA-L | LQQLCSVL*CIS*YL*SLX-------------------------- | 333 |
| | HLA-J | --AVVTAVMW-RKKSSDRKGGSYSQAASSQSAQGSDVSLTACKV* | 332 |
| | HLA-K | --AVVSAVMC-RKKNSDRV--SYSEAASSDHAQGSDVSLTACKV* | 334 |
| | HLA-H | --TVPRALMCLSRRESVX--------------------------- | 339 |
| | H2Kb | --AVVAFVMKMRRRNTGGKGGDYALAPG---SQTSDLSLPDCKA- | 339 |
| | HLA-E | --AVVAAVIW-RKKSSGGKGGSYSKAEWSDSAQGSESHSL----- | 337 |
| | HLA-F | --AVVAAVMW-RKKSSDRNRGSYSQAAV----------------- | 325 |
| | HLA-G | --AAVAAVLW-RKKSSD--------------------------- | 314 |
| | HLA-A | --AVVAAVMW-RRKSSDRKGGSYTQAASSDSAQGSDVSLTACKV- | 341 |
| | HLA-B | --AVVAAVMC-RRKSSGGKGGSYSQAACSDSAQGSDVSLTA---- | 338 |
| | HLA-C | --AVVAVVMC-RRKSSGGKGGSCSQAASSNSAQGSDESLIACKA- | 342 |

SEQUENCE LISTING

```
<160> NUMBER OF SEQ ID NOS: 331

<210> SEQ ID NO 1
<211> LENGTH: 9
<212> TYPE: PRT
<213> ORGANISM: Homo sapiens

<400> SEQUENCE: 1

Ala Leu Tyr Asn Val Leu Ala Lys Val
1               5

<210> SEQ ID NO 2
<211> LENGTH: 6
<212> TYPE: PRT
<213> ORGANISM: Homo sapiens

<400> SEQUENCE: 2

Ala Pro Pro Val Ala Gly
1               5

<210> SEQ ID NO 3
<211> LENGTH: 9
<212> TYPE: PRT
<213> ORGANISM: Homo sapiens

<400> SEQUENCE: 3

Ser Leu Leu Met Trp Ile Thr Gln Cys
1               5

<210> SEQ ID NO 4
<211> LENGTH: 9
<212> TYPE: PRT
<213> ORGANISM: Homo sapiens

<400> SEQUENCE: 4

Ser Leu Leu Met Trp Ile Thr Gln Val
1               5

<210> SEQ ID NO 5
<211> LENGTH: 9
<212> TYPE: PRT
<213> ORGANISM: Homo sapiens

<400> SEQUENCE: 5

Ser Leu Tyr Asn Thr Val Ala Thr Leu
1               5

<210> SEQ ID NO 6
<211> LENGTH: 365
<212> TYPE: PRT
<213> ORGANISM: Homo sapiens

<400> SEQUENCE: 6

Met Ala Val Met Ala Pro Arg Thr Leu Leu Leu Leu Leu Ser Gly Ala
1               5                   10                  15
```

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
            115                 120                 125

Pro Asp Gly Arg Phe Leu Arg Gly Tyr Arg Gln Asp Ala Tyr Asp Gly
            130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Leu Ser Ser Gln Pro
290                 295                 300

Thr Ile Pro Ile Val Gly Ile Ile Ala Gly Leu Val Leu Leu Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 7
<211> LENGTH: 362
<212> TYPE: PRT
<213> ORGANISM: Homo sapiens

<400> SEQUENCE: 7

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe

```
            20                  25                  30
Tyr Thr Ser Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
 50                  55                  60

Ala Ser Pro Arg Glu Glu Pro Arg Ala Pro Trp Ile Glu Gln Glu Gly
 65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
            115                 120                 125

Pro Asp Gly Arg Leu Leu Arg Gly His Asp Gln Tyr Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
            195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Arg Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
            290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
            340                 345                 350

Ala Gln Gly Ser Asp Val Ser Leu Thr Ala
            355                 360

<210> SEQ ID NO 8
<211> LENGTH: 366
<212> TYPE: PRT
<213> ORGANISM: Homo sapiens

<400> SEQUENCE: 8

Met Arg Val Met Ala Pro Arg Thr Leu Ile Leu Leu Leu Ser Gly Ala
 1               5                  10                  15

Leu Ala Leu Thr Glu Thr Trp Ala Cys Ser His Ser Met Lys Tyr Phe
                20                  25                  30
```

-continued

Phe Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
 50                  55                  60

Ala Ser Pro Arg Gly Glu Pro Arg Ala Pro Trp Val Glu Gln Glu Gly
 65                  70                  75                  80

Pro Glu Tyr Trp Asp Arg Glu Thr Gln Lys Tyr Lys Arg Gln Ala Gln
                 85                  90                  95

Thr Asp Arg Val Ser Leu Arg Asn Leu Arg Gly Tyr Tyr Asn Gln Ser
             100                 105                 110

Glu Ala Gly Ser His Thr Leu Gln Trp Met Cys Gly Cys Asp Leu Gly
         115                 120                 125

Pro Asp Gly Arg Leu Leu Arg Gly Tyr Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Thr Cys Val Glu Trp Leu
            180                 185                 190

Arg Arg Tyr Leu Glu Asn Gly Lys Glu Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Trp Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Met
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Glu Pro Ser Ser Gln Pro
    290                 295                 300

Thr Ile Pro Ile Val Gly Ile Val Ala Gly Leu Ala Val Leu Ala Val
305                 310                 315                 320

Leu Ala Val Leu Gly Ala Val Val Ala Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Glu Ser Leu Ile Ala Cys Lys Ala
        355                 360                 365

<210> SEQ ID NO 9
<211> LENGTH: 358
<212> TYPE: PRT
<213> ORGANISM: Homo sapiens

<400> SEQUENCE: 9

Met Val Asp Gly Thr Leu Leu Leu Leu Leu Ser Glu Ala Leu Ala Leu
 1               5                  10                  15

Thr Gln Thr Trp Ala Gly Ser His Ser Leu Lys Tyr Phe His Thr Ser
             20                  25                  30

Val Ser Arg Pro Gly Arg Gly Glu Pro Arg Phe Ile Ser Val Gly Tyr
         35                  40                  45

Val Asp Asp Thr Gln Phe Val Arg Phe Asp Asn Asp Ala Ala Ser Pro
 50                  55                  60

Arg Met Val Pro Arg Ala Pro Trp Met Glu Gln Glu Gly Ser Glu Tyr
 65                  70                  75                  80

Trp Asp Arg Glu Thr Arg Ser Ala Arg Asp Thr Ala Gln Ile Phe Arg
                 85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Arg
            115                 120                 125

Arg Phe Leu Arg Gly Tyr Glu Gln Phe Ala Tyr Asp Gly Lys Asp Tyr
130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
            195                 200                 205

His Val Thr His His Pro Ile Ser Asp His Glu Ala Thr Leu Arg Cys
210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
            275                 280                 285

Glu Pro Val Thr Leu Arg Trp Lys Pro Ala Ser Gln Pro Thr Ile Pro
290                 295                 300

Ile Val Gly Ile Ile Ala Gly Leu Val Leu Leu Gly Ser Val Val Ser
305                 310                 315                 320

Gly Ala Val Val Ala Ala Val Ile Trp Arg Lys Lys Ser Ser Gly Gly
                325                 330                 335

Lys Gly Gly Ser Tyr Ser Lys Ala Glu Trp Ser Asp Ser Ala Gln Gly
            340                 345                 350

Ser Glu Ser His Ser Leu
            355

<210> SEQ ID NO 10
<211> LENGTH: 346
<212> TYPE: PRT
<213> ORGANISM: Homo sapiens

<400> SEQUENCE: 10

Met Ala Pro Arg Ser Leu Leu Leu Leu Leu Ser Gly Ala Leu Ala Leu
1                   5                   10                  15

Thr Asp Thr Trp Ala Gly Ser His Ser Leu Arg Tyr Phe Ser Thr Ala
                 20                  25                  30

Val Ser Arg Pro Gly Arg Gly Glu Pro Arg Tyr Ile Ala Val Glu Tyr
            35                  40                  45

Val Asp Asp Thr Gln Phe Leu Arg Phe Asp Ser Asp Ala Ala Ile Pro

```
                    50                  55                  60
Arg Met Glu Pro Arg Glu Pro Trp Val Glu Gln Glu Gly Pro Gln Tyr
 65                  70                  75                  80

Trp Glu Trp Thr Thr Gly Tyr Ala Lys Ala Asn Ala Gln Thr Asp Arg
                 85                  90                  95

Val Ala Leu Arg Asn Leu Leu Arg Arg Tyr Asn Gln Ser Glu Ala Gly
             100                 105                 110

Ser His Thr Leu Gln Gly Met Asn Gly Cys Asp Met Gly Pro Asp Gly
         115                 120                 125

Arg Leu Leu Arg Gly Tyr His Gln His Ala Tyr Asp Gly Lys Asp Tyr
     130                 135                 140

Ile Ser Leu Asn Glu Asp Leu Arg Ser Trp Thr Ala Ala Asp Thr Val
145                 150                 155                 160

Ala Gln Ile Thr Gln Arg Phe Tyr Glu Ala Glu Tyr Ala Glu Glu
                165                 170                 175

Phe Arg Thr Tyr Leu Glu Gly Glu Cys Leu Glu Leu Leu Arg Arg Tyr
             180                 185                 190

Leu Glu Asn Gly Lys Glu Thr Leu Gln Arg Ala Asp Pro Pro Lys Ala
         195                 200                 205

His Val Ala His His Pro Ile Ser Asp His Glu Ala Thr Leu Arg Cys
     210                 215                 220

Trp Ala Leu Gly Phe Tyr Pro Ala Glu Ile Thr Leu Thr Trp Gln Arg
225                 230                 235                 240

Asp Gly Glu Glu Gln Thr Gln Asp Thr Glu Leu Val Glu Thr Arg Pro
                245                 250                 255

Ala Gly Asp Gly Thr Phe Gln Lys Trp Ala Ala Val Val Val Pro Ser
             260                 265                 270

Gly Glu Glu Gln Arg Tyr Thr Cys His Val Gln His Glu Gly Leu Pro
         275                 280                 285

Gln Pro Leu Ile Leu Arg Trp Glu Gln Ser Pro Gln Pro Thr Ile Pro
     290                 295                 300

Ile Val Gly Ile Val Ala Gly Leu Val Val Leu Gly Ala Val Val Thr
305                 310                 315                 320

Gly Ala Val Val Ala Ala Val Met Trp Arg Lys Lys Ser Ser Asp Arg
                325                 330                 335

Asn Arg Gly Ser Tyr Ser Gln Ala Ala Val
             340                 345

<210> SEQ ID NO 11
<211> LENGTH: 338
<212> TYPE: PRT
<213> ORGANISM: Homo sapiens

<400> SEQUENCE: 11

Met Val Val Met Ala Pro Arg Thr Leu Phe Leu Leu Leu Ser Gly Ala
1               5                  10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
             35                  40                  45

Met Gly Tyr Val Asp Asp Thr Gln Phe Val Arg Phe Asp Ser Asp Ser
         50                  55                  60

Ala Cys Pro Arg Met Glu Pro Arg Ala Pro Trp Val Glu Gln Glu Gly
 65                  70                  75                  80
```

Pro Glu Tyr Trp Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
            130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
            210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
            275                 280                 285

Gly Leu Pro Glu Pro Leu Met Leu Arg Trp Lys Gln Ser Ser Leu Pro
            290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 12
<211> LENGTH: 363
<212> TYPE: PRT
<213> ORGANISM: Homo sapiens
<220> FEATURE:
<221> NAME/KEY: MISC_FEATURE
<222> LOCATION: (363)..(363)
<223> OTHER INFORMATION: Xaa = any amino acid

<400> SEQUENCE: 12

Met Val Leu Met Ala Pro Arg Thr Leu Leu Leu Leu Leu Ser Gly Ala
1               5                   10                  15

Leu Ala Leu Thr Gln Thr Trp Ala Arg Ser His Ser Met Arg Tyr Phe
                20                  25                  30

Tyr Thr Thr Met Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Gln Arg Met Glu Pro Arg Ala Pro Trp Met Glu Arg Glu Gly
65                  70                  75                  80

Pro Glu Tyr Trp Asp Arg Asn Thr Gln Ile Cys Lys Ala Gln Ala Gln
                85                  90                  95

Thr Glu Arg Glu Asn Leu Arg Ile Ala Leu Arg Tyr Asn Gln Ser
            100                 105                 110

Glu Gly Gly Ser His Thr Met Gln Val Met Tyr Gly Cys Asp Val Gly
            115                 120                 125

Pro Asp Gly Arg Phe Leu Arg Gly Tyr Glu Gln His Ala Tyr Asp Ser
            130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Ala Arg Gln
                    165                 170                 175

Ala Glu Gln Leu Arg Ala Tyr Leu Glu Gly Gly Phe Val Glu Trp Leu
            180                 185                 190

Arg Arg Tyr Leu Glu Asn Gly Lys Glu Thr Leu Gln Arg Ala Asp Pro
            195                 200                 205

Pro Lys Thr His Met Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr His Thr Arg Ser Ser Trp Arg
                    245                 250                 255

Pro Gly Leu Gln Gly Met Glu Pro Ser Arg Ser Gly Arg Leu Trp Trp
            260                 265                 270

Cys Leu Leu Glu Arg Ser Arg Asp Thr Pro Ala Met Cys Ser Met Arg
            275                 280                 285

Val Cys Gln Ser Pro Ser Pro Asp Gly Ser His Leu Pro Ser Pro Pro
            290                 295                 300

Ser Pro Ser Trp Ala Ser Leu Leu Ala Trp Phe Tyr Leu Leu Trp Ser
305                 310                 315                 320

Leu Glu Leu Trp Ser Leu Leu Cys Gly Gly Arg Arg Ala Gln Ile Glu
                    325                 330                 335

Lys Glu Gly Ala Thr Leu Arg Leu Gln Ala Ala Thr Val Pro Arg Ala
            340                 345                 350

Leu Met Cys Leu Ser Arg Arg Glu Ser Val Xaa
            355                 360

<210> SEQ ID NO 13
<211> LENGTH: 356
<212> TYPE: PRT
<213> ORGANISM: Homo sapiens

<400> SEQUENCE: 13

Met Gly Ser Trp Arg Pro Glu Pro Ser Ser Cys Cys Ser Arg Gly Pro
1               5                   10                  15

Trp Pro Trp Pro Arg Pro Gly Arg Ala Pro Thr Pro Gly Ile Ser Ala
            20                  25                  30

Pro Pro Phe Pro Gly Arg Ala Ala Gly Ser Pro Ala Ser Leu Pro Trp
            35                  40                  45

Ala Thr Trp Thr Thr Arg Ser Ser Cys Gly Ser Thr Val Thr Pro Val
        50                  55                  60

Gly Arg Arg Gly Arg Gly Gly Trp Ser Arg Gly Arg Ser Ile Gly
65                  70                  75                  80

Thr Tyr Arg His Trp Ala Pro Arg Pro Arg His Arg Leu Thr Glu Thr
                85                  90                  95

Cys Gly Pro Cys Ser Ala Thr Thr Thr Arg Ala Arg Arg Gly Ile Thr

```
            100                 105                 110
Ser Ser Arg Glu Cys Leu Ala Ala Thr Trp Gly Pro Thr Gly Val Ser
        115                 120                 125

Ser Ala Gly Met Ser Ser Met Pro Thr Thr Ala Arg Ile Thr Ser Pro
        130                 135                 140

Thr Arg Thr Cys Ala Pro Gly Pro Pro Arg Ile Pro Arg Leu Arg Leu
145                 150                 155                 160

Pro Ser Ala Ser Met Arg Arg Pro Met Trp Leu Ser Lys Gly Glu Pro
                165                 170                 175

Thr Trp Arg Ala Pro Ala Trp Ser Gly Ser Ala Asp Thr Trp Arg Thr
            180                 185                 190

Gly Arg Arg Arg Cys Ser Ala Arg Thr Pro Pro Lys Thr His Val Thr
        195                 200                 205

His Pro Pro Leu Thr Gly Ile Thr Arg Ser Trp Val Leu Gly Phe Tyr
        210                 215                 220

Pro Ala Glu Ile Thr Leu Thr Trp Gln Arg Asp Gly Glu Asp Gln Thr
225                 230                 235                 240

Gln Asp Met Glu Leu Val Glu Thr Arg Pro Thr Gly Asp Gly Thr Phe
                245                 250                 255

Gln Lys Trp Ala Val Val Val Pro Ser Gly Glu Glu Gln Arg Tyr
            260                 265                 270

Thr Cys His Val Gln His Lys Gly Leu Pro Lys Pro Leu Ile Leu Arg
        275                 280                 285

Trp Glu Pro Ser Pro Gln Pro Thr Ile Pro Ile Val Gly Ile Ile Ala
        290                 295                 300

Gly Leu Val Leu Leu Gly Ala Val Val Thr Gly Ala Val Val Thr Ala
305                 310                 315                 320

Val Met Trp Arg Lys Lys Ser Ser Asp Arg Lys Gly Gly Ser Tyr Ser
                325                 330                 335

Gln Ala Ala Ser Ser Gln Ser Ala Gln Gly Ser Asp Val Ser Leu Thr
            340                 345                 350

Ala Cys Lys Val
        355

<210> SEQ ID NO 14
<211> LENGTH: 357
<212> TYPE: PRT
<213> ORGANISM: Homo sapiens

<400> SEQUENCE: 14

Met Gly Ser Trp Arg Pro Glu Pro Ser Ser Cys Cys Ser Trp Gly Pro
1               5                   10                  15

Trp Pro Pro Arg Pro Gly Arg Val Pro Thr Pro Gly Ile Ser Ala Pro
                20                  25                  30

Pro Cys Pro Gly Arg Val Ala Gly Ser Pro Gly Thr Ser Gln Trp Ala
            35                  40                  45

Thr Trp Thr Thr Arg Ser Ser Cys Gly Ser Thr Ala Thr Arg Arg Leu
        50                  55                  60

Arg Gly Cys Ser Arg Ser Arg Arg Gly Trp Ser Arg Arg Asp Arg Ser
65                  70                  75                  80

Ile Gly Thr Gly Ala His Gly Thr Ser Gly Pro Arg Thr Asp Gln Glu
                85                  90                  95

Thr Cys Pro Cys Arg Ala Ala Thr Thr Arg Ala Arg Pro Gly Leu
            100                 105                 110
```

```
Thr Pro Ser Arg Cys Met Ala Ala Thr Trp Gly Trp Lys Gly Ala Ser
            115                 120                 125

Ser Ala Gly Met Asn Ser Thr Pro Thr Met Ala Arg Ile Thr Pro Gly
        130                 135                 140

Thr Arg Thr Cys Ala Pro Gly Pro Arg Thr Trp Arg Leu Arg Ser
145                 150                 155                 160

Pro Ser Ala Ser Gly Arg Gln Lys Asn Leu Gln Ser Arg Ser Gly Pro
                165                 170                 175

Thr Trp Arg Ala Arg Ala Trp Arg Gly Ser Gln Thr Pro Gly Glu Arg
            180                 185                 190

Glu Gly Asp Ala Ala His Gly Pro Leu Pro Gln Thr His Met Ile
195                 200                 205

His His Ser Val Ser Asp Tyr Lys Ala Thr Leu Arg Cys Trp Ala Leu
            210                 215                 220

Gly Phe Tyr Pro Val Glu Ile Thr Leu Ala Trp Gln Gln Asp Gly Glu
225                 230                 235                 240

Asp Gln Thr Arg Asp Met Glu Leu Leu Glu Thr Arg Pro Ala Gly Asp
                245                 250                 255

Gly Thr Phe Gln Lys Trp Ala Val Val Val Pro Ser Gly Glu Glu
            260                 265                 270

Gln Arg Tyr Pro Cys His Val Gln His Glu Gly Leu Pro Lys Pro Leu
            275                 280                 285

Thr Leu Arg Trp Glu Gln Ser Ser Gln Pro Thr Ile Pro Ile Val Gly
            290                 295                 300

Ile Val Ala Gly Leu Val Leu Leu Gly Ala Val Val Thr Gly Ala Val
305                 310                 315                 320

Val Ser Ala Val Met Cys Arg Lys Lys Asn Ser Asp Arg Val Ser Tyr
                325                 330                 335

Ser Glu Ala Ala Ser Ser Asp His Ala Gln Gly Ser Asp Val Ser Leu
            340                 345                 350

Thr Ala Cys Lys Val
            355
```

<210> SEQ ID NO 15
<211> LENGTH: 357
<212> TYPE: PRT
<213> ORGANISM: Homo sapiens
<220> FEATURE:
<221> NAME/KEY: MISC_FEATURE
<222> LOCATION: (357)..(357)
<223> OTHER INFORMATION: Xaa = any amino acid

<400> SEQUENCE: 15

```
Met Gly Val Met Ala Pro Arg Thr Leu Leu Leu Leu Leu Gly Ala
1               5                   10                  15

Leu Ala Leu Thr Glu Thr Trp Ala Gly Ser His Ser Leu Arg Tyr Phe
            20                  25                  30

Ser Thr Ala Val Ser Gln Pro Gly Arg Gly Glu Pro Arg Phe Ile Ala
        35                  40                  45

Val Gly Tyr Val Asp Asp Thr Glu Phe Val Arg Phe Asp Ser Asp Ser
    50                  55                  60

Val Ser Pro Arg Met Glu Arg Arg Ala Pro Trp Val Glu Gln Glu Gly
65                  70                  75                  80

Leu Glu Tyr Trp Asp Gln Glu Thr Arg Asn Ala Lys Gly His Ala Gln
                85                  90                  95

Ile Tyr Arg Val Asn Leu Arg Thr Leu Leu Arg Tyr Tyr Asn Gln Ser
```

```
                100             105             110
Glu Ala Gly Ser His Thr Ile Gln Arg Lys His Gly Cys Asp Val Gly
        115                 120                 125
Pro Thr Gly Ala Ser Ala Gly Met Asn Ser Ser Pro Thr Met Ala
    130                 135                 140
Arg Ile Thr Ser Pro Thr Arg Thr Cys Thr Pro Gly Pro Pro Arg Thr
145                 150                 155                 160
Gln Arg Leu Arg Ser Pro Ser Thr Ser Gly Lys Arg Thr Asn Thr Gln
            165                 170                 175
Ser Arg Ser Gly Pro Thr Gly Gln Val His Gly Val Ala Pro Gln Thr
        180                 185                 190
Pro Gly Glu Arg Glu Gly Asp Ala Ala Arg Gly Ser Pro Lys Gly
        195                 200                 205
Thr Cys Asp Pro Ala Pro His Leu Pro Gly His Pro Glu Val Leu Gly
        210                 215                 220
Pro Gly Pro Leu Pro Cys Gly Asp His Thr Asp Leu Ala Ala Gly Trp
225                 230                 235                 240
Gly Gly Pro Asp Pro Gly His Gly Ala Cys Gly Asp Gln Ala Cys Arg
            245                 250                 255
Gly Arg Asn Leu Pro Glu Val Gly Gly Cys Ser Gly Ala Phe Arg Arg
            260                 265                 270
Gly Ala Glu Ile His Val Pro Cys Ala Ala Gly Ala Arg Ala Pro
        275                 280                 285
His Pro Glu Met Gly Ala Val Phe Ser Ala His His Pro His Arg Gly
        290                 295                 300
His Arg Cys Trp Pro Val Ser Pro Trp Ser Cys Gly His Trp Ser Cys
305                 310                 315                 320
Gly Cys Cys Cys Asp Val Glu Glu Glu Lys Leu Arg Asn Lys Glu Glu
            325                 330                 335
Leu Cys Ser Gly Cys Leu Gln Gln Leu Cys Ser Val Leu Cys Ile Ser
            340                 345                 350
Tyr Leu Ser Leu Xaa
        355

<210> SEQ ID NO 16
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 16

Gly Leu Tyr Asn Thr Val Ala Thr Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 17

Pro Leu Tyr Asn Thr Val Ala Thr Leu
1               5

<210> SEQ ID NO 18
<211> LENGTH: 9
```

```
<212> TYPE: PRT
<213> ORGANISM: Artificial Sequence
<220> FEATURE:
<223> OTHER INFORMATION: Positional scanning library sequence

<400> SEQUENCE: 18

Ala Leu Tyr Asn Thr Val Ala Thr Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 19

Val Leu Tyr Asn Thr Val Ala Thr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 20

Leu Leu Tyr Asn Thr Val Ala Thr Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 21

Ile Leu Tyr Asn Thr Val Ala Thr Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 22

Met Leu Tyr Asn Thr Val Ala Thr Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 23

Phe Leu Tyr Asn Thr Val Ala Thr Leu
1               5

<210> SEQ ID NO 24
<211> LENGTH: 9
<212> TYPE: PRT
```

```
<213> ORGANISM: Artificial Sequence
<220> FEATURE:
<223> OTHER INFORMATION: Positional scanning library sequence

<400> SEQUENCE: 24

Tyr Leu Tyr Asn Thr Val Ala Thr Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 25

Trp Leu Tyr Asn Thr Val Ala Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 26

His Leu Tyr Asn Thr Val Ala Thr Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 27

Lys Leu Tyr Asn Thr Val Ala Thr Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 28

Arg Leu Tyr Asn Thr Val Ala Thr Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 29

Gln Leu Tyr Asn Thr Val Ala Thr Leu
1               5

<210> SEQ ID NO 30
<211> LENGTH: 9
<212> TYPE: PRT
<213> ORGANISM: Artificial Sequence
```

```
<220> FEATURE:
<223> OTHER INFORMATION: Positional scanning library sequence

<400> SEQUENCE: 30

Asn Leu Tyr Asn Thr Val Ala Thr Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 31

Glu Leu Tyr Asn Thr Val Ala Thr Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 32

Asp Leu Tyr Asn Thr Val Ala Thr Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 33

Thr Leu Tyr Asn Thr Val Ala Thr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 34

Ser Gly Tyr Asn Thr Val Ala Thr Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 35

Ser Pro Tyr Asn Thr Val Ala Thr Leu
1               5

<210> SEQ ID NO 36
<211> LENGTH: 9
<212> TYPE: PRT
<213> ORGANISM: Artificial Sequence
<220> FEATURE:
```

<223> OTHER INFORMATION: Positional scanning library sequence

<400> SEQUENCE: 36

Ser Ala Tyr Asn Thr Val Ala Thr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 37

Ser Val Tyr Asn Thr Val Ala Thr Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 38

Ser Ile Tyr Asn Thr Val Ala Thr Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 39

Ser Met Tyr Asn Thr Val Ala Thr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 40

Ser Phe Tyr Asn Thr Val Ala Thr Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 41

Ser Tyr Tyr Asn Thr Val Ala Thr Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Positional scanning library sequence

```
<400> SEQUENCE: 42

Ser Trp Tyr Asn Thr Val Ala Thr Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 43

Ser His Tyr Asn Thr Val Ala Thr Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 44

Ser Lys Tyr Asn Thr Val Ala Thr Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 45

Ser Arg Tyr Asn Thr Val Ala Thr Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 46

Ser Gln Tyr Asn Thr Val Ala Thr Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 47

Ser Asn Tyr Asn Thr Val Ala Thr Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Positional scanning library sequence
```

```
<400> SEQUENCE: 48

Ser Glu Tyr Asn Thr Val Ala Thr Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 49

Ser Asp Tyr Asn Thr Val Ala Thr Leu
1               5

<210> SEQ ID NO 50
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 50

Ser Ser Tyr Asn Thr Val Ala Thr Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 51

Ser Thr Tyr Asn Thr Val Ala Thr Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 52

Ser Leu Gly Asn Thr Val Ala Thr Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 53

Ser Leu Pro Asn Thr Val Ala Thr Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 54
```

Ser Leu Ala Asn Thr Val Ala Thr Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 55

Ser Leu Val Asn Thr Val Ala Thr Leu
1               5

<210> SEQ ID NO 56
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 56

Ser Leu Leu Asn Thr Val Ala Thr Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 57

Ser Leu Ile Asn Thr Val Ala Thr Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 58

Ser Leu Met Asn Thr Val Ala Thr Leu
1               5

<210> SEQ ID NO 59
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 59

Ser Leu Phe Asn Thr Val Ala Thr Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 60

```
Ser Leu Trp Asn Thr Val Ala Thr Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 61

Ser Leu His Asn Thr Val Ala Thr Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 62

Ser Leu Lys Asn Thr Val Ala Thr Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 63

Ser Leu Arg Asn Thr Val Ala Thr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 64

Ser Leu Gln Asn Thr Val Ala Thr Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 65

Ser Leu Asn Asn Thr Val Ala Thr Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 66

Ser Leu Glu Asn Thr Val Ala Thr Leu
```

1               5

<210> SEQ ID NO 67
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 67

Ser Leu Asp Asn Thr Val Ala Thr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 68

Ser Leu Ser Asn Thr Val Ala Thr Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 69

Ser Leu Thr Asn Thr Val Ala Thr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 70

Ser Leu Tyr Gly Thr Val Ala Thr Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 71

Ser Leu Tyr Pro Thr Val Ala Thr Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 72

Ser Leu Tyr Ala Thr Val Ala Thr Leu
1               5

```
<210> SEQ ID NO 73
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 73

Ser Leu Tyr Val Thr Val Ala Thr Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 74

Ser Leu Tyr Leu Thr Val Ala Thr Leu
1               5

<210> SEQ ID NO 75
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 75

Ser Leu Tyr Ile Thr Val Ala Thr Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 76

Ser Leu Tyr Met Thr Val Ala Thr Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 77

Ser Leu Tyr Phe Thr Val Ala Thr Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 78

Ser Leu Tyr Tyr Thr Val Ala Thr Leu
1               5
```

```
<210> SEQ ID NO 79
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 79

Ser Leu Tyr Trp Thr Val Ala Thr Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 80

Ser Leu Tyr His Thr Val Ala Thr Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 81

Ser Leu Tyr Lys Thr Val Ala Thr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 82

Ser Leu Tyr Arg Thr Val Ala Thr Leu
1               5

<210> SEQ ID NO 83
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 83

Ser Leu Tyr Gln Thr Val Ala Thr Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 84

Ser Leu Tyr Glu Thr Val Ala Thr Leu
1               5
```

-continued

```
<210> SEQ ID NO 85
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 85

Ser Leu Tyr Asp Thr Val Ala Thr Leu
1               5

<210> SEQ ID NO 86
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 86

Ser Leu Tyr Ser Thr Val Ala Thr Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 87

Ser Leu Tyr Thr Thr Val Ala Thr Leu
1               5

<210> SEQ ID NO 88
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 88

Ser Leu Tyr Asn Gly Val Ala Thr Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 89

Ser Leu Tyr Asn Pro Val Ala Thr Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 90

Ser Leu Tyr Asn Ala Val Ala Thr Leu
1               5

<210> SEQ ID NO 91
```

```
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 91

Ser Leu Tyr Asn Val Val Ala Thr Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 92

Ser Leu Tyr Asn Leu Val Ala Thr Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 93

Ser Leu Tyr Asn Ile Val Ala Thr Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 94

Ser Leu Tyr Asn Met Val Ala Thr Leu
1               5

<210> SEQ ID NO 95
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 95

Ser Leu Tyr Asn Phe Val Ala Thr Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 96

Ser Leu Tyr Asn Tyr Val Ala Thr Leu
1               5

<210> SEQ ID NO 97
<211> LENGTH: 9
```

```
<212> TYPE: PRT
<213> ORGANISM: Artificial Sequence
<220> FEATURE:
<223> OTHER INFORMATION: Positional scanning library sequence

<400> SEQUENCE: 97

Ser Leu Tyr Asn Trp Val Ala Thr Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 98

Ser Leu Tyr Asn His Val Ala Thr Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 99

Ser Leu Tyr Asn Lys Val Ala Thr Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 100

Ser Leu Tyr Asn Arg Val Ala Thr Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 101

Ser Leu Tyr Asn Gln Val Ala Thr Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 102

Ser Leu Tyr Asn Asn Val Ala Thr Leu
1               5

<210> SEQ ID NO 103
<211> LENGTH: 9
<212> TYPE: PRT
```

-continued

```
<213> ORGANISM: Artificial Sequence
<220> FEATURE:
<223> OTHER INFORMATION: Positional scanning library sequence

<400> SEQUENCE: 103

Ser Leu Tyr Asn Glu Val Ala Thr Leu
1               5

<210> SEQ ID NO 104
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 104

Ser Leu Tyr Asn Asp Val Ala Thr Leu
1               5

<210> SEQ ID NO 105
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 105

Ser Leu Tyr Asn Ser Val Ala Thr Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 106

Ser Leu Tyr Asn Thr Gly Ala Thr Leu
1               5

<210> SEQ ID NO 107
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 107

Ser Leu Tyr Asn Thr Pro Ala Thr Leu
1               5

<210> SEQ ID NO 108
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 108

Ser Leu Tyr Asn Thr Ala Ala Thr Leu
1               5

<210> SEQ ID NO 109
<211> LENGTH: 9
<212> TYPE: PRT
<213> ORGANISM: Artificial Sequence
```

```
<220> FEATURE:
<223> OTHER INFORMATION: Positional scanning library sequence

<400> SEQUENCE: 109

Ser Leu Tyr Asn Thr Leu Ala Thr Leu
1               5

<210> SEQ ID NO 110
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 110

Ser Leu Tyr Asn Thr Ile Ala Thr Leu
1               5

<210> SEQ ID NO 111
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 111

Ser Leu Tyr Asn Thr Met Ala Thr Leu
1               5

<210> SEQ ID NO 112
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 112

Ser Leu Tyr Asn Thr Phe Ala Thr Leu
1               5

<210> SEQ ID NO 113
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 113

Ser Leu Tyr Asn Thr Tyr Ala Thr Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 114

Ser Leu Tyr Asn Thr Trp Ala Thr Leu
1               5

<210> SEQ ID NO 115
<211> LENGTH: 9
<212> TYPE: PRT
<213> ORGANISM: Artificial Sequence
<220> FEATURE:
```

<223> OTHER INFORMATION: Positional scanning library sequence

<400> SEQUENCE: 115

Ser Leu Tyr Asn Thr His Ala Thr Leu
1               5

<210> SEQ ID NO 116
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 116

Ser Leu Tyr Asn Thr Lys Ala Thr Leu
1               5

<210> SEQ ID NO 117
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 117

Ser Leu Tyr Asn Thr Arg Ala Thr Leu
1               5

<210> SEQ ID NO 118
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 118

Ser Leu Tyr Asn Thr Gln Ala Thr Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 119

Ser Leu Tyr Asn Thr Asn Ala Thr Leu
1               5

<210> SEQ ID NO 120
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 120

Ser Leu Tyr Asn Thr Glu Ala Thr Leu
1               5

<210> SEQ ID NO 121
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 121

Ser Leu Tyr Asn Thr Asp Ala Thr Leu
1               5

<210> SEQ ID NO 122
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 122

Ser Leu Tyr Asn Thr Ser Ala Thr Leu
1               5

<210> SEQ ID NO 123
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 123

Ser Leu Tyr Asn Thr Thr Ala Thr Leu
1               5

<210> SEQ ID NO 124
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 124

Ser Leu Tyr Asn Thr Val Gly Thr Leu
1               5

<210> SEQ ID NO 125
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 125

Ser Leu Tyr Asn Thr Val Pro Thr Leu
1               5

<210> SEQ ID NO 126
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 126

Ser Leu Tyr Asn Thr Val Val Thr Leu
1               5

<210> SEQ ID NO 127
<211> LENGTH: 9
<212> TYPE: PRT
<213> ORGANISM: Artificial Sequence
<220> FEATURE:
<223> OTHER INFORMATION: Positional scanning library sequence

```
<400> SEQUENCE: 127

Ser Leu Tyr Asn Thr Val Leu Thr Leu
1               5

<210> SEQ ID NO 128
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 128

Ser Leu Tyr Asn Thr Val Ile Thr Leu
1               5

<210> SEQ ID NO 129
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 129

Ser Leu Tyr Asn Thr Val Met Thr Leu
1               5

<210> SEQ ID NO 130
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 130

Ser Leu Tyr Asn Thr Val Phe Thr Leu
1               5

<210> SEQ ID NO 131
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 131

Ser Leu Tyr Asn Thr Val Tyr Thr Leu
1               5

<210> SEQ ID NO 132
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 132

Ser Leu Tyr Asn Thr Val Trp Thr Leu
1               5

<210> SEQ ID NO 133
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 133
```

```
Ser Leu Tyr Asn Thr Val His Thr Leu
1               5

<210> SEQ ID NO 134
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 134

Ser Leu Tyr Asn Thr Val Lys Thr Leu
1               5

<210> SEQ ID NO 135
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 135

Ser Leu Tyr Asn Thr Val Arg Thr Leu
1               5

<210> SEQ ID NO 136
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 136

Ser Leu Tyr Asn Thr Val Gln Thr Leu
1               5

<210> SEQ ID NO 137
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 137

Ser Leu Tyr Asn Thr Val Asn Thr Leu
1               5

<210> SEQ ID NO 138
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 138

Ser Leu Tyr Asn Thr Val Glu Thr Leu
1               5

<210> SEQ ID NO 139
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 139
```

```
Ser Leu Tyr Asn Thr Val Asp Thr Leu
1               5

<210> SEQ ID NO 140
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 140

Ser Leu Tyr Asn Thr Val Ser Thr Leu
1               5

<210> SEQ ID NO 141
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 141

Ser Leu Tyr Asn Thr Val Thr Thr Leu
1               5

<210> SEQ ID NO 142
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 142

Ser Leu Tyr Asn Thr Val Ala Gly Leu
1               5

<210> SEQ ID NO 143
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 143

Ser Leu Tyr Asn Thr Val Ala Pro Leu
1               5

<210> SEQ ID NO 144
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 144

Ser Leu Tyr Asn Thr Val Ala Ala Leu
1               5

<210> SEQ ID NO 145
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 145

Ser Leu Tyr Asn Thr Val Ala Val Leu
```

-continued 1               5

<210> SEQ ID NO 146
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 146

Ser Leu Tyr Asn Thr Val Ala Leu Leu
1               5

<210> SEQ ID NO 147
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 147

Ser Leu Tyr Asn Thr Val Ala Ile Leu
1               5

<210> SEQ ID NO 148
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 148

Ser Leu Tyr Asn Thr Val Ala Met Leu
1               5

<210> SEQ ID NO 149
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 149

Ser Leu Tyr Asn Thr Val Ala Phe Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 150

Ser Leu Tyr Asn Thr Val Ala Tyr Leu
1               5

<210> SEQ ID NO 151
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 151

Ser Leu Tyr Asn Thr Val Ala Trp Leu
1               5

<210> SEQ ID NO 152
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 152

Ser Leu Tyr Asn Thr Val Ala His Leu
1               5

<210> SEQ ID NO 153
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 153

Ser Leu Tyr Asn Thr Val Ala Lys Leu
1               5

<210> SEQ ID NO 154
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 154

Ser Leu Tyr Asn Thr Val Ala Arg Leu
1               5

<210> SEQ ID NO 155
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 155

Ser Leu Tyr Asn Thr Val Ala Gln Leu
1               5

<210> SEQ ID NO 156
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 156

Ser Leu Tyr Asn Thr Val Ala Asn Leu
1               5

<210> SEQ ID NO 157
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 157

Ser Leu Tyr Asn Thr Val Ala Glu Leu
1               5

```
<210> SEQ ID NO 158
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 158

Ser Leu Tyr Asn Thr Val Ala Asp Leu
1               5

<210> SEQ ID NO 159
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 159

Ser Leu Tyr Asn Thr Val Ala Ser Leu
1               5

<210> SEQ ID NO 160
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 160

Ser Leu Tyr Asn Thr Val Ala Thr Gly
1               5

<210> SEQ ID NO 161
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 161

Ser Leu Tyr Asn Thr Val Ala Thr Pro
1               5

<210> SEQ ID NO 162
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 162

Ser Leu Tyr Asn Thr Val Ala Thr Ala
1               5

<210> SEQ ID NO 163
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 163

Ser Leu Tyr Asn Thr Val Ala Thr Val
1               5
```

```
<210> SEQ ID NO 164
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 164

Ser Leu Tyr Asn Thr Val Ala Thr Ile
1               5

<210> SEQ ID NO 165
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 165

Ser Leu Tyr Asn Thr Val Ala Thr Met
1               5

<210> SEQ ID NO 166
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 166

Ser Leu Tyr Asn Thr Val Ala Thr Phe
1               5

<210> SEQ ID NO 167
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 167

Ser Leu Tyr Asn Thr Val Ala Thr Tyr
1               5

<210> SEQ ID NO 168
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 168

Ser Leu Tyr Asn Thr Val Ala Thr Trp
1               5

<210> SEQ ID NO 169
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 169

Ser Leu Tyr Asn Thr Val Ala Thr His
1               5

<210> SEQ ID NO 170
```

```
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 170

Ser Leu Tyr Asn Thr Val Ala Thr Lys
1               5

<210> SEQ ID NO 171
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 171

Ser Leu Tyr Asn Thr Val Ala Thr Arg
1               5

<210> SEQ ID NO 172
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 172

Ser Leu Tyr Asn Thr Val Ala Thr Gln
1               5

<210> SEQ ID NO 173
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 173

Ser Leu Tyr Asn Thr Val Ala Thr Asn
1               5

<210> SEQ ID NO 174
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 174

Ser Leu Tyr Asn Thr Val Ala Thr Glu
1               5

<210> SEQ ID NO 175
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 175

Ser Leu Tyr Asn Thr Val Ala Thr Asp
1               5

<210> SEQ ID NO 176
<211> LENGTH: 9
```

```
<212> TYPE: PRT
<213> ORGANISM: Artificial Sequence
<220> FEATURE:
<223> OTHER INFORMATION: Positional scanning library sequence

<400> SEQUENCE: 176

Ser Leu Tyr Asn Thr Val Ala Thr Ser
1               5

<210> SEQ ID NO 177
<211> LENGTH: 9
<212> TYPE: PRT
<213> ORGANISM: Artificial Sequence
<220> FEATURE:
<223> OTHER INFORMATION: Positional scanning library sequence

<400> SEQUENCE: 177

Ser Leu Tyr Asn Thr Val Ala Thr Thr
1               5

<210> SEQ ID NO 178
<211> LENGTH: 9
<212> TYPE: PRT
<213> ORGANISM: Homo sapiens

<400> SEQUENCE: 178

Arg Val Tyr Asn Thr Val Pro Leu Val
1               5

<210> SEQ ID NO 179
<211> LENGTH: 9
<212> TYPE: PRT
<213> ORGANISM: Homo sapiens

<400> SEQUENCE: 179

Arg Met Tyr Asn Leu Val Ser Arg Ile
1               5

<210> SEQ ID NO 180
<211> LENGTH: 9
<212> TYPE: PRT
<213> ORGANISM: Homo sapiens

<400> SEQUENCE: 180

Ser Leu Tyr Asn Met Val Pro Ser Ile
1               5

<210> SEQ ID NO 181
<211> LENGTH: 9
<212> TYPE: PRT
<213> ORGANISM: Homo sapiens

<400> SEQUENCE: 181

Thr Val Tyr Asn Met Val Pro Ser Ile
1               5

<210> SEQ ID NO 182
<211> LENGTH: 9
<212> TYPE: PRT
<213> ORGANISM: Homo sapiens

<400> SEQUENCE: 182

Ala Leu Tyr Asn Val Ile Ala Met Ala
1               5
```

```
<210> SEQ ID NO 183
<211> LENGTH: 9
<212> TYPE: PRT
<213> ORGANISM: Homo sapiens

<400> SEQUENCE: 183

Ala Ile Tyr Asn Leu Leu Pro Asp Ile
1               5

<210> SEQ ID NO 184
<211> LENGTH: 9
<212> TYPE: PRT
<213> ORGANISM: Homo sapiens

<400> SEQUENCE: 184

Ser Thr Tyr Asn Leu Val Ser Thr Ser
1               5

<210> SEQ ID NO 185
<211> LENGTH: 9
<212> TYPE: PRT
<213> ORGANISM: Homo sapiens

<400> SEQUENCE: 185

Ser Val Tyr Asn Met Val Pro Ser Ile
1               5

<210> SEQ ID NO 186
<211> LENGTH: 9
<212> TYPE: PRT
<213> ORGANISM: Homo sapiens

<400> SEQUENCE: 186

Arg Thr Tyr Asn Val Leu Ala Ile Leu
1               5

<210> SEQ ID NO 187
<211> LENGTH: 9
<212> TYPE: PRT
<213> ORGANISM: Homo sapiens

<400> SEQUENCE: 187

Ser Val Tyr Asn Leu Val Ser Ile Ala
1               5

<210> SEQ ID NO 188
<211> LENGTH: 9
<212> TYPE: PRT
<213> ORGANISM: Homo sapiens

<400> SEQUENCE: 188

Arg Ala Tyr Asn Leu Ile Gly Thr Val
1               5

<210> SEQ ID NO 189
<211> LENGTH: 9
<212> TYPE: PRT
<213> ORGANISM: Homo sapiens

<400> SEQUENCE: 189

Ala Leu Phe Asn Leu Ile Pro Val Gly
1               5

<210> SEQ ID NO 190
<211> LENGTH: 9
```

```
<212> TYPE: PRT
<213> ORGANISM: Homo sapiens

<400> SEQUENCE: 190

Arg Ile Tyr Asn Val Ile Gly Thr Leu
1               5

<210> SEQ ID NO 191
<211> LENGTH: 9
<212> TYPE: PRT
<213> ORGANISM: Homo sapiens

<400> SEQUENCE: 191

Arg Ile Tyr Asn Val Val Gly Thr Ile
1               5

<210> SEQ ID NO 192
<211> LENGTH: 9
<212> TYPE: PRT
<213> ORGANISM: Homo sapiens

<400> SEQUENCE: 192

Thr Leu Phe Asn Leu Val Pro Asn Ser
1               5

<210> SEQ ID NO 193
<211> LENGTH: 9
<212> TYPE: PRT
<213> ORGANISM: Homo sapiens

<400> SEQUENCE: 193

Ser Leu Phe Asn Val Ile Ser Ile Leu
1               5

<210> SEQ ID NO 194
<211> LENGTH: 9
<212> TYPE: PRT
<213> ORGANISM: Homo sapiens

<400> SEQUENCE: 194

Ser Thr Phe Asn Leu Val Ala Ile Ser
1               5

<210> SEQ ID NO 195
<211> LENGTH: 9
<212> TYPE: PRT
<213> ORGANISM: Homo sapiens

<400> SEQUENCE: 195

Thr Leu Phe Asn Leu Ile Pro Val Gly
1               5

<210> SEQ ID NO 196
<211> LENGTH: 9
<212> TYPE: PRT
<213> ORGANISM: Homo sapiens

<400> SEQUENCE: 196

Thr Ile Phe Asn Leu Ile Pro Asn Ser
1               5

<210> SEQ ID NO 197
<211> LENGTH: 9
<212> TYPE: PRT
<213> ORGANISM: Homo sapiens
```

<400> SEQUENCE: 197

Ala Leu Tyr Asn Val Leu Ala Lys Val
1               5

<210> SEQ ID NO 198
<211> LENGTH: 9
<212> TYPE: PRT
<213> ORGANISM: Homo sapiens

<400> SEQUENCE: 198

Ala Val Phe Asn Leu Leu Pro His Thr
1               5

<210> SEQ ID NO 199
<211> LENGTH: 9
<212> TYPE: PRT
<213> ORGANISM: Homo sapiens

<400> SEQUENCE: 199

Arg Met Tyr Asn Leu Leu Gly His Met
1               5

<210> SEQ ID NO 200
<211> LENGTH: 9
<212> TYPE: PRT
<213> ORGANISM: Homo sapiens

<400> SEQUENCE: 200

Ser Thr Trp Asn Thr Pro Pro Asn Met
1               5

<210> SEQ ID NO 201
<211> LENGTH: 9
<212> TYPE: PRT
<213> ORGANISM: Homo sapiens

<400> SEQUENCE: 201

Asn Ile Tyr Asn Leu Ile Ala Ile Ile
1               5

<210> SEQ ID NO 202
<211> LENGTH: 9
<212> TYPE: PRT
<213> ORGANISM: Homo sapiens

<400> SEQUENCE: 202

Arg Ile Tyr Asn Leu Pro Pro Glu Leu
1               5

<210> SEQ ID NO 203
<211> LENGTH: 9
<212> TYPE: PRT
<213> ORGANISM: Homo sapiens

<400> SEQUENCE: 203

Thr Thr Phe Asn Leu Pro Ser Ala Ala
1               5

<210> SEQ ID NO 204
<211> LENGTH: 9
<212> TYPE: PRT
<213> ORGANISM: Homo sapiens

<400> SEQUENCE: 204

Met Phe Phe Asn Val Ile Ala Ile Val
1               5

<210> SEQ ID NO 205
<211> LENGTH: 9
<212> TYPE: PRT
<213> ORGANISM: Homo sapiens

<400> SEQUENCE: 205

Ser Leu Trp Asn Thr Val Ser Gly Ile
1               5

<210> SEQ ID NO 206
<211> LENGTH: 9
<212> TYPE: PRT
<213> ORGANISM: Homo sapiens

<400> SEQUENCE: 206

Met Leu Trp Asn Leu Leu Ala Leu Arg
1               5

<210> SEQ ID NO 207
<211> LENGTH: 9
<212> TYPE: PRT
<213> ORGANISM: Homo sapiens

<400> SEQUENCE: 207

Val Phe Trp Asn Leu Leu Pro Thr Val
1               5

<210> SEQ ID NO 208
<211> LENGTH: 9
<212> TYPE: PRT
<213> ORGANISM: Homo sapiens

<400> SEQUENCE: 208

Ser Thr Phe Asn Thr Thr Ser Asn Gly
1               5

<210> SEQ ID NO 209
<211> LENGTH: 9
<212> TYPE: PRT
<213> ORGANISM: Homo sapiens

<400> SEQUENCE: 209

Gly Phe Phe Asn Leu Leu Ser His Val
1               5

<210> SEQ ID NO 210
<211> LENGTH: 9
<212> TYPE: PRT
<213> ORGANISM: Homo sapiens

<400> SEQUENCE: 210

Leu Leu Tyr Asn Val Pro Ala Val Ala
1               5

<210> SEQ ID NO 211
<211> LENGTH: 9
<212> TYPE: PRT
<213> ORGANISM: Homo sapiens

<400> SEQUENCE: 211

Ala Leu Phe Asn Thr Ile Ser Gln Gly

```
1               5
```

<210> SEQ ID NO 212
<211> LENGTH: 9
<212> TYPE: PRT
<213> ORGANISM: Homo sapiens

<400> SEQUENCE: 212

```
Thr Thr Phe Asn Thr Leu Ala Gly Ser
1               5
```

<210> SEQ ID NO 213
<211> LENGTH: 9
<212> TYPE: PRT
<213> ORGANISM: Homo sapiens

<400> SEQUENCE: 213

```
Ser Leu Trp Asn Leu Leu Gly Asn Ala
1               5
```

<210> SEQ ID NO 214
<211> LENGTH: 9
<212> TYPE: PRT
<213> ORGANISM: Homo sapiens

<400> SEQUENCE: 214

```
Ser Leu Tyr Asn Leu Leu Asn Leu Thr
1               5
```

<210> SEQ ID NO 215
<211> LENGTH: 9
<212> TYPE: PRT
<213> ORGANISM: Homo sapiens

<400> SEQUENCE: 215

```
Gly Val Trp Asn Leu Leu Ser Ile Val
1               5
```

<210> SEQ ID NO 216
<211> LENGTH: 9
<212> TYPE: PRT
<213> ORGANISM: Homo sapiens

<400> SEQUENCE: 216

```
Ala Leu Phe Asn Val Val Asn Ser Ile
1               5
```

<210> SEQ ID NO 217
<211> LENGTH: 9
<212> TYPE: PRT
<213> ORGANISM: Homo sapiens

<400> SEQUENCE: 217

```
Val Ile Tyr Asn Leu Leu Gly Leu Ala
1               5
```

<210> SEQ ID NO 218
<211> LENGTH: 9
<212> TYPE: PRT
<213> ORGANISM: Homo sapiens

<400> SEQUENCE: 218

```
Ser Ile Phe Asn Ile Val Ala Ile Ala
1               5
```

<210> SEQ ID NO 219
<211> LENGTH: 9
<212> TYPE: PRT
<213> ORGANISM: Homo sapiens

<400> SEQUENCE: 219

Thr Val Tyr Asn Thr Val Ser Glu Gly
1               5

<210> SEQ ID NO 220
<211> LENGTH: 9
<212> TYPE: PRT
<213> ORGANISM: Homo sapiens

<400> SEQUENCE: 220

Asp Leu Trp Asn Thr Leu Ser Ser Leu
1               5

<210> SEQ ID NO 221
<211> LENGTH: 9
<212> TYPE: PRT
<213> ORGANISM: Homo sapiens

<400> SEQUENCE: 221

Ile Phe Phe Asn Leu Leu Ala Val Leu
1               5

<210> SEQ ID NO 222
<211> LENGTH: 9
<212> TYPE: PRT
<213> ORGANISM: Homo sapiens

<400> SEQUENCE: 222

Asp Leu Phe Asn Leu Leu Pro Asp Val
1               5

<210> SEQ ID NO 223
<211> LENGTH: 9
<212> TYPE: PRT
<213> ORGANISM: Homo sapiens

<400> SEQUENCE: 223

Leu Ser Trp Asn Val Val Pro Asn Ala
1               5

<210> SEQ ID NO 224
<211> LENGTH: 9
<212> TYPE: PRT
<213> ORGANISM: Homo sapiens

<400> SEQUENCE: 224

Met Leu Trp Asn Leu Leu Ala Leu His
1               5

<210> SEQ ID NO 225
<211> LENGTH: 9
<212> TYPE: PRT
<213> ORGANISM: Homo sapiens

<400> SEQUENCE: 225

Thr Ile Phe Asn Thr Val Asn Thr Ser
1               5

<210> SEQ ID NO 226

```
<211> LENGTH: 9
<212> TYPE: PRT
<213> ORGANISM: Homo sapiens

<400> SEQUENCE: 226

Lys Thr Phe Asn Leu Ile Pro Ala Val
1               5

<210> SEQ ID NO 227
<211> LENGTH: 9
<212> TYPE: PRT
<213> ORGANISM: Homo sapiens

<400> SEQUENCE: 227

Asn Leu Phe Asn Val Thr Pro Leu Ile
1               5

<210> SEQ ID NO 228
<211> LENGTH: 9
<212> TYPE: PRT
<213> ORGANISM: Homo sapiens

<400> SEQUENCE: 228

Ser Tyr Trp Asn Ile Ile Ser Thr Val
1               5

<210> SEQ ID NO 229
<211> LENGTH: 9
<212> TYPE: PRT
<213> ORGANISM: Homo sapiens

<400> SEQUENCE: 229

Gly Val Phe Asn Leu Ile Ala Val Leu
1               5

<210> SEQ ID NO 230
<211> LENGTH: 9
<212> TYPE: PRT
<213> ORGANISM: Homo sapiens

<400> SEQUENCE: 230

Arg Leu Phe Asn Ile Thr Ser Ser Ala
1               5

<210> SEQ ID NO 231
<211> LENGTH: 9
<212> TYPE: PRT
<213> ORGANISM: Homo sapiens

<400> SEQUENCE: 231

Asn Leu Trp Asn Leu Val Ala Val Ile
1               5

<210> SEQ ID NO 232
<211> LENGTH: 9
<212> TYPE: PRT
<213> ORGANISM: Homo sapiens

<400> SEQUENCE: 232

Arg Ile Phe Asn Leu Ile Gly Met Met
1               5

<210> SEQ ID NO 233
<211> LENGTH: 9
<212> TYPE: PRT
```

<213> ORGANISM: Homo sapiens

<400> SEQUENCE: 233

Arg Leu Phe Asn Val Val Ser Arg Gly
1               5

<210> SEQ ID NO 234
<211> LENGTH: 9
<212> TYPE: PRT
<213> ORGANISM: Homo sapiens

<400> SEQUENCE: 234

Leu Val Phe Asn Val Ile Pro Thr Leu
1               5

<210> SEQ ID NO 235
<211> LENGTH: 9
<212> TYPE: PRT
<213> ORGANISM: Homo sapiens

<400> SEQUENCE: 235

Thr Thr Trp Asn Ile Leu Ser Ser Ala
1               5

<210> SEQ ID NO 236
<211> LENGTH: 9
<212> TYPE: PRT
<213> ORGANISM: Homo sapiens

<400> SEQUENCE: 236

Lys Leu Phe Asn Val Leu Ser Thr Leu
1               5

<210> SEQ ID NO 237
<211> LENGTH: 9
<212> TYPE: PRT
<213> ORGANISM: Homo sapiens

<400> SEQUENCE: 237

Arg Val Tyr Asn Leu Thr Ala Lys Ser
1               5

<210> SEQ ID NO 238
<211> LENGTH: 9
<212> TYPE: PRT
<213> ORGANISM: Homo sapiens

<400> SEQUENCE: 238

Leu Thr Phe Asn Thr Ile Ser Leu Ser
1               5

<210> SEQ ID NO 239
<211> LENGTH: 9
<212> TYPE: PRT
<213> ORGANISM: Homo sapiens

<400> SEQUENCE: 239

Ala Gln Phe Asn Leu Leu Ser Ser Thr
1               5

<210> SEQ ID NO 240
<211> LENGTH: 9
<212> TYPE: PRT
<213> ORGANISM: Homo sapiens

```
<400> SEQUENCE: 240

Val Val Tyr Asn Val Leu Ser Glu Leu
1               5

<210> SEQ ID NO 241
<211> LENGTH: 9
<212> TYPE: PRT
<213> ORGANISM: Homo sapiens

<400> SEQUENCE: 241

Lys Val Tyr Asn Thr Pro Ser Thr Ser
1               5

<210> SEQ ID NO 242
<211> LENGTH: 9
<212> TYPE: PRT
<213> ORGANISM: Homo sapiens

<400> SEQUENCE: 242

Gly Ile Phe Asn Ile Ile Pro Ser Thr
1               5

<210> SEQ ID NO 243
<211> LENGTH: 9
<212> TYPE: PRT
<213> ORGANISM: Homo sapiens

<400> SEQUENCE: 243

Asn Ile Tyr Asn Thr Leu Ser Gly Leu
1               5

<210> SEQ ID NO 244
<211> LENGTH: 9
<212> TYPE: PRT
<213> ORGANISM: Homo sapiens

<400> SEQUENCE: 244

Arg Leu Phe Asn Leu Thr Ser Thr Phe
1               5

<210> SEQ ID NO 245
<211> LENGTH: 9
<212> TYPE: PRT
<213> ORGANISM: Homo sapiens

<400> SEQUENCE: 245

Thr Val Trp Asn Thr Leu Ser Ser Leu
1               5

<210> SEQ ID NO 246
<211> LENGTH: 9
<212> TYPE: PRT
<213> ORGANISM: Homo sapiens

<400> SEQUENCE: 246

Arg Leu Phe Asn Met Leu Ser Ala Val
1               5

<210> SEQ ID NO 247
<211> LENGTH: 9
<212> TYPE: PRT
<213> ORGANISM: Homo sapiens

<400> SEQUENCE: 247
```

```
Ser Ile Trp Asn Val Thr Ala Ile Ala
1               5

<210> SEQ ID NO 248
<211> LENGTH: 9
<212> TYPE: PRT
<213> ORGANISM: Homo sapiens

<400> SEQUENCE: 248

Ala Leu Phe Asn Leu Met Ser Gly Ile
1               5

<210> SEQ ID NO 249
<211> LENGTH: 9
<212> TYPE: PRT
<213> ORGANISM: Homo sapiens

<400> SEQUENCE: 249

Ile Val Tyr Asn Leu Leu Ser Ala Met
1               5

<210> SEQ ID NO 250
<211> LENGTH: 9
<212> TYPE: PRT
<213> ORGANISM: Homo sapiens

<400> SEQUENCE: 250

Ile Ser Phe Asn Met Leu Pro Ser Ile
1               5

<210> SEQ ID NO 251
<211> LENGTH: 9
<212> TYPE: PRT
<213> ORGANISM: Homo sapiens

<400> SEQUENCE: 251

Asn Thr Tyr Asn Ile Leu Pro Gly Ser
1               5

<210> SEQ ID NO 252
<211> LENGTH: 9
<212> TYPE: PRT
<213> ORGANISM: Homo sapiens

<400> SEQUENCE: 252

Arg Leu Trp Asn Met Val Asn Val Thr
1               5

<210> SEQ ID NO 253
<211> LENGTH: 9
<212> TYPE: PRT
<213> ORGANISM: Homo sapiens

<400> SEQUENCE: 253

Ser Ala Phe Asn Ile Thr Ser Leu Ile
1               5

<210> SEQ ID NO 254
<211> LENGTH: 9
<212> TYPE: PRT
<213> ORGANISM: Homo sapiens

<400> SEQUENCE: 254

Asn Ile Phe Asn Leu Pro Asn Ile Val
1               5
```

```
<210> SEQ ID NO 255
<211> LENGTH: 9
<212> TYPE: PRT
<213> ORGANISM: Homo sapiens

<400> SEQUENCE: 255

Gly Val Tyr Asn Leu Pro Gly Ala Ser
1               5

<210> SEQ ID NO 256
<211> LENGTH: 9
<212> TYPE: PRT
<213> ORGANISM: Homo sapiens

<400> SEQUENCE: 256

Gly Thr Tyr Asn Val Ile Ser Leu Val
1               5

<210> SEQ ID NO 257
<211> LENGTH: 9
<212> TYPE: PRT
<213> ORGANISM: Homo sapiens

<400> SEQUENCE: 257

Ser Ile Phe Asn Thr Leu Ser Asp Ile
1               5

<210> SEQ ID NO 258
<211> LENGTH: 9
<212> TYPE: PRT
<213> ORGANISM: Homo sapiens

<400> SEQUENCE: 258

Thr Ile Phe Asn Ile Leu Ser Gly Ile
1               5

<210> SEQ ID NO 259
<211> LENGTH: 9
<212> TYPE: PRT
<213> ORGANISM: Homo sapiens

<400> SEQUENCE: 259

Leu Leu Phe Asn Leu Ile Ser Ser Ser
1               5

<210> SEQ ID NO 260
<211> LENGTH: 9
<212> TYPE: PRT
<213> ORGANISM: Homo sapiens

<400> SEQUENCE: 260

Arg Thr Phe Asn Leu Thr Ala Gly Ser
1               5

<210> SEQ ID NO 261
<211> LENGTH: 9
<212> TYPE: PRT
<213> ORGANISM: Homo sapiens

<400> SEQUENCE: 261

Thr Val Phe Asn Ile Leu Pro Gly Gly
1               5
```

```
<210> SEQ ID NO 262
<211> LENGTH: 9
<212> TYPE: PRT
<213> ORGANISM: Homo sapiens

<400> SEQUENCE: 262

Gly Leu Phe Asn Ile Pro Pro Ala Ser
1               5

<210> SEQ ID NO 263
<211> LENGTH: 9
<212> TYPE: PRT
<213> ORGANISM: Homo sapiens

<400> SEQUENCE: 263

Arg Met Phe Asn Ile Ile Ser Asp Ser
1               5

<210> SEQ ID NO 264
<211> LENGTH: 9
<212> TYPE: PRT
<213> ORGANISM: Homo sapiens

<400> SEQUENCE: 264

Thr Thr Phe Asn Ile Val Gly Thr Thr
1               5

<210> SEQ ID NO 265
<211> LENGTH: 9
<212> TYPE: PRT
<213> ORGANISM: Homo sapiens

<400> SEQUENCE: 265

Ala Leu Phe Asn Leu Met Ser Gly Val
1               5

<210> SEQ ID NO 266
<211> LENGTH: 9
<212> TYPE: PRT
<213> ORGANISM: Homo sapiens

<400> SEQUENCE: 266

Ser Val Phe Asn Ile Thr Ala Ile Ala
1               5

<210> SEQ ID NO 267
<211> LENGTH: 9
<212> TYPE: PRT
<213> ORGANISM: Homo sapiens

<400> SEQUENCE: 267

Lys Ile Tyr Asn Thr Pro Ser Ala Ser
1               5

<210> SEQ ID NO 268
<211> LENGTH: 9
<212> TYPE: PRT
<213> ORGANISM: Homo sapiens

<400> SEQUENCE: 268

Leu Leu Tyr Asn Leu Leu Gly Ser Ser
1               5

<210> SEQ ID NO 269
<211> LENGTH: 9
```

```
<212> TYPE: PRT
<213> ORGANISM: Homo sapiens

<400> SEQUENCE: 269

Ser Leu Tyr Asn Met Met Gly Glu Ala
1               5

<210> SEQ ID NO 270
<211> LENGTH: 9
<212> TYPE: PRT
<213> ORGANISM: Homo sapiens

<400> SEQUENCE: 270

Ser Leu Trp Asn Leu Met Gly Asn Ala
1               5

<210> SEQ ID NO 271
<211> LENGTH: 9
<212> TYPE: PRT
<213> ORGANISM: Homo sapiens

<400> SEQUENCE: 271

Gly Leu Tyr Asn Ile Val Gly Asn Ala
1               5

<210> SEQ ID NO 272
<211> LENGTH: 9
<212> TYPE: PRT
<213> ORGANISM: Homo sapiens

<400> SEQUENCE: 272

Leu Thr Trp Asn Leu Thr Pro Lys Ala
1               5

<210> SEQ ID NO 273
<211> LENGTH: 9
<212> TYPE: PRT
<213> ORGANISM: Homo sapiens

<400> SEQUENCE: 273

Leu Ile Phe Asn Val Thr Gly Leu Ala
1               5

<210> SEQ ID NO 274
<211> LENGTH: 9
<212> TYPE: PRT
<213> ORGANISM: Homo sapiens

<400> SEQUENCE: 274

Ser Ile Phe Asn Ile Thr Gly Ile Ala
1               5

<210> SEQ ID NO 275
<211> LENGTH: 9
<212> TYPE: PRT
<213> ORGANISM: Homo sapiens

<400> SEQUENCE: 275

Leu Thr Phe Asn Leu Val Ser Asp Ala
1               5

<210> SEQ ID NO 276
<211> LENGTH: 9
<212> TYPE: PRT
<213> ORGANISM: Homo sapiens
```

<400> SEQUENCE: 276

Met Gln Trp Asn Ile Leu Ala Gln Ala
1               5

<210> SEQ ID NO 277
<211> LENGTH: 9
<212> TYPE: PRT
<213> ORGANISM: Homo sapiens

<400> SEQUENCE: 277

Leu Ser Trp Asn Leu Val Pro Glu Ala
1               5

<210> SEQ ID NO 278
<211> LENGTH: 9
<212> TYPE: PRT
<213> ORGANISM: Homo sapiens

<400> SEQUENCE: 278

Asp Leu Trp Asn Thr Leu Ser Glu Ala
1               5

<210> SEQ ID NO 279
<211> LENGTH: 9
<212> TYPE: PRT
<213> ORGANISM: Homo sapiens

<400> SEQUENCE: 279

Gly Leu Phe Asn Ile Pro Pro Ala Phe
1               5

<210> SEQ ID NO 280
<211> LENGTH: 9
<212> TYPE: PRT
<213> ORGANISM: Homo sapiens

<400> SEQUENCE: 280

Leu Ile Trp Asn Ile Leu Ala Ser Phe
1               5

<210> SEQ ID NO 281
<211> LENGTH: 9
<212> TYPE: PRT
<213> ORGANISM: Homo sapiens

<400> SEQUENCE: 281

Leu Leu Phe Asn Met Leu Pro Gly Gly
1               5

<210> SEQ ID NO 282
<211> LENGTH: 9
<212> TYPE: PRT
<213> ORGANISM: Homo sapiens

<400> SEQUENCE: 282

Leu Val Tyr Asn Ile Met Ser Ser Gly
1               5

<210> SEQ ID NO 283
<211> LENGTH: 9
<212> TYPE: PRT
<213> ORGANISM: Homo sapiens

<400> SEQUENCE: 283

Ile Ile Tyr Asn Val Pro Gly Thr Gly
1               5

<210> SEQ ID NO 284
<211> LENGTH: 9
<212> TYPE: PRT
<213> ORGANISM: Homo sapiens

<400> SEQUENCE: 284

Val Ile Tyr Asn Val Thr Ser Asp Gly
1               5

<210> SEQ ID NO 285
<211> LENGTH: 9
<212> TYPE: PRT
<213> ORGANISM: Homo sapiens

<400> SEQUENCE: 285

Gly Thr Phe Asn Leu Pro Ser Asp Gly
1               5

<210> SEQ ID NO 286
<211> LENGTH: 9
<212> TYPE: PRT
<213> ORGANISM: Homo sapiens

<400> SEQUENCE: 286

Lys Leu Trp Asn Thr Leu Asn Leu Ile
1               5

<210> SEQ ID NO 287
<211> LENGTH: 9
<212> TYPE: PRT
<213> ORGANISM: Homo sapiens

<400> SEQUENCE: 287

Leu Met Trp Asn Ile Ile Ser Ile Ile
1               5

<210> SEQ ID NO 288
<211> LENGTH: 9
<212> TYPE: PRT
<213> ORGANISM: Homo sapiens

<400> SEQUENCE: 288

Gly Leu Phe Asn Thr Thr Ser Asn Ile
1               5

<210> SEQ ID NO 289
<211> LENGTH: 9
<212> TYPE: PRT
<213> ORGANISM: Homo sapiens

<400> SEQUENCE: 289

Leu Ile Phe Asn Thr Leu Ser Leu Ile
1               5

<210> SEQ ID NO 290
<211> LENGTH: 9
<212> TYPE: PRT
<213> ORGANISM: Homo sapiens

<400> SEQUENCE: 290

Ser Val Phe Asn Leu Met Asn Ala Ile

```
<210> SEQ ID NO 291
<211> LENGTH: 9
<212> TYPE: PRT
<213> ORGANISM: Homo sapiens

<400> SEQUENCE: 291

Leu Thr Phe Asn Ile Leu Gly Gln Ile
1               5

<210> SEQ ID NO 292
<211> LENGTH: 9
<212> TYPE: PRT
<213> ORGANISM: Homo sapiens

<400> SEQUENCE: 292

Gly Leu Phe Asn Met Val Ser Ser Leu
1               5

<210> SEQ ID NO 293
<211> LENGTH: 9
<212> TYPE: PRT
<213> ORGANISM: Homo sapiens

<400> SEQUENCE: 293

Lys Ile Phe Asn Ile Ile Asn Ser Leu
1               5

<210> SEQ ID NO 294
<211> LENGTH: 9
<212> TYPE: PRT
<213> ORGANISM: Homo sapiens

<400> SEQUENCE: 294

Ala Val Trp Asn Val Leu Gly Asn Leu
1               5

<210> SEQ ID NO 295
<211> LENGTH: 9
<212> TYPE: PRT
<213> ORGANISM: Homo sapiens

<400> SEQUENCE: 295

Lys Val Phe Asn Ile Val Ser Asp Leu
1               5

<210> SEQ ID NO 296
<211> LENGTH: 9
<212> TYPE: PRT
<213> ORGANISM: Homo sapiens

<400> SEQUENCE: 296

Asp Leu Trp Asn Val Val Ser His Leu
1               5

<210> SEQ ID NO 297
<211> LENGTH: 9
<212> TYPE: PRT
<213> ORGANISM: Homo sapiens

<400> SEQUENCE: 297

Leu Gln Phe Asn Thr Val Ser Lys Leu
1               5
```

```
<210> SEQ ID NO 298
<211> LENGTH: 9
<212> TYPE: PRT
<213> ORGANISM: Homo sapiens

<400> SEQUENCE: 298

Met Ser Phe Asn Thr Val Ser Glu Leu
1               5

<210> SEQ ID NO 299
<211> LENGTH: 9
<212> TYPE: PRT
<213> ORGANISM: Homo sapiens

<400> SEQUENCE: 299

Ala Ser Trp Asn Ile Val Asn Leu Leu
1               5

<210> SEQ ID NO 300
<211> LENGTH: 9
<212> TYPE: PRT
<213> ORGANISM: Homo sapiens

<400> SEQUENCE: 300

Ile Ser Phe Asn Ile Ile Ser Ala Leu
1               5

<210> SEQ ID NO 301
<211> LENGTH: 9
<212> TYPE: PRT
<213> ORGANISM: Homo sapiens

<400> SEQUENCE: 301

Ala Phe Phe Asn Ile Leu Asn Glu Leu
1               5

<210> SEQ ID NO 302
<211> LENGTH: 9
<212> TYPE: PRT
<213> ORGANISM: Homo sapiens

<400> SEQUENCE: 302

Leu Val Phe Asn Leu Leu Pro Ile Met
1               5

<210> SEQ ID NO 303
<211> LENGTH: 9
<212> TYPE: PRT
<213> ORGANISM: Homo sapiens

<400> SEQUENCE: 303

Lys Ile Phe Asn Thr Val Pro Asp Met
1               5

<210> SEQ ID NO 304
<211> LENGTH: 9
<212> TYPE: PRT
<213> ORGANISM: Homo sapiens

<400> SEQUENCE: 304

Met Leu Phe Asn Leu Ile Gly Leu Ser
1               5

<210> SEQ ID NO 305
```

```
<211> LENGTH: 9
<212> TYPE: PRT
<213> ORGANISM: Homo sapiens

<400> SEQUENCE: 305

Leu Leu Phe Asn Leu Pro Pro Gly Ser
1               5

<210> SEQ ID NO 306
<211> LENGTH: 9
<212> TYPE: PRT
<213> ORGANISM: Homo sapiens

<400> SEQUENCE: 306

Met Thr Phe Asn Leu Ile Gly Glu Ser
1               5

<210> SEQ ID NO 307
<211> LENGTH: 9
<212> TYPE: PRT
<213> ORGANISM: Homo sapiens

<400> SEQUENCE: 307

Lys Val Tyr Asn Ile Pro Gly Ile Ser
1               5

<210> SEQ ID NO 308
<211> LENGTH: 9
<212> TYPE: PRT
<213> ORGANISM: Homo sapiens

<400> SEQUENCE: 308

Gly Ile Tyr Asn Ile Pro Gly Asp Ser
1               5

<210> SEQ ID NO 309
<211> LENGTH: 9
<212> TYPE: PRT
<213> ORGANISM: Homo sapiens

<400> SEQUENCE: 309

Gly Leu Tyr Asn Leu Met Asn Ile Thr
1               5

<210> SEQ ID NO 310
<211> LENGTH: 9
<212> TYPE: PRT
<213> ORGANISM: Homo sapiens

<400> SEQUENCE: 310

Leu Thr Trp Asn Met Ile Asn Thr Thr
1               5

<210> SEQ ID NO 311
<211> LENGTH: 9
<212> TYPE: PRT
<213> ORGANISM: Homo sapiens

<400> SEQUENCE: 311

Ile Val Phe Asn Val Leu Ser Asp Thr
1               5

<210> SEQ ID NO 312
<211> LENGTH: 9
<212> TYPE: PRT
```

<213> ORGANISM: Homo sapiens

<400> SEQUENCE: 312

Ile Val Phe Asn Val Val Ser Asp Thr
1               5

<210> SEQ ID NO 313
<211> LENGTH: 9
<212> TYPE: PRT
<213> ORGANISM: Homo sapiens

<400> SEQUENCE: 313

Leu Ile Phe Asn Ile Thr Ala Ser Val
1               5

<210> SEQ ID NO 314
<211> LENGTH: 9
<212> TYPE: PRT
<213> ORGANISM: Homo sapiens

<400> SEQUENCE: 314

Ile Val Phe Asn Leu Thr Asn Asn Val
1               5

<210> SEQ ID NO 315
<211> LENGTH: 9
<212> TYPE: PRT
<213> ORGANISM: Homo sapiens

<400> SEQUENCE: 315

Lys Ser Phe Asn Val Leu Ser Ser Val
1               5

<210> SEQ ID NO 316
<211> LENGTH: 9
<212> TYPE: PRT
<213> ORGANISM: Homo sapiens

<400> SEQUENCE: 316

Leu Ala Phe Asn Ile Leu Gly Met Val
1               5

<210> SEQ ID NO 317
<211> LENGTH: 9
<212> TYPE: PRT
<213> ORGANISM: Homo sapiens

<400> SEQUENCE: 317

Val Ser Trp Asn Ile Thr Gly Thr Val
1               5

<210> SEQ ID NO 318
<211> LENGTH: 9
<212> TYPE: PRT
<213> ORGANISM: Artificial Sequence
<220> FEATURE:
<223> OTHER INFORMATION: Peptide ligand sequence

<400> SEQUENCE: 318

Ser Leu Phe Asn Thr Ile Ala Val Leu
1               5

<210> SEQ ID NO 319
<211> LENGTH: 8
<212> TYPE: PRT

-continued

```
<213> ORGANISM: Artificial Sequence
<220> FEATURE:
<223> OTHER INFORMATION: Peptide ligand sequence

<400> SEQUENCE: 319

Ser Leu Phe Asn Thr Val Ala Val
1               5

<210> SEQ ID NO 320
<211> LENGTH: 9
<212> TYPE: PRT
<213> ORGANISM: Artificial Sequence
<220> FEATURE:
<223> OTHER INFORMATION: Peptide ligand sequence

<400> SEQUENCE: 320

Ser Leu Phe Asn Thr Ile Ala Thr Leu
1               5

<210> SEQ ID NO 321
<211> LENGTH: 9
<212> TYPE: PRT
<213> ORGANISM: Artificial Sequence
<220> FEATURE:
<223> OTHER INFORMATION: Peptide ligand sequence

<400> SEQUENCE: 321

Ser Leu Tyr Asn Thr Ile Ala Val Leu
1               5

<210> SEQ ID NO 322
<211> LENGTH: 275
<212> TYPE: PRT
<213> ORGANISM: Homo sapiens

<400> SEQUENCE: 322

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190
```

```
Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
            245                 250                 255

Tyr Thr Cys His Val Gln His Glu Gly Leu Pro Lys Pro Leu Thr Leu
            260                 265                 270

Arg Trp Glu
        275

<210> SEQ ID NO 323
<211> LENGTH: 275
<212> TYPE: PRT
<213> ORGANISM: Artificial sequence
<220> FEATURE:
<223> OTHER INFORMATION: Y84C/A139C HLA-A*02:01 variant sequence

<400> SEQUENCE: 323

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Cys Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
            165                 170                 175

Glu Thr Leu Gln Arg Thr Asp Ala Pro Lys Thr His Met Thr His His
        180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
            210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
            245                 250                 255

Tyr Thr Cys His Val Gln His Glu Gly Leu Pro Lys Pro Leu Thr Leu
            260                 265                 270
```

Arg Trp Glu
        275

<210> SEQ ID NO 324
<211> LENGTH: 275
<212> TYPE: PRT
<213> ORGANISM: Artificial Sequence
<220> FEATURE:
<223> OTHER INFORMATION: F22C/S71C HLA-A*02:01 variant

<400> SEQUENCE: 324

Gly Ser His Ser Met Arg Tyr Phe Phe Thr Ser Val Ser Arg Pro Gly
1               5                   10                  15

Arg Gly Glu Pro Arg Cys Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Cys Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 325
<211> LENGTH: 275
<212> TYPE: PRT
<213> ORGANISM: Artificial Sequence
<220> FEATURE:
<223> OTHER INFORMATION: F22C/S71C W51C/G175C HLA-A*02:01 variant

<400> SEQUENCE: 325

Gly Ser His Ser Met Arg Tyr Phe Phe Thr Ser Val Ser Arg Pro Gly
1               5                   10                  15

```
Arg Gly Glu Pro Arg Cys Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Cys Ile Glu Gln Glu Gly Pro Glu Tyr Trp Asp Gly Glu Thr
    50                  55                  60

Arg Lys Val Lys Ala His Cys Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Cys Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 326
<211> LENGTH: 6
<212> TYPE: PRT
<213> ORGANISM: Artificial Sequence
<220> FEATURE:
<223> OTHER INFORMATION: CDR2beta

<400> SEQUENCE: 326

Tyr Tyr Glu Glu Glu Glu
1               5

<210> SEQ ID NO 327
<211> LENGTH: 6
<212> TYPE: PRT
<213> ORGANISM: Artificial Sequence
<220> FEATURE:
<223> OTHER INFORMATION: CDR2beta

<400> SEQUENCE: 327

Tyr Val Arg Gly Glu Glu
1               5
```

<210> SEQ ID NO 328
<211> LENGTH: 12
<212> TYPE: PRT
<213> ORGANISM: Artificial Sequence
<220> FEATURE:
<223> OTHER INFORMATION: CDR3alpha

<400> SEQUENCE: 328

Cys Ala Val Arg Thr Asn Ser Gly Tyr Ala Leu Asn
1               5                   10

<210> SEQ ID NO 329
<211> LENGTH: 12
<212> TYPE: PRT
<213> ORGANISM: Artificial Sequence
<220> FEATURE:
<223> OTHER INFORMATION: CDR3alpha

<400> SEQUENCE: 329

Cys Ala Val Arg Gly Ala His Asp Tyr Ala Leu Asn
1               5                   10

<210> SEQ ID NO 330
<211> LENGTH: 17
<212> TYPE: PRT
<213> ORGANISM: Artificial Sequence
<220> FEATURE:
<223> OTHER INFORMATION: Linker

<400> SEQUENCE: 330

Gly Ser Ala Asp Asp Ala Lys Lys Asp Ala Ala Lys Lys Asp Gly Lys
1               5                   10                  15

Ser

<210> SEQ ID NO 331
<211> LENGTH: 339
<212> TYPE: PRT
<213> ORGANISM: Mus musculus

<400> SEQUENCE: 331

Gly Pro His Ser Leu Arg Tyr Phe Val Thr Ala Val Ser Arg Pro Gly
1               5                   10                  15

Leu Gly Glu Pro Arg Tyr Met Glu Val Gly Tyr Val Asp Asp Thr Glu
                20                  25                  30

Phe Val Arg Phe Asp Ser Asp Ala Glu Asn Pro Arg Tyr Glu Pro Arg
            35                  40                  45

Ala Arg Trp Met Glu Gln Glu Gly Pro Glu Tyr Trp Glu Arg Glu Thr
        50                  55                  60

Gln Lys Ala Lys Gly Asn Glu Gln Ser Phe Arg Val Asp Leu Arg Thr
65                  70                  75                  80

Leu Leu Gly Tyr Tyr Asn Gln Ser Lys Gly Gly Ser His Thr Ile Gln
                85                  90                  95

Val Ile Ser Gly Cys Glu Val Gly Ser Asp Gly Arg Leu Leu Arg Gly
            100                 105                 110

Tyr Gln Gln Tyr Ala Tyr Asp Gly Cys Asp Tyr Ile Ala Leu Asn Glu
        115                 120                 125

Asp Leu Lys Thr Trp Thr Ala Ala Asp Met Ala Ala Leu Ile Thr Lys
130                 135                 140

His Lys Trp Glu Gln Ala Gly Glu Ala Glu Arg Leu Arg Ala Tyr Leu
                145                 150                 155                 160

Glu Gly Thr Cys Val Glu Trp Leu Arg Arg Tyr Leu Lys Asn Gly Asn

-continued

```
                 165                 170                 175
Ala Thr Leu Leu Arg Thr Asp Ser Pro Lys Ala His Val Thr His His
            180                 185                 190

Ser Arg Pro Glu Asp Lys Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Ile Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Tyr
            245                 250                 255

Tyr Thr Cys His Val Tyr His Gln Gly Leu Pro Glu Pro Leu Thr Leu
            260                 265                 270

Arg Trp Glu Pro Pro Pro Ser Thr Val Ser Asn Met Ala Thr Val Ala
        275                 280                 285

Val Leu Val Val Leu Gly Ala Ala Ile Val Thr Gly Ala Val Val Ala
        290                 295                 300

Phe Val Met Lys Met Arg Arg Arg Asn Thr Gly Gly Lys Gly Gly Asp
305                 310                 315                 320

Tyr Ala Leu Ala Pro Gly Ser Gln Thr Ser Asp Leu Ser Leu Pro Asp
                325                 330                 335

Cys Lys Ala
```

…

METHOD FOR HIGH THROUGHPUT PEPTIDE-MHC AFFINITY SCREENING FOR TCR LIGANDS

CROSS-REFERENCE TO RELATED APPLICATIONS

This Non-Provisional application claims priority to U.S. Provisional Application No. 62/731,337, filed 14 Sep. 2018, German Patent Application 102018122546.6, filed 14 Sep. 2018, and U.S. Provisional Application No. 62/873,102, filed 11 Jul. 2019. Each of these applications is incorporated by reference in its entirety

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "3000058-013002_Substitute_Sequence_Listing.txt" created on 24 May 2022, and 102,307 bytes in size) is submitted concurrently with the instant application, and the entire contents of the Sequence Listing are incorporated herein by reference.

The present invention relates to a method for high throughput screening for a TCR-binding peptide ligand/MHC molecule complex, comprising a stabilized peptide-MHC molecule and respective uses of said method. The present invention further relates to polypeptides comprising or consisting of stabilized MHC molecules or peptide binding fragments thereof, pharmaceutical compositions comprising said polypeptides, vaccines comprising said pharmaceutical composition and uses of said vaccine for the manufacturing of a medicament and/or in the prevention of cancer The present invention further relates to nucleic acids encoding said polypeptides and vectors comprising said nucleic acids.

BACKGROUND OF THE INVENTION

Presentation of peptides on cell surface MHC molecules plays a fundamental role for the immune response against viral infection or cancer (1). MHC class I molecules are trimeric complexes that consist of a polymorphic heavy chain, beta-2 microglobulin ($\beta_2$m) and a peptide ligand, typically between 8 and 10 amino acids long and derived from degradation of cytosolic proteins. T cells can recognize specific peptide-MHC complexes (pMHC) with their clone-specific T cell receptor (TCR) and initiate an immune response.

Production of soluble pMHC complexes is important for many different applications in scientific and clinical fields that are centered around the interaction between pMHCs and TCRs. They were first generated using protein expression and refolding techniques in 1992 and have since then been used for many applications, e.g. identification of antigen-specific T cells through flow cytometry or affinity measurements of the TCR-pMHC interaction (2 to 5).

The affinity of the TCR towards its cognate pMHC has a substantial impact on the functionality of the expressing T cell (6). Thus, efforts have been made to improve the affinity of low-affinity TCRs to reach optimal levels for clinical applications (7). Extensive maturation experiments have produced TCRs with picomolar affinities, a range normally reserved to antibodies. They bind targeted pMHCs with long interaction half-lives even in monomeric form and have thus attracted attention as tumor cell engaging component in bi-specific T cell engager formats (8, 9).

WO 2013/030620 discloses recombinant MHC class I molecules which are produced in bacteria and are present as an insoluble attachment body for a detection of epitope-specific CTL. These are first denatured in a solution of a chaotropic agent. The chaotrope is then removed in the presence of the desired peptide (renaturing, refolding) and the peptide class I complex is separated by gel filtration chromatography from the unfolded protein. WO 2013/030620 presents a gene for encoding an MHC class I molecule, the MHC class I molecule having an alpha 1 helix and an alpha 2 helix and the gene being encoded such that a bond is formed between the alpha 1 helix and the alpha 2 helix in the MHC class I molecule. Thus, a kit for analysis of T cell frequencies can be provided. Amino acid 139 is substituted by a cysteine so as to provide Cys-139, the amino acid 84 is substituted by the cysteine so as to provide Cys-84 or the amino acid 85 is substituted by the cysteine so as to provide Cys-85, the disulfide bridge is formed between the alpha-1 helix and the alpha-2 helix in the MHC class I heavy chain between Cys-139 and Cys-84 or between Cys-139 and Cys-85.

US 2009-0117153 discloses a so-called disulfide trap, comprising an antigen peptide covalently attached to an MHC class I heavy chain molecule by a disulfide bond extending between two cysteines. In some configurations, a disulfide trap, such as a disulfide trap single chain trimer (dtSCT), can comprise a single contiguous polypeptide chain. Upon synthesis in a cell, a disulfide trap oxidizes properly in the ER, and can be recognized by T cells. In some configurations, a peptide moiety of a disulfide trap is not displaced by high-affinity competitor peptides, even if the peptide binds the heavy chain relatively weakly. In various configurations, a disulfide trap can be used for vaccination, to elicit CD8 T cells, and in multivalent MHC/peptide reagents for the enumeration and tracking of T cells. Also disclosed are nucleic acids comprising a sequence encoding a disulfide trap. Such nucleic acids, which can be DNA vectors, can be used as vaccines.

Zeynep Hein, et al. (in: Peptide-independent stabilization of MHC class I molecules breaches cellular quality control. J Cell Sci 2014 127: 2885-2897) describe a variant of the murine MHC-I allotype H-2Kb, in which the $\alpha 1$ and $\alpha 2$ helices are connected by a disulfide bond close to the F-pocket, restricting their mobility. The C84-C139 disulfide bond allows normal PLC interaction and antigen presentation but renders MHC-I surface expression TAP- and tapasin-independent, accelerates anterograde transport, and greatly decreases the rate of MHC-I endocytosis.

WO 2011/101681 discloses disulfide bond stabilized recombinant MHC class II molecules that are linked by a disulfide bond between cysteine residues located in the $\alpha 2$ domain of said $\alpha$ chain and the $\beta 2$ domain of said $\beta$ chain, wherein said cysteine residues are not present in native MHC class II $\alpha 2$ and $\beta 2$ domains.

WO 2018/029350 discloses a $K_{on}$-rate assay and an improved TCR ligand $k_{off}$-rate assay, which enables a broader application through a novel combination with UV peptide exchange technology. The disclosure enables $K_{off}$-rate MHC monomer preparation in a high throughput manner, which can then be used to screen TCR candidates for extended peptide libraries in assays such as the TCR ligand $K_{off}$-rate assay that was previously not feasible. Further, the UV peptide exchange with the $K_{off}$-rate MHC monomers allows the analysis of TCR candidates recognizing specific peptides carrying the amino acid cysteine, which previously could interfere with or even abolish the $k_{off}$-rate measurement.

Newell et al. (in: Newell E W, "Higher Throughput Methods of Identifying T Cell Epitopes for Studying Outcomes of Altered Antigen Processing and Presentation." Frontiers in Immunology. 2013; 4:430) disclose high content combinatorial peptide-MHC tetramer staining using mass cytometry.

Bakker et al. (in: Bakker A H, Hoppes R, Linnemann C, et al., "Conditional MHC class I ligands and peptide exchange technology for the human MHC gene products HLA-A1, -A3, -A11, and -B7." *PNAS* 2008; 105(10):3825-3830) disclose conditional ligands that disintegrate upon exposure to long-wavelength UV light that can be designed for the human MHC molecule HLA-A2. This peptide-exchange technology allegedly can be developed into a generally applicable approach for high throughput MHC based applications for an analysis of cytotoxic T cell immunity.

Cochran and Stern (in: "A diverse set of oligomeric class II MHC-peptide complexes for probing T-cell receptor interactions." Chem Biol. 2000 September; 7(9):683-96) disclose tools to study the molecular mechanisms responsible for initiation of activation processes in T-cells. A topologically diverse set of oligomers of the human MHC protein HLA-DR1, varying in size from dimers to tetramers, was produced by varying the location of an introduced cysteine residue and the number and spacing of sulfhydryl-reactive groups carried on novel and commercially available cross-linking reagents. Fluorescent probes incorporated into the cross-linking reagents facilitated measurement of oligomer binding to the T-cell surface. Oligomeric MHC-peptide complexes, including a variety of MHC dimers, trimers and tetramers, bound to T-cells and initiated T-cell activation processes in an antigen-specific manner.

Chong et al. (in: "High-throughput and Sensitive Immunopeptidomics Platform Reveals Profound Interferon-γ-Mediated Remodeling of the Human Leukocyte Antigen (HLA) Ligandome." *Molecular & Cellular Proteomics: MCP.* 2018; 17(3):533-548) disclose a high-throughput, reproducible and sensitive method for sequential immuno-affinity purification of HLA-I and -II peptides from up to 96 samples in a plate format, suitable for both cell lines and tissues. The method is directed at improving the allegedly most critical step in the immunopeptidomics pipeline, the sample preparation, as it determines the overall peptide yield and reproducibility.

Luimstra et al. (in: Luimstra J J, Garstka M A, Roex M C J, et al. "A flexible MHC class I multimer loading system for large-scale detection of antigen-specific T cells." *J Exp Med* 2018; 215(5):1493-1504) disclose an allegedly simple, fast, flexible, and efficient method to generate many different MHC class I (MHC I) multimers in parallel using temperature-mediated peptide exchange. They designed conditional peptides for HLA-A*02:01 and H-2K$^b$ that form stable peptide-MHC I complexes at low temperatures, but dissociate when exposed to a defined elevated temperature. The resulting conditional MHC I complexes, either alone or prepared as ready-to-use multimers, can swiftly be loaded with peptides of choice without additional handling and within a short time frame.

A potential downside of TCR affinity enhancement is the introduction of off-target toxicities. Due to the inherent cross-reactivity of TCRs these can arise by unknowingly increasing the affinity towards other pMHCs as well (10). Multiple cases like these have already been reported in clinical studies (11 to 13).

Comprehensive screening is therefore necessary not only to ensure efficacy but also specificity and safety of therapeutic candidates (14). This is a task of high complexity given the currently established size of the immunopeptidome, with at least 150,000 MHC class I ligand peptides identified by mass spectrometry, and the available methods for pMHC generation (15).

The large-scale generation of pMHC libraries and subsequent high throughput binding screenings of TCRs, e.g. for binding motif generation or the direct identification and characterization of potentially cross-reactive peptides are still difficult to achieve using common technologies in the art, like the ones above. This difficulty extends to the preparation of high quality pMHC complexes even in lower numbers for individuals or institutions without the necessary technically challenging facilities to produce pMHC, e.g. for time sensitive on demand production in clinical settings. It is therefore an object of the present invention, to provide improved strategies in this field. Other objects and aspects of the present invention will become apparent to the person of skill upon reading the following description of the invention.

According to a first aspect thereof, the above object of the invention is solved by a method for screening for a TCR-binding peptide ligand/MHC molecule complex (pMHC), comprising the steps of:
  a) providing a suitably stabilized MHC molecule, wherein said MHC molecule comprises at least one artificially introduced covalent bridge:
    (i) between amino acids of the alpha1 domain and amino acids of the alpha2 domain of said stabilized MHC molecule in case of MHC I; and/or
    (ii) between two amino acids of the alpha1 domain of said stabilized MHC molecule in case of MHC I; or
    (iii) between two amino acids of the alpha1 domain or two amino acids of the beta1 domain of said stabilized MHC molecule in case of MHC II; and/or
    (iv) between one amino acid of the alpha1 domain and one amino acid of the beta1 domain of said stabilized MHC molecule in case of MHC II;
  b) contacting said suitably stabilized MHC molecule with a multitude of peptide ligands thereof, to form peptide ligand/MHC (pMHC) molecule complexes, and
  c) screening said pMHC molecule complexes for TCR-binding.

Preferred is a method according to the invention, wherein said stabilized MHC molecule encompasses at least one artificially introduced covalent disulfide bridge between two amino acids, more preferable at least one artificially introduced covalent bridge between amino acids between α-helices, for example by (i) mutating the amino acid at position 84, a tyrosine in the majority of HLAs (see FIG. 13) and an amino acid at position 139, a alanine in the majority of HLAs (see FIG. 13) into cysteines and/or (ii) mutating an amino acid at position 22, a phenylalanine in the majority of HLAs (see FIG. 13) and an amino acid at position 71, a serine in the majority of HLAs (see FIG. 13) and/or (iii) mutating an amino acid at position 51, a tryptophan in the majority of HLAs (see FIG. 13), and an amino acid at position 175, a glycine in the majority of HLAs (see FIG. 13), or (iv) mutating an amino acid at position 22, a phenylalanine in the majority of HLAs (see FIG. 13) and an amino acid at position 71, a serine in the majority of HLAs (see FIG. 13) and mutating an amino acid at position 51, a tryptophan in the majority of HLAs (see FIG. 13), and an amino acid at position 175, a glycine in the majority of HLAs (see FIG. 13) of MHC I (based on IGMT numbering excluding the first 24 amino acids). Such a stabilized MHC molecule may be referred to as disulfide-modified MHC molecule or disulfide-modified MHC mutant. Either the TCR or the MHC molecule can be suitably immobilized on a solid surface, such as a chip, glass slide, biosensor or bead, in particular as a high-throughput screening format.

In a second aspect the present invention provides a polypeptide comprising or consisting of a stabilized MHC molecule or a peptide binding fragment thereof, which comprises at least one artificially introduced covalent bridge:
(i) between two amino acids in the alpha1 domain of an MHC I; and/or
(ii) between one amino acid in the alpha1 domain of an MHC I and one amino acid in the alpha2 domain of an MCH I within amino acid positions 160 to 179; or
(iii) two amino acids in the alpha1 domain or two amino acids in the beta1 domain of an MHC II; and/or
(iv) between one amino acid in the alpha1 domain of a MHC II and one amino acid in the beta1 domain of a MHC II.

Two amino acid positions that are modified, e.g. by artificially introducing a cysteine residue instead of the naturally occurring amino acid, to form a covalent bridge are selected based on their relative distance. If two amino acids in an MHC I or MHC II that are not linked to each other by peptide bonds naturally have a distance to each other that is similar to the distance of a covalent bond, it is preferred that they are substituted by an amino acid that can form a covalent bond, e.g. a cysteine. Thus, preferably two amino acids are modified that have a distance of between 3 to 7.5 Å in the folded protein (determined between the alpha carbons of the respective amino acids). The 3D structures of a large number of MHC I and MHC II molecules are known and the skilled person can use standard software to determine the distance between two given amino acids within the folded molecules.

If the two amino acids are modified in the alpha1 domain of MHC I it is preferred that one amino acid is modified in the β1 unit and one in the α1 unit of MHC I. Particularly, suitable regions within the β1 unit are within amino acid positions 12 to 32, preferably within amino acid positions 17 to 27, more preferably within amino acid positions 20 to 24 and most preferably amino acid position 22. Particularly, suitable regions within the α1 unit are within amino acid positions 61 to 81, preferably within amino acid positions 66 to 76, more preferably within amino acid positions 69 to 73 and most preferably amino acid position 71. In each case, the two amino acids are preferably selected within the respectively indicated amino acid stretches to have a distance of between 3 to 7.5 Å in the folded MHC I or MHC II protein (determined between the alpha carbons of the respective amino acids).

If the two amino acids are modified in the alpha1 domain of MHC II it is preferred that one amino acid is modified in the β1 unit and one in the α1 unit of MHC II. Particularly, suitable regions within the β1 unit are within amino acid positions 10 to 40, preferably within amino acid positions 13 to 35, more preferably within amino acid positions 22 to 25 and most preferably amino acid position 22. Particularly, suitable regions within the α1 unit are within amino acid positions 45 to 78, preferably within amino acid positions 50 to 70, more preferably within amino acid positions 56 to 66 and most preferably amino acid position 59. In each case, the two amino acids are preferably selected within the respectively indicated amino acid stretches to have a distance of between 3 to 7.5 Å in the folded MHC I or MHC II protein (determined between the alpha carbons of the respective amino acids).

If the two amino acids are modified in the beta1 domain of MHC II it is preferred that one amino acid is modified in the β3 unit and one in the α3 unit of MHC II. Particularly, suitable regions within the β3 unit are within amino acid positions 15 to 53, preferably within amino acid positions 17 to 41, more preferably within amino acid positions 21 to 28 and most preferably amino acid position 26. Particularly, suitable regions within the α3 unit are within amino acid positions 52 to 88, preferably within amino acid positions 66 to 76, more preferably within amino acid positions 65 to 80 and most preferably amino acid position 75. In each case, the two amino acids are preferably selected within the respectively indicated amino acid stretches to have a distance of between 3 to 7.5 Å in the folded MHC I or MHC II protein (determined between the alpha carbons of the respective amino acids).

If one amino acid is modified in the alpha1 domain of an MHC I and one amino acid in the alpha2 domain of an MCH I within amino acid positions 160 to 179, it is preferred that the one amino acid in the alpha1 domain is modified in the α1 unit, preferably within amino acid positions 50 to 70, more preferably within amino acid positions 50 to 60, more preferably 50 to 54 and most preferably amino acid position 51. It is preferred that the other amino acid in the alpha2 domain is modified in the α2 unit, suitable regions are within amino acid positions 165 to 178, preferably within amino acid positions 170 to 177, more preferably within amino acid positions 173 to 176 and most preferably amino acid position 175. In each case the two amino acids are preferably selected within the respectively indicated amino acid stretches to have a distance of between 3 to 7.5 Å in the folded MHC I protein. Thus, in a particularly preferred embodiment the stabilized MHC I comprises a modified amino acid at position 51 and at position 175.

If one amino acid is modified in the alpha1 domain of a MHC II and one amino acid in the beta1 domain of a MHC II it is in one embodiment preferred that one amino acid in the alpha1 domain is modified in the α1 unit. In one pair of modified amino acids the first modified amino acid is within amino acid positions 50 to 70, more preferably within amino acid positions 50 to 60, more preferably 50 to 54 and most preferably amino acid position 51. The other modified amino acid within the beta1 domain is preferably within the α3 unit spanning amino acid positions 70 to 95, preferably within amino acid positions 74 to 94, preferably within amino acid positions 83 to 93, more preferably within amino acid positions 87 to 92 and most preferably amino acid position 89. In another pair the first modified amino acid is within amino acid positions 70 to 90, more preferably within amino acid positions 70 to 85, more preferably 72 to 79 and most preferably amino acid position 76. The other modified amino acid within the beta1 domain is preferably within the α3 unit spanning amino acid positions 50 to 95, preferably within amino acid positions 50 to 65, preferably within amino acid positions 50 to 60, more preferably within amino acid positions 50 to 55 and most preferably amino acid position 53. In each case, the two amino acids are preferably selected within the respectively indicated amino acid stretches to have a distance of between 3 to 7.5 Å in the folded MHC II protein.

It is further preferred that within one MHC comprises two pairs of modified amino acids. Particularly, preferred combinations that may be combined are indicated under (i) and (ii) above for MHC I and under (iii) and (iv) above for MHC II. Thus, it is preferred that the first pair of modified amino acids comprises one amino acid that is modified in the 31 unit and one in the α1 unit of MHC I. Particularly, suitable regions within the 31 unit are within amino acid positions 12 to 32, preferably within amino acid positions 17 to 27, more preferably within amino acid positions 20 to 24 and most preferably amino acid position 22. Particularly, suitable regions within the α1 unit are within amino acid positions 61 to 81, preferably within amino acid positions 66 to 76, more preferably within amino acid positions 69 to 73 and most preferably amino acid position 71. The second pair of modified amino acids comprise one amino acid that is modified in the alpha1 domain of an MHC I and one amino acid in the alpha2 domain of an MCH I within amino acid positions 160 to 179. It is preferred that the one amino acid in the alpha1 domain is modified in the α1 unit, preferably within amino acid positions 50 to 70, more preferably within amino acid positions 50 to 60, more preferably 50 to 54 and most preferably amino acid position 51. Particularly, suitable regions for modifying the other amino acid within the alpha2 domain are within amino acid positions 165 to 178, preferably within amino acid positions 170 to 177, more preferably within amino acid positions 173 to 176 and most preferably amino acid position 175. Thus, in a particularly preferred embodiment the stabilized MHC I comprises a first pair of modified amino acids at position 22 and 71 and a second pair of modified amino acid at position 51 and at position 175.

Any of above modifications of MHC I may further be combined with a pair of modifications wherein the first modified amino acid is within amino acid positions 80 to 90, preferably within amino acid positions 82 to 86, and more preferably amino acid position 84 and the second amino acid is within amino acid positions 136 to 146, preferably within amino acid positions 137 to 141, and more preferably amino acid position 139.

It was surprising that the modification of amino acids in the above-described amino acid regions of MHC I and MHC II and at the respectively indicated positions and, thus the introduction of covalent bonds between amino acids at position which are not naturally connected by covalent bonds allows the generation of modified MHC I and MHC II molecules that: (i) are properly folded, (ii) bind peptides with high affinity and (iii) are recognized by TCR molecules with high specificity and selectivity.

The preferred modified MHC I and MHC II molecules of the second aspect can also be used in all other aspects of the present invention.

The present invention also comprises peptide binding fragments of the modified MHC I or MHC II molecules. As known in the art, MHC I and MHC II bind to peptides and are in turn bound by TCRs that interact both with the MHC I or MHC II and the peptide. However, only parts of the MHC I and MHC II molecule are required for binding to the peptide that is "presented" to the TCR. In MHC I the alpha1 and alpha2 domain fold to form a binding groove that binds the peptide and in MCH II the alpha1 and beta 1 domain form the binding groove that binds the peptide. Thus, peptide binding fragments of MHC I and MHC II, respectively, comprise at least the alpha1 and alpha2 domain or the alpha1 and beta1 domain. Accordingly, the binding fragment may lack the transmembrane domain or additionally the alpha3 domain in MHC I or the alpha2 and/or beta2 domain in MHC II. Fragments lacking at least the transmembrane domain are soluble and are particularly suitable to be used in a pharmaceutical composition, in particular in a vaccine.

In a third aspect thereof, the present invention provides a method for detecting or generating a specific amino acid binding motif for a TCR, comprising performing the method according to the first aspect thereof comprising a preselected TCR, and the additional step of determining and comparing the amino acid sequences of those peptide ligands in said peptide ligand/MHC molecule complexes for which a TCR binding was detected, thereby identifying the specific amino acid binding motif for said preselected TCR.

In a fourth aspect thereof, the present invention provides a method for detecting or determining cross-reactivity of a TCR, comprising performing the method according to the second aspect of the invention, and the additional step of determining and comparing the amino acid sequences of those peptide ligands in said peptide ligand/MHC molecule complexes for which a TCR binding was detected, thereby identifying cross-reactivity of said TCR.

In a fifth aspect thereof, the present invention provides a method for detecting or determining cross-reactivity of a TCR, comprising performing the method according to the first aspect of the invention comprising a preselected TCR, and the additional step of determining and comparing the amino acid sequences of those peptide ligands in said peptide ligand/MHC molecule complexes for which a TCR binding was detected, thereby identifying cross-reactivity of said TCR.

In a sixth aspect thereof, the methods according to the present invention can be used for screening or in vitro priming of cellular drug products. The stabilized HLA complexes bound to beads, filaments, nanoparticles or other carriers can be readily loaded with a peptide of interest mimicking antigen presenting cells, and afterwards conveniently used in combination with costimulatory molecules (e.g. anti CD28, anti 4 1BB) as "ready to use" artificial antigen presenting cells for in vitro priming and expansion.

Current methods for the large-scale generation of pMHC libraries, a high throughput binding motif determination of a high affinity TCR, and the identification and characterization of potentially cross-reactive peptides suffer from stability problems, requiring multimers to be swiftly loaded with peptides of choice without additional handling and within a short time frame (as in Luimstra et al., above), which also makes technologies like UV exchange unsuitable.

With the present technology, the inventors gain multiple advantages over the wild type molecule or other existing exchange technologies: the empty monomer can be produced in bulk way ahead of the desired experiment and pMHC generation is not restricted by any other method aside from procuring desired peptides and quick peptide loading reactions. The inventors have successfully stored the empty monomer for at least a year at −80° C. and used them with no degradation or impaired peptide receptiveness detected. The inventors have also successfully stored the resulting pMHC complexes for at least two weeks at 4° C. and reused them for affinity measurements without loss of signal. In addition to all these advantages achieved by introducing the modification, pMHC complexes generated displayed by the mutant are substantially representative of wild type complexes with respect to TCR ligand binding.

In one aspect, the invention provides a method for screening for a TCR-binding peptide ligand/MHC molecule complex for TCR-binding.

The method comprises the use of a suitably stabilized MHC molecule that comprises at least one artificially introduced covalent bridge between amino acids of the alpha1 domain and amino acids of the alpha2 domain of said stabilized MHC molecule in case of MHC I, and/or at least one artificially introduced covalent bridge between two amino acids of the alpha1 domain of said stabilized MHC molecule in case of MHC I, or at least one artificially introduced covalent bridge between amino acids of the alpha1 domain and amino acids of the beta1 domain of said stabilized MHC molecule in case of MHC II. Major histocompatibility complex class I and class II share an overall similar fold. The binding platform is composed of two domains, originating from a single heavy α-chain (HC) in the case of MHC class I and from two chains in the case of MHC class II (α-chain and β-chain). The two domains evolved to form a slightly curved R-sheet as a base and two α-helices on top, which are far enough apart to accommodate a peptide chain in-between. Hence, suitable stabilization for the method according to the present invention can be achieved for both MHC classes.

In one embodiment, the present invention involves the use of disulfide-stabilized, initially empty, MHC molecules that can be loaded by simply adding suitable peptide before the use thereof. pMHCs generated using this disulfide-modified MHC molecule are representative of the non-modified wild type variant, and are suitable for screening, e.g. high throughput binding motif determination of a high affinity TCR as well as identification and characterization of potentially cross-reactive peptides.

The empty MHCs do not substantially degrade on commonly used surfaces, like glass plates, are representative for the non-modified wild type variant when loaded with peptide, and are suitable for screening, and allow to generate pMHCs quickly, even when immobilized on a surface. In the context of the present invention, this is achieved by and understood as a "suitably stabilized" or "stabilized" pMHC.

In previous studies with the murine MHC class I molecule H-2K$^b$ introduction of a disulfide bond between opposing residues in the F-pocket by mutating a tyrosine at position 84 and an alanine at position 139 to cysteines was able to stabilize the complex. Thus, in one embodiment an artificially introduced covalent bridge between amino acids was introduced between α-helices, for example by mutating a tyrosine at position 84 and an alanine at position 139 into cysteines of MHC I. While in some cases, it may be difficult to isolate monomers without any peptide ligand, this could be efficiently overcome by adding a low affinity peptide.

The term "MHC" is an abbreviation for the phrase "major histocompatibility complex". MHC's are a set of cell surface receptors that have an essential role in establishing acquired immunity against altered natural or foreign proteins in vertebrates, which in turn determines histocompatibility within a tissue. The main function of MHC molecules is to bind to antigens derived from altered proteins or pathogens and display them on the cell surface for recognition by appropriate T-cells. The human MHC is also called HLA (human leukocyte antigen) complex or HLA. The MHC gene family is divided into three subgroups: class I, class II, and class Ill. Complexes of peptide and MHC class I are recognized by CD8-positive T-cells bearing the appropriate TCR, whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding TCRs is important in the development of cancer immunotherapies such as vaccines and cell therapies. The MHC I molecule consists of an alpha chain, also referred to as MHC I heavy chain and a beta chain, which constitutes a beta 2 microglobulin molecule. The alpha chain, interchangeably used with heavy chain in the context of the present invention, comprises three alpha domains, i.e. alpha1 domain, alpha2 domain and alpha3 domain. Alpha1 and alpha2 domain mainly contribute to forming the peptide pocket to produce a peptide ligand MHC (pMHC) complex. The alpha1 domain of a MHC I spans amino acid positions 1 to 90 and comprises as secondary structure a β-sheet spanning amino acid positions 1-49 (termed herein "β1 unit") followed by an α-helix structure spanning amino acid positions 50-84 (termed herein "α1 unit"). The alpha2 domain of a MHC I spans amino acid positions 91 to 182 and comprises as secondary structure a β-sheet spanning amino acid positions 91-135 (termed herein "β2 unit") followed by an α-helix structure spanning amino acid positions 138-179 (termed herein "α2 unit"). The beta1 domain of a MHC II is on a separate polypeptide and fulfills within MHC II the structural role of the alpha2 domain of MHC I. It spans amino acid positions 1 to 95 and comprises as secondary structure a β-sheet spanning amino acid positions 1 to 49 (termed herein "β3 unit") followed by an α-helix structure spanning amino acid positions 50 to 95 (termed "α3 unit"). Here and in each other case in which reference is made to an amino acid position in an MHC I or MHC II molecule the positions are indicated based on IGMT numbering excluding the N-terminal first signal peptide, which typically varies in length between 20 to 29 amino acids. The stabilized MHC II molecules of the present invention may comprise the alpha1 and beta1 domain on two separate polypeptides or they may be linked to each other in one polypeptide to form a single chain MHC II, e.g. the C-terminus of the alpha1 domain of an MHC II is linked to the N-terminus of the beta1 domain of an MHC II directly or via a peptide linker.

HLAs are molecules which differ between different human beings in amino acid sequence. However, HLAs can be identified by an internationally agreed nomenclature, the IMGT nomenclature, of HLA. The categorization to, e.g. HLA-A, is based on the identity of a given HLA to official reference sequences of each HLA, that were produced by sequence alignments. Thus, a given HLA sequence with the highest sequence identity to the HLA-A sequence according to SEQ ID NO: 6 will be categorized as HLA-A. The official HLA reference sequences as well as information to the categorization system are available: ebi.ac.uk/ipd/imgt/hla/nomenclature/alignments.html. The website provides the following information regarding how to categorize any given HLA sequence:

"The alignment files produced use the following nomenclature and numbering conventions. These conventions are based on the recommendations published for Human Gene Mutations. These were prepared by a nomenclature-working group looking at how to name and store sequences for human allelic variants. These recommendations can be found in Antonarakis SE and the Nomenclature Working Group Recommendations for a Nomenclature System for Human Gene Mutations Human Mutation (1998) 11 1-3.

Only alleles officially recognised by the WHO HLA Nomenclature Committee for Factors of the HLA System are included in the sequence alignments.

As recommended for all human gene mutations, a standard reference sequence should be used for all alignments. A complete list of reference sequences for each allele can be seen below.

The reference sequence will always be associated with the same (original) accession number, unless this sequence is shown to be in error.
All alleles are aligned to the reference sequences.
Naming of the sequence is based upon the published naming conventions SGE Marsh, et al. (2010) *Tissue Antigens* 2010 75:291-455."

For MHC class I proteins the following HLA reference protein sequences are indicated on Jul. 12, 2019 on the web site in each case indicating the accession number that will not change for each HLA over time:

MHC Class I Proteins

HLA-A (Acc. No. HLA00001)
(SEQ ID NO: 6)
MAVMAPRTLLLLLSGALALTQTWAGSHSMRYFFTSVSRPGRGEPRFIAVGYVDDTQF

VRFDSDAASQKMEPRAPWIEQEGPEYWDQETRNMKAHSQTDRANLGTLRGYYNQS

EDGSHTIQIMYGCDVGPDGRFLRGYRQDAYDGKDYIALNEDLRSWTAADMAAQITKR

KWEAVHAAEQRRVYLEGRCVDGLRRYLENGKETLQRTDPPKTHMTHHPISDHEATLR

CWALGFYPAEITLTWQRDGEDQTQDTELVETRPAGDGTFQKWAAVVVPSGEEQRYT

CHVQHEGLPKPLTLRWELSSQPTIPIVGIIAGLVLLGAVITGAVVAAVMWRRKSSDRKG

GSYTQAASSDSAQGSDVSLTACKV

HLA-B (Acc. No. HLA00132)
(SEQ ID NO: 7)
MLVMAPRTVLLLLSAALALTETWAGSHSMRYFYTSVSRPGRGEPRFISVGYVDDTQFV

RFDSDAASPREEPRAPWIEQEGPEYWDRNTQIYKAQAQTDRESLRNLRGYYNQSEA

GSHTLQSMYGCDVGPDGRLLRGHDQYAYDGKDYIALNEDLRSWTAADTAAQITQRK

WEAAREAEQRRAYLEGECVEWLRRYLENGKDKLERADPPKTHVTHHPISDHEATLRC

WALGFYPAEITLTWQRDGEDQTQDTELVETRPAGDRTFQKWAAVVVPSGEEQRYTC

HVQHEGLPKPLTLRWEPSSQSTVPIVGIVAGLAVLAVVVIGAVVAAVMCRRKSSGGKG

GSYSQAACSDSAQGSDVSLTA

HLA-C (Acc. No. HLA00401)
(SEQ ID NO: 8)
MRVMAPRTLILLLSGALALTETWACSHSMKYFFTSVSRPGRGEPRFISVGYVDDTQFV

RFDSDAASPRGEPRAPWVEQEGPEYWDRETQKYKRQAQTDRVSLRNLRGYYNQSE

AGSHTLQWMCGCDLGPDGRLLRGYDQYAYDGKDYIALNEDLRSWTAADTAAQITQR

KWEAAREAEQRRAYLEGTCVEWLRRYLENGKETLQRAEHPKTHVTHHPVSDHEATL

RCWALGFYPAEITLTWQWDGEDQTQDTELVETRPAGDGTFQKWAAVMVPSGEEQR

YTCHVQHEGLPEPLTLRWEPSSQPTIPIVGIVAGLAVLAVLGAVVAVVMCRRKSSG

GKGGSCSQAASSNSAQGSDESLIACKA

HLA-E (Acc. No. HLA00934)
(SEQ ID NO: 9)
MVDGTLLLLLSEALALTQTWAGSHSLKYFHTSVSRPGRGEPRFISVGYVDDTQFVRFD

NDAASPRMVPRAPWMEQEGSEYWDRETRSARDTAQIFRVNLRTLRGYYNQSEAGSH

TLQWMHGCELGPDRRFLRGYEQFAYDGKDYLTLNEDLRSWTAVDTAAQISEQKSND

ASEAEHQRAYLEDTCVEWLHKYLEKGKETLLHLEPPKTHVTHHPISDHEATLRCWALG

FYPAEITLTWQQDGEGHTQDTELVETRPAGDGTFQKWAAVVVPSGEEQRYTCHVQH

EGLPEPVTLRWKPASQPTIPIVGIIAGLVLLGSVVSGAVVAAVIWRKKSSGGKGGSYSK

AEWSDSAQGSESHSL

HLA-F (Acc. No. HLA01096)
(SEQ ID NO: 10)
MAPRSLLLLLSGALALTDTWAGSHSLRYFSTAVSRPGRGEPRYIAVEYVDDTQFLRFD

SDAAIPRMEPREPWVEQEGPQYWEWTTGYAKANAQTDRVALRNLLRRYNQSEAGSH

TLQGMNGCDMGPDGRLLRGYHQHAYDGKDYISLNEDLRSWTAADTVAQITQRFYEAE

-continued

EYAEEFRTYLEGECLELLRRYLENGKETLQRADPPKAHVAHHPISDHEATLRCWALGF

YPAEITLTWQRDGEEQTQDTELVETRPAGDGTFQKWAAVVVPSGEEQRYTCHVQHE

GLPQPLILRWEQSPQPTIPIVGIVAGLVVLGAVVTGAVVAAVMWRKKSSDRNRGSYSQ

AAV

HLA-G (Acc. No. HLA00939)
(SEQ ID NO: 11)
MVVMAPRTLFLLLSGALTLTETWAGSHSMRYFSAAVSRPGRGEPRFIAMGYVDDTQF

VRFDSDSACPRMEPRAPWVEQEGPEYWEEETRNTKAHAQTDRMNLQTLRGYYNQS

EASSHTLQWMIGCDLGSDGRLLRGYEQYAYDGKDYLALNEDLRSWTAADTAAQISKR

KCEAANVAEQRRAYLEGTCVEWLHRYLENGKEMLQRADPPKTHVTHHPVFDYEATLR

CWALGFYPAEIILTWQRDGEDQTQDVELVETRPAGDGTFQKWAAVVVPSGEEQRYTC

HVQHEGLPEPLMLRWKQSSLPTIPIMGIVAGLVVLAAVVTGAAVAAVLWRKKSSD

HLA-H (Acc. No. HLA02546)
(SEQ ID NO: 12)
MVLMAPRTLLLLLSGALALTQTWARSHSMRYFYTTMSRPGRGEPRFISVGYVDDTQF

VRFDSDAASQRMEPRAPWMEREGPEYWDRNTQICKAQAQTERENLRIALRYYNQSE

GGSHTMQVMYGCDVGPDGRFLRGYEQHAYDSKDYIALNEDLRSWTAADMAAQITKR

KWEAARQAEQLRAYLEGEFVEWLRRYLENGKETLQRADPPKTHMTHHPISDHEATLR

CWALGFYPAEITLTWQRDGEDQTHTRSSWRPGLQGMEPSRSGRLWWCLLERSRDT

PAMCSMRVCQSPSP*DGSHLPSPPSPSWASLLAWFYL*LWSLELWSLL*CGGRRAQIE

KEGATLRLQAATVPRALMCLSRRESVX

HLA-J (Acc. No. HLA02626)
(SEQ ID NO: 13)
MGSWRPEPSSCCSRGPWPWPRPGRAPTP*GISAPPFPGRAAGSPASLPWATWTTRS

SCGSTVTP*V*G*RRGRGGWSRRGRSIGTYRHWAPRPRHRLTE*TCGPCSATTTRAR

RGITSSRECLAATWGPTGVSSAGMSSMPTTARITSP*TRTCAPGPPRIPRLRLPSASM

RRPMWLSKGEPTWRAPAWSGSADTWRTGRRRCSARTPPKTHVTHPPL*T*GITRSW

VLGFYPAEITLTWQRDGEDQTQDMELVETRPTGDGTFQKWAVVVVPSGEEQRYTCH

VQHKGLPKPLILRWEPSPQPTIPIVGIIAGLVLLGAVVTGAVVTAVMWRKKSSDRKGGS

YSQAASSQSAQGSDVSLTACKV*

HLA-K (Acc. No. HLA02654)
(SEQ ID NO: 14)
MGSWRPEPSSCCSWGPWP*PRPGRVPTP*GISAPPCPGRVAGSPGTSQWATWTTR

SSCGSTATRRLRGCSRSRRGWSRRDRSIGTGAHGTSGPRTD*QE*TCPCRAATTTRA

RPGLTPSR*CMAATWGWKGASSAGMNSTPTMARIT*PGTRTCAPGPRRTWRLRSPS

ASGRQKNLQSRSGPTWRARAWRGSQTPGEREGDAAAHGPLPQTHMIHHSVSDYKA

TLRCWALGFYPVEITLAWQQDGEDQTRDMELLETRPAGDGTFQKWAAVVVPSGEEQ

RYPCHVQHEGLPKPLTLRWEQSSQPTIPIVGIVAGLVLLGAVVTGAVVSAVMCRKKNS

DRVSYSEAASSDHAQGSDVSLTACKV*

HLA-L (Acc. No. HLA02655)
(SEQ ID NO: 15)
MGVMAPRTLLLLLLGALALTETWAGSHSLRYFSTAVSQPGRGEPRFIAVGYVDDTEFV

RFDSDSVSPRMERRAPWVEQEGLEYWDQETRNAKGHAQIYRVNLRTLLRYYNQSEA

GSHTIQRKHGCDVGPTGASSAGMNSSPTMARITSP*TRTCTPGPPRTQRLRSPSTSG

KRTNTQSRSGPT*GQVHGVAPQTPGEREGDAAARGSPKGTCDPAPHL*P*GHPEVLG

PGPLPCGDHTDLAAGWGGPDPGHGACGDQACRGRNLPEVGGCSGAFRRGAEIHVP

-continued

CAA*GAARAPHPEMGAVFSAHHPHRGHRCWPVSPWSCGHWSCGCCCDVEEEKLR*

NKEELCSGCLQQLCSVL*CIS*YL*SLX

The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface. Each individual can express up to two types of HLA-A, one from each of their parents. Some individuals will inherit the same HLA-A from both parents, decreasing their individual HLA diversity. However, the majority of individuals receive two different copies of HLA-A. The same pattern follows for all HLA groups. In other words, every single person can only express either one or two of the 2432 known HLA-A alleles coding for currently 1740 active proteins. HLA-A*02 signifies a specific HLA allele, wherein the letter A signifies to which HLA gene the allele belongs to and the prefix "*02 prefix" indicates the A2 serotype. In MHC class I dependent immune reactions, peptides not only have to be able to bind to certain MHC class I molecules expressed by tumor cells, they subsequently also have to be recognized by T-cells bearing specific TCRs.

In the second step of the preferred method according to the invention, the suitably stabilized MHC molecule is contacted with a multitude of peptide ligands, in order to form peptide ligand/MHC (pMHC) molecule complexes. Using pMHC complexes as soluble analytes instead of immobilizing is preferable for quick and cost-effective high throughput screenings, since a broad variety of regeneratable biosensors capable of reversibly immobilizing bispecific TCR constructs exists.

"Contacting" in the context of the present invention shall mean that peptide(s) is (are) brought in contact with the empty and/or low affinity peptide-loaded MHC molecules in such a way that a substantial portion of the peptides form complexes (are "loaded") with said empty and/or low affinity peptide-loaded MHC molecules. As one preferred example, loading MHC complexes was performed by addition and mixing of desired peptides of at least a 100 to 1 molar ratio to the monomer solution in a suitable buffer, and a minimum of 5 minutes incubation at room temperature.

The groove in-between the two helices accommodates peptides based on (i) the formation of a set of conserved hydrogen bonds between the side-chains of the MHC molecule and the backbone of the peptide and (ii) the occupation of defined pockets by peptide side chains (anchor residues P2 or P5/6 and PC) in MHC class I and P1, P4, P6, and P9 in MHC class II). The type of interactions of individual peptide side-chains with the MHC depend on the geometry, charge distribution, and hydrophobicity of the binding groove. In MHC class I, the binding groove is closed at both ends by conserved tyrosine residues leading to a size restriction of the bound peptides to usually 8-10 residues with its C-terminal end docking into the F-pocket. In contrast, MHC class II proteins usually accommodate peptides of 13-25 residues in length in their open binding groove, with the peptide N-terminus usually extruding from the P1 pocket. It has been reported that the interactions at the F region in MHC class I and the P1 region (including the P2 site) in MHC class II appear to have a dominant effect on the presentation of stable pMHC complexes and on the immunodominance of certain peptidic epitopes. Interestingly, these pockets are located at opposite ends of the binding groove of the respective MHC class I and MHC class II structures.

The multitude of peptide ligands can comprise at least about 1,500 different MHC binding peptides, preferably at least about 5,000 different MHC binding peptides, more preferred at least about 15,000 different MHC binding peptides, and most preferred an immunopeptidome preparation with at least about 150,000 MHC binding peptides. Said peptides comprise a binding motif of 8-10 residues in length for MHC class I proteins and 13-25 residues in length for MHC class II proteins, and can be of a length of between 8 and 100, preferably of between 8 and 30, more preferred between 8 and 16 residues. Most preferred are peptides that consist of the actual binding motif.

Ligand peptides as used in the context of the present invention can be derived from polypeptides that are cancer-related, infection-related (bacterial or viral), and even immune- (e.g. autoimmune-) disease related. The term also includes suitably mutated or naturally occurring mutated ligand peptides, i.e. different from their underlying sequence as occurring in the respective polypeptide.

Preferred is the method according to the present invention, wherein said contacting comprises loading said MHC binding peptides onto the MHC at between about 4° C. to 37° C., preferably at about room temperature (15° to 25° C., preferably 20° C.).

It was surprisingly found that the loaded HLA/peptide molecules (pMHC or pMHC complex) are very stable for more than about 1 day, and preferably for more than 1 week at (e.g. more than 2 weeks) at about 4° C. This allows an effective and convenient use in many more applications than in known methods as described above.

It was also found in the context of the present invention, and somewhat in contrast to the literature as above, that the present method was clearly superior to the popular method of UV exchange using a WT pMHC molecule, allowing to perform it (in particular in a high-throughput format) on a surface, like a chip or glass slide. While the UV mediated peptide ligand exchange can generate a high number of different pMHC complexes, the exchange efficiency varies depending on the peptide and its affinity for binding to the respective MHC class I allele, resulting in different pMHC concentrations in the samples. This uncertainty is a problem for affinity measurements with pMHCs used as soluble analytes, as precise knowledge of the concentration is required to determine accurate affinities. Since the disulfide-stabilized MHC mutant is stable without peptide, this restriction does not apply. If the peptides are added at a concentration high enough to saturate the empty MHC complexes, the effective concentration of pMHC is known, significantly increasing the accuracy of the measurements and avoiding false negatives.

In the next step of the method of the present invention, said pMHC molecule complexes are screened for a TCR-binding. The binding and kinetic attributes of this interaction are parameters for protective T cell-mediated immunity, with stronger TCR-pMHC interactions showing increased interaction half-life and thus conferring superior T cell activation and responsiveness than weaker ones. The interaction strength between the TCR and pMHC ligand is typically described and measured as the dissociation constant $K_d$, an equilibrium constant that is a ratio between the on-rate constant $k_{on}$ and off-rate constant $k_{off}$ of a specific interaction. The dissociation constant $K_d$ inversely correlates with the binding strength of a specific interaction, as smaller $K_d$ values represent stronger binding.

The screening can comprise any suitable and known method for measuring and/or detecting pMHC/TCR-binding, e.g. structural TCR-pMHC affinity/avidity measurements. One example is screening of a peptide-MHC library for TCR binding by bio-layer interferometry (BLI), a special form of reflective interferometry (RI), as disclosed herein, where binding interactions for said TCR were detected stronger than a sensitivity threshold suitable for the method of $K_d$ $1.0 \times 10^{-5}$, with measured $K_d$ values ranging from $3.7 \times 10^{-9}$ to $7.2 \times 10^{-6}$, or no binding interactions for said TCR were detected when weaker than the sensitivity threshold.

Other methods involve other forms of RI, like surface plasmon resonance (SPR), or reflective interferometric spectroscopy (RIfS), or single-color reflectometry (SCORE, Biametrics, Tubingen, Germany), or marker-based assays, e.g. flow cytometric analysis with NTAmers (TCMetrix, Epalinges, Switzerland), or pMHC or TCR tetramers, or other forms of fluorescent readouts, like protein microarrays. Of course, ideally these methods can be performed in/can be readily adjusted to high-throughput formats.

In the context of the present invention, the term "about" shall mean to include +/−10% of a given value, unless otherwise noted.

The present invention as an example presents the use of disulfide-stabilized empty HLA-A*02:01 molecules which can be loaded by simply adding peptide before use. pMHCs generated using this modified MHC molecule are representative of the non-modified wild type variant and thus, demonstrate suitability for high throughput binding motif determination of a high affinity TCR as well as identification and characterization of potentially cross-reactive peptides.

Preferred is a method according to the present invention, wherein said MHC molecule is HLA, or a multimer of HLA, MHC I or MHC II, selected from the group consisting of a dimer, a trimer and a tetramer. Methods using more than one MHC molecule at once in screenings are known in the art, e.g. from Altman, et al. (in: "Phenotypic Analysis of Antigen-Specific T Lymphocytes.", Science. 4 Oct. 1996: Vol. 274, Issue 5284, pp. 94-969. Similarly, dimers or trimers can be used.

The MHC molecules as used include at least one artificially introduced covalent bridge between amino acids. This bridge is selected from a recombinantly introduced disulfide bridge, the introduction of non-natural amino acids to be crosslinked, the introduction of photo-crosslinking amino acids, and chemically introduced crosslinks. The introduction of crosslinks using cysteines is described herein, examples for dimeric cross-linking reagents are DPDPB and HBVS, and the trimeric cross-linker TMEA.

Preferred is a method according to the present invention, wherein said at least one artificially introduced covalent bridge between amino acids is introduced between α-helices, for example by i) mutating the amino acid at position 84 of MHC I, a tyrosine in the majority of HLAs (see FIG. 13) and an amino acid at position 139, a alanine in the majority of HLAs (see FIG. 13) into cysteines and/or (ii) mutating an amino acid at position 22 of MHC I, a phenylalanine in the majority of HLAs (see FIG. 13) and an amino acid at position 71 of MHC I, a serine in the majority of HLAs (see FIG. 13) and/or (iii) mutating an amino acid at position 51 of MHC I, a tryptophan in the majority of HLAs (see FIG. 13), and an amino acid at position 175 of MHC I, a glycine in the majority of HLAs (see FIG. 13), or (iv) mutating an amino acid at position 22 of MHC I, a phenylalanine in the majority of HLAs (see FIG. 13) and an amino acid at position 71 of MHC I, a serine in the majority of HLAs (see FIG. 13) and mutating an amino acid at position 51 of MHC I, a tryptophan in the majority of HLAs (see FIG. 13), and an amino acid at position 175 of MHC I, a glycine in the majority of HLAs (see FIG. 13) of MHC I (based on IGMT numbering excluding the first 24 amino acids). Molecular dynamics simulations of the α1 and α2 domain or of entire MHC-I have suggested one eminent difference between empty and peptide-bound MHC-I: in the absence of a peptide, the helical sections that flank the F-pocket region (residues 74-85 and 138-149 in the α1 and α2 helices, respectively) are significantly more mobile. It seems that bound peptides restrict the mobility of this region, and that a similar advantageous and stabilizing conformational restriction might be achieved by linking different structural features of the peptide binding pocket with a covalent bond, preferably a disulfide bond.

To determine amino acids at positions corresponding to above mentioned residues 22, 51, 71, 74-85, 138-149 and 175 in each given HLA allele the respective sequence is aligned with the above indicated reference antibodies. An example of the alignment of multiple sequences of official HLA (MHC class I) reference protein sequences and murine MHC I H2Kb protein (SEQ ID NO: 331); highlighting amino acid positions 22, 51, 71, 84, 85, 139, 140 and 175 (bold) and further regions suitable for introducing stabilizing mutations (grey) is shown in FIGS. 13A and 13B. FIGS. 13A and 13B will enable the skilled person to identify the amino acids at positions corresponding to above mentioned residues 22, 51, 71, 74-85, 138-149 and 175 in each given HLA allele.

In one preferred embodiment the MHC I molecule used in the present invention is a MHC class I HLA protein, preferably HLA-A, HLA-B, HLA-C, HLA-E, HLA-F, HLA-G, HLA-H, HLA-J, HLA-K, HLA-L. These preferred HLA proteins can be mutated in their α1 domain and α2 domain, respectively, according to the reference sequences of the IMGT nomenclature. Preferably, these HLA proteins are mutated at one or more, preferably one amino acid within position 22; at one or more, preferably one amino acid within position 51, at one or more, preferably one amino acid within position 71, at one or more, preferably one amino acid within positions 74-85, at one or more, preferably one amino acid within positions 138-149, and at one or more, preferably one amino acid within position 175. Even more preferably, one amino acid is mutated at position 84 or 85 and one amino acid is mutated at position 139 or 140. Even more preferably, one amino acid is mutated at position 22 and one amino acid is mutated at position 71. Even more preferably, one amino acid is mutated at position 22 and one amino acid is mutated at position 71 and one amino acid is mutated at position 51 and one amino acid is mutated at position 175. Preferred amino acid mutations are substitutions of one amino acid at positions 74-85 and one amino acid at positions 138-149 to cysteine. Even more preferred amino acid mutations are substitutions of one amino acid at positions 22 to cysteine. Even more preferred amino acid mutations are substitutions of one amino acid at positions 51 to cysteine. Even more preferred amino acid mutations are substitutions of one amino acid at positions 71 to cysteine. Even more preferred amino acid mutations are substitutions of one amino acid at positions 175 to cysteine.

In another preferred embodiment the HLA-A protein is selected from the group consisting of HLA-A1, HLA-A2, HLA-A3, and HLA-A11. These preferred HLA-A proteins can be mutated in their α1 domain and α2 domain, respectively, according to the reference sequences of the IMGT nomenclature. Preferably these HLA proteins can be mutated at amino acid positions 22, 51, 74-85, 138-149 and amino acid position 175. It is even more preferably that the HLA-A protein is a HLA-A*02 protein. Preferred HLA-A alleles are HLA-A*02:01; HLA-A*01:01 or HLA-A*03:01.

In another preferred embodiment the HLA-B protein is selected from the group consisting of HLA-B*07, HLA-B*08, HLA-B*15, HLA-B*35 or HLA-B*44. These preferred HLA-B proteins can be mutated in their α1 domain and α2 domain, respectively, according to the reference sequences of the IMGT nomenclature.

Preferably these HLB proteins can be mutated at amino acid positions 74-85 and amino acid positions 138-149. Preferred HLA-B alleles are HLA-B*07:02; HLA-B*08:01, HLA-B*15:01, HLA-B*35:01 or HLA-B*44:05.

In the context of the present invention, the term "TCR" shall include any proteinaceous molecule/construct that comprises a TCR-derived or TCR-like binding domain, wherein the molecule/construct is suitable for the analysis/detection of pMHC/TCR binding according to the invention as described herein. In the case of the α- and/or β-chain of a TCR, this may include a molecule where both chains remain able to form a T-cell receptor (either with a non-modified α- and/or β-chain or with a fusion protein or modified α- and/or β-chain) which exerts its biological function, in particular binding to a (specific) pMHC, and/or functional signal transduction upon peptide activation. Preferred is a method according to the present invention, wherein said TCR is selected from a native TCR, a soluble TCR molecule, a single-chain TCR, and a TCR-like molecules comprising a TCR-derived or TCR-like binding domain (e.g. derived from an antibody), such as a bispecific (bs) TCR, for example like the ones as described herein.

The methods according to the present invention in preferred embodiments allow for a parallel detection, analysis and/or screening of a much larger number of peptide ligands and/or pMHC, when compared to common technologies, including UV exchange-related methods. The collection of peptides presented to the cell surface by class I and class II human leukocyte antigen (HLA) molecules are referred to as the immunopeptidome. In May 2017, already 119,073 high-confidence HLA class I peptides and 73,465 high-confidence HLA class II peptides were reported (Shao W, Pedrioli P G A, Wolski W, et al. The SysteMHC Atlas project. *Nucleic Acids Research.* 2018; 46 (Database issue):D1237-D1247), and therefore it can be expected that the human immunopeptidome exceeds 150,000 MHC binding peptides for each of class I and II. Current methods can analyze about 700 peptides a day, so that there is a demand for "true" high throughput methods, i.e. a multitude of peptide ligands as analyzed that comprises at least about 1,500 different MHC binding peptides, preferably at least about 5,000 different MHC binding peptides, more preferred at least about 15,000 different MHC binding peptides, and most preferred a substantially complete immunopeptidome preparation with at least about 150,000 MHC binding peptides.

The inventive methods allow for immunopeptidome-wide screening for as short of a period as within a day.

In view of the number of pMHC/TCR bindings to be detected/analyzed, preferred is a method according to the present invention, wherein said method is performed as a high-throughput screening (HTS) format. In HTS, up to hundreds of thousands of experimental samples can be subjected to simultaneous testing for pMHC/TCR binding under given conditions. The samples are usually and preferably handled by laboratory robotics that automate sample preparation, handling and data analysis. HTS thus easily and reliably generates and uses large datasets to answer complex biological questions, e.g. pMHC/TCR binding kinetics and biological function as described herein.

HTS classically requires samples to be prepared in an arrayed format. If necessary, the arrayed samples can be grown either on microtiter plates in liquid, or on solid agar. The density of plates can range from 96, 192, 384, 768, 1,536, or 6,144. All these densities are multiples of 96, reflecting the original 96-well microtiter plate arranged in 8×12 with 9 mm spacing (see also, for example, Bean G J, Jaeger P A, Bahr S, Ideker T. "Development of Ultra-High-Density Screening Tools for Microbial "Omics."" PLoS ONE. 2014 Jan. 21; 9(1):e85177).

For uses relating to pMHC/TCR binding kinetics as detected/analyzed and as described herein, a solid surface, such as a chip, biosensor, glass slide or bead can be used, onto which some of the analysis reagents (e.g. either the TCR or the MHC molecule) can be suitably immobilized, e.g. spotted. For immobilization, any suitable technique can be used, e.g. by biotin streptavidin interaction. Examples of the embodiments as described here are binding assays involving binding of at least one soluble TCR(s) against at least one immobilized pMHC(s), or binding of at least one immobilized TCR(s) against at least one soluble pMHC(s).

Preferred is the method according to the present invention, wherein said TCR and/or the MHC molecule is/are not labelled or suitably labelled with a detectable marker. Respective markers are known in the art and include direct or indirect labelling with radioactive, fluorescent or chemical groups (e.g. dyes). Also, enzymatic markers or antigenic markers (for a detection with antibodies) as well as mass markers can be used. Another option is coding markers (e.g. specific nucleic acids). In case of no labelling, a detection of the binding based on changes in the physical state upon complex formation/binding can be used in order to identify binding, such as a change in mass, charge, or changes in optical properties, for example of the optical thickness of the biolayer by analyte binding, and thus of the interference pattern or reflection coefficient.

Methods to detect a binding, in particular a "specific" binding of a pMHC with a TCR are known in the art. In the present invention, preferred is a method according to the present invention, wherein $K_d$ values as well as $k_{on}$ and $k_{off}$ values can be measured for said TCR, preferably with sensitivity between $K_d$s of $1 \times 10^{-10}$ M and $1 \times 10^{-3}$ M, where sensitivity can be directed by analyte concentration.

As one preferred example, the affinity is measured using 1:2 analyte dilution series starting at 500 nM, or using $1/\sqrt{10}$ analyte dilution series starting at 500 nM. As one preferred example, the peptide ligand/MHC molecule complexes are used in parallel assay reactions having different concentrations.

In yet another important aspect of the method according to the present invention, said method further comprises the step of measuring T cell activation comprising a TCR and a TCR-binding peptide ligand/MHC molecule complex that binds said TCR. Methods to detect such T cell activation through a binding, in particular a "specific" binding of a pMHC to a TCR are known in the art. In the present invention, as an example, co-incubation assays with peptide loaded target cells, Jurkat effector cells and bs-868Z11-CD3 at six different concentrations were performed, and a correlation of measured affinity for the peptide ligands from the positional scanning library with the lowest bsTCR concentration necessary to induce 3-fold luminescence increase over background was taken as a cut-off.

Yet another important aspect of the invention is a method for detecting or generating a specific amino acid binding motif for a TCR, comprising performing the method according to the present invention as described herein, wherein a preselected TCR is chosen, for which a specific amino acid binding motif is to be detected or generated. The method comprises a) providing a suitably stabilized MHC molecule, wherein said MHC molecule comprises at least one artificially introduced covalent bridge between amino acids of the alpha1 domain and amino acids of the alpha2 domain of said stabilized MHC molecule in case of MHC I, and at least one artificially introduced covalent bridge between amino acids of the alpha1 domain and amino acids of the beta1 domain of said stabilized MHC molecule in case of MHC II, b) contacting said suitably stabilized MHC molecule with a multitude of peptide ligands thereof, to form peptide ligand/MHC (pMHC) molecule complexes, and c) screening said pMHC molecule complexes for TCR-binding using said pre-selected TCR. In an additional step, the amino acid sequences of those peptide ligands in said peptide ligand/MHC molecule complexes for which a TCR binding was detected are determined and optionally and preferably compared, resulting in identifying the specific amino acid binding motif for said preselected TCR.

One additional embodiment comprises a mutagenesis of a particular amino acid sequence after the identification thereof, and contacting said mutated peptides with a suitably stabilized MHC molecule, and screening said pMHC molecule complexes for TCR-binding with a preselected TCR to obtain an amino acid binding motif for said preselected TCR. The mutagenesis of peptides can easily be performed, for example by synthesizing mutated peptides, or chemically modifying existing amino acids in respective peptide binders. The mutagenesis can also involve adding markers or other groups to the peptide(s) in order to identify diagnostically effective binders. This aspect relates to the method according to the present invention as described herein, wherein said method steps are repeated comprising a pool of peptides consisting of modified amino acid sequences for said preselected TCR as identified. The modification can furthermore be guided by one of the known computer algorithms and/or programs used to calculate improved binding parameters based on modifications of the amino acid sequence(s).

One example thereof is the screening of a pMHC complex library, comprised of peptides created in said fashion, against a preselected TCR for TCR binding by bio-layer interferometry (BLI) as disclosed herein, where binding interactions for said TCR were detected stronger than a sensitivity threshold suitable for the method of $K_d$ $1.0 \times 10^{-5}$ M, with measured $K_d$ values ranging from $3.7 \times 10^{-9}$ M to $7.2 \times 10^{-6}$ M, or no binding interactions for said TCR were detected when weaker than the sensitivity threshold. In said embodiment the present invention shows particular improvement over existing methods, as generation of pMHC complexes with a suitably stabilized MHC molecule generates predictable amounts of pMHC, thus increasing $K_d$ measurement accuracy compared to existing methods (FIGS. 5A-5E).

In one additional embodiment, the multitude of peptide ligands is mostly composed of known peptide ligands from the immunopeptidome, as identified e.g. by mass spectrometry, wherein a preselected TCR is screened for TCR-binding to directly identify existing cross-reactive peptide ligands for said TCR. Preferred is the method according to this embodiment where the number of different peptides comprises at least about 1,500 different MHC binding peptides, preferably at least about 5,000 different MHC binding peptides that are measured in parallel.

Yet another important aspect of the invention is a method for detecting or determining cross-reactivity of a TCR, comprising performing the method for detecting or generating a specific amino acid binding motif for a TCR as described herein, and the additional step of determining and comparing the amino acid sequences of those peptide ligands in said peptide ligand/MHC molecule complexes for which a TCR binding was detected, thereby identifying cross-reactivity of said TCR. This aspect detects variants of a peptide that are recognized by a single TCR.

Yet another important aspect of the invention is a method for detecting or determining cross-reactivity of a TCR, comprising performing the method for screening for a TCR-binding peptide ligand/MHC molecule complex for TCR-binding according to the present invention as described herein comprising a preselected TCR, and the additional step of determining and comparing the amino acid sequences of those peptide ligands in said peptide ligand/MHC molecule complexes for which a TCR binding was detected, thereby identifying cross-reactivity of said TCR. This aspect also detects variants of a peptide that are recognized by a single TCR.

One example thereof is identification of a cross-reactive peptide ligand based on the amino acid binding motif, previously determined by screening a preselected TCR for TCR-binding with a mutagenesis derived pMHC complex library according to the present invention, and searching for a matching peptide ligand in a database of known or assumed peptide ligands.

Yet another important aspect of the invention is a method for detecting or determining cross-reactivity of a peptide ligand/MHC molecule complex, comprising performing the method for screening for a TCR-binding peptide ligand/MHC molecule complex for TCR-binding according to the present invention as described herein comprising a preselected pMHC, and the additional step of identifying of those TCRs for which a pMHC binding was detected, thereby identifying cross-reactivity of said TCR. This aspect detects variants of TCRs that recognize a single peptide.

In these aspects, the same methods to detect a binding of a pMHC with a preselected TCR can be used as above. Nevertheless, as the TCR binding is not necessarily required to be specific, the cut-off value and sensitivity for measuring and evaluating binding does not need to be optimal, and should be chosen as best suited under the respective circumstances, which will be comprehensible to a person of skill.

In another important aspect of the methods according to the present invention, said methods can further comprise the step of measuring T cell activation comprising a TCR and a TCR-binding peptide ligand/MHC molecule complex that binds said TCR. Methods to detect such T cell activation through a binding, in particular a "specific" binding of a pMHC to a TCR are known in the art. In the present invention, as an example, co-incubation assays with peptide loaded target cells, Jurkat effector cells and bs-868Z11-CD3 at six different concentrations were performed, and a correlation of measured affinity for the peptide ligands from the positional scanning library with the lowest bsTCR concentration necessary to induce 3-fold luminescence increase over background was taken as a cut-off.

Another important aspect of the present invention then relates to a pharmaceutical composition comprising a suitably stabilized MHC molecule, wherein said MHC molecule comprises at least one artificially introduced covalent bridge between amino acids of the alpha1 domain and amino acids of the alpha2 domain of said stabilized MHC molecule in case of MHC I, and/or at least one artificially introduced covalent bridge between two amino acids of the alpha1 domain of said stabilized MHC molecule in case of MHC I, and/or at least one artificially introduced covalent bridge between amino acids of the alpha1 domain and amino acids of the beta1 domain of said stabilized MHC molecule in case of MHC II, wherein said stabilized MHC molecule is bound to a bead, filament, nanoparticle or other suitable carrier.

In a preferred embodiment the pharmaceutical composition comprises a stabilized MHC molecule according to the second aspect of the invention as described above in the second aspect of the invention. Preferably, the stabilized MHC molecule comprised in the pharmaceutical composition does not comprise a transmembrane domain.

The pharmaceutical composition furthermore comprises suitable buffers and/or excipients. Preferably, said pharmaceutical composition according to the present invention can further comprise one or a combination of more and/or a chronological sequence of these costimulatory molecules, such as an anti CD28 or anti 41BB antibody.

Another important aspect of the present invention then relates to the use of the pharmaceutical composition according to the present invention in a method according to the invention as herein.

In one embodiment the pharmaceutical composition is comprised in a vaccine. In another embodiment the pharmaceutical composition is comprised in a vaccine for use in the manufacturing of a medicament. Preferably, the vaccine is used in the prevention of cancer. Even more preferably the vaccine elicits or triggers a subject's T cell response after administration to a subject in need thereof. Preferably, the stabilized MHC molecule comprised in the pharmaceutical composition in the vaccine does not comprise a transmembrane domain.

Another important aspect of the present invention then relates to a method for the improved personalized identification of T cell receptors, or activation of T-cells, and/or T-cell therapeutics against proliferative diseases, such as cancer, by stimulation with pMHC complexes to generate cellular drug products for a specific patient. Such stimulation can be based on pMHC complexes loaded with peptides identified by obtaining/providing a sample of cancer tissue and/or cancer cells from said patient, providing obtaining/providing a sample of normal tissue and/or cells from said patient, detecting peptides as presented in the context of MHC in said sample(s) using the XPRESIDENT® or comparable method, and determining the sequence(s) of at least one of said peptides, optionally, detecting the expression of the underlying genes of said peptides as determined, detecting the MHC presentation level/number of the peptides as detected in said sample(s), optionally comparing said MHC presentation level/number of the peptides as detected in said tumor and normal tissue and/or cell samples, screening for an optimized TCR-binding peptide ligand/MHC molecule complex, comprising a method according to the present invention. Said T-cells include those recovered directly from said patient which can be re-administered after said stimulation as cellular drug product. Said stimulation can include the use of preproduced stimulation frameworks, produced by immobilization of a suitably stabilized MHC molecule, preferably produced under clinical grade conditions (e.g. GMP), onto a carrier, for example filaments or beads, that are then loaded with peptide on demand, for example directly at the clinical site. These stimulation frameworks can also include other costimulatory molecules (e.g. anti CD28 antibodies, anti 41BB antibodies) immobilized together with the suitably stabilized MHC molecule.

In a preferred aspect of the above method said peptide, e.g. a peptide specific for a certain type of cancer or other kind of proliferative disease, is already known to the entity performing the procedure through previous identification in another patient or patients. Said peptide can thus be selected and produced quickly for a different patient bearing the same type of cancer, loaded on said stimulation framework and used to produce a cellular drug product.

In a preferred aspect of the above method, said process of activation of T-cells, and/or T-cell therapeutics recovered directly from said patient also comprises transducing the T-cells to express a tumor-specific exogenous T-cell receptor (TCR), and, optionally, suitably formulating said resulting T-cell therapeutic.

The term "T cell" refers to T lymphocytes as defined in the art and is intended to include recombinant T cells. As used herein, the terms "T-cell receptor" and "TCR" refer to a molecule found on the surface of the T cell responsible for recognizing the antigens that bind to MHC molecules, and customarily refer to a molecule capable of recognizing a peptide when presented by a MHC molecule. The molecule is a heterodimer including α and β chains (or selectively, γ and δ chains) or a TCR construct that generates signals. The TCR of the present invention is a hybrid TCR including the sequences derived from other species. For example, as mouse TCRs are more effectively expressed than human TCRs in human T cells, the TCR includes a human variable region and a murine constant region. The term also includes soluble TCR molecules, and derivatives thereof, as long as they include the complementarity determining regions (CDRs) as necessary for binding.

The XPRESIDENT® technology is described, amongst others, in WO 03/100432, WO 2005/076009, and WO 2011/128448, herewith incorporated by reference in their entireties.

In a preferred aspect of the above method, said developing improved personalized T-cell receptors, T-cells, and/or T-cell therapeutics against proliferative diseases further comprises transducing the patient's autologous (own) T-cells to express a tumor-specific exogenous T-cell receptor (TCR), and, optionally, suitably formulating said resulting T-cell therapeutics.

The present inventors demonstrate that the disulfide-modified HLA-A*02:01 molecule as an example can be readily generated as a stable and empty MHC monomer, loaded with ligand peptides after refolding, and used to generate affinity data in good agreement with data collected using wild type pMHC complexes.

Both disulfide-modified HLA-A*02:01 molecules and bispecific TCRs can be used jointly with BLI-based screenings to measure pMHC-bsTCR binding affinities, a platform with much higher throughput than surface plasmon resonance measurements presently used for these interactions in the literature. Disulfide-modified HLA-A*02:01 molecules are a piece of this platform, providing reliable yet high-throughput pMHC generation. This platform could also be useful for the analysis of other biologics if targeting pMHCs, like monoclonal antibodies or bispecifics (e.g. BITEs). The pMHC-bsTCR binding affinities correlated well with cellular assays when both were performed by the inventors with a functional bispecific T cell engager. To the inventors' knowledge, this is the first in depth analysis of the connection between pMHC-bsTCR binding affinity and the in vitro activity over a wide range of affinities. Compared to the cellular screenings, the affinity screening platform was easier to use and performed significantly quicker, therefore qualifying as an early screening tool. Due to the capability of the disulfide-modified HLA-A*02:01 molecules to predictably present even low affinity peptide ligands as pMHC complexes, the inventors can precisely measure pMHC-bsTCR binding affinities without having to account for variations encountered in exogenous peptide loading approaches, resulting in no loss of potentially valuable information. The inventors believe that the ease of use of the presented affinity analysis platform will aid the development of safe and effective T cell receptor based bispecific molecules from the early stages on.

As an example, the inventors show that it is possible to quickly generate pMHC-bsTCR binding affinity datasets and extrapolate cross-reactivity search motifs from them. Guided by the inventor's HLA peptidomics-based XPRESIDENT® platform, the search motifs can be used to identify potentially cross-reactive peptide ligands. In the presented execution of this strategy, the inventors were able to identify a large number of peptides strongly recognized by the bsTCR and capable of inducing T cell activation, with sequence consensus compared to the original target as low as one out of nine positions.

This exciting innovative technology could even lead to screenings of the entire discovered immunopeptidome: pMHC libraries of such dimensions are currently only available by yeast display using randomly mutated single-chain peptide MHC libraries (32, 33). While useful for broad TCR analysis, they are far more complicated in use and of less predictable peptide ligand composition compared to the peptide microarrays typically used in antibody development. Due to its stability and low-effort peptide loading process, the disulfide-modified HLA-A*02:01 molecules of the present invention may be the ideal fit for the creation of pMHC microarrays with high complexity in the future, for example by combining large scale coating of empty MHCs and the high-throughput of modern peptide microarray inkjet printers.

Major histocompatibility complex (MHC) class I molecules present short peptide ligands on the cell surface for interrogation by cytotoxic CD8+ T cells. MHC class I complexes presenting tumor-associated peptides (TUMAPs) are key targets of cancer immunotherapy approaches currently in development, making them important for efficacy as well as safety screenings. Without peptide ligand, MHC class I complexes are unstable and decay quickly, making the production of soluble monomers for analytical purposes labor intensive. The inventors have developed a disulfide bond stabilized HLA-A*02:01 molecules that are stable without peptide but can form peptide-MHC complexes with ligands of choice within minutes. The inventors illustrate the concurrence between the engineered mutants and the wild type variant with respect to the binding affinity of wild type or maturated high affinity TCRs. The inventors demonstrate their potential as analytes in high throughput affinity screenings of bispecific TCR molecules and generate a comprehensive TCR binding motif to identify off-target interactions.

Another aspect of the invention relates to nucleic acids encoding the stabilized MHC molecules or peptide binding fragments thereof of the second aspect of the invention and vectors. It is well known in the art that MHC I comprises all peptide binding domains, i.e. the alpha1 domain and alpha2 domain on one polypeptide chain whereas MHC II naturally comprises the alpha1 domain and the beta1 domain on two polypeptide chains. As previously noted a functional MHC II can also be provided on a single peptide by fusing the beta1 domain to the alpha1 domain. Accordingly, the nucleic acid encoding the MHC I and II of the invention may encode one or two polypeptides or the two polypeptides may also be encoded by two separate nucleic acids.

The term "nucleic acid" refers in the context of this invention to single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Another aspect of the invention is a vector comprising the nuclei acid(s) encoding the stabilized MHC molecules or peptide binding fragments thereof of the second aspect of the invention. Such vectors may be used in vaccination strategies in which expression of the vaccine in the patient is desired. In such cases the vector may additionally encode the protein or T-cell epitope comprising fragments thereof, to which an immune response, preferably a T-cell response is desired. In this way it may be ascertained that the peptide binding pocket of the MHC molecule expressed in cells of the patient that comprise the vector is loaded with the correct peptide. Alternatively, the MHC molecule may be modified to comprise the peptide comprising the T-cell epitope in a fusion protein. Typically, the peptide will be fused to the MHC molecule with an intervening peptide linker to allow the peptide to be bound by the binding groove of the MCH molecule.

The term "vector" refers in the context of this invention to a polynucleotide that encodes a protein of interest or a mixture comprising polypeptide(s) and a polynucleotide that encodes a protein of interest, which is capable of being introduced or of introducing proteins and/or nucleic acids comprised therein into a cell. Examples of vectors include but are not limited to plasmids, cosmids, phages, viruses or artificial chromosomes. A vector is used to introduce a gene product of interest, such as e.g. foreign or heterologous DNA into a host cell. Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized. Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, as long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, e.g. pUC, pcDNA, pBR.

In summary, the invention relates to the following items.

Item 1. A method for screening for a TCR-binding peptide ligand/MHC molecule complex, comprising the steps of: a) providing a suitably stabilized MHC molecule, wherein said MHC molecule comprises at least one artificially introduced covalent bridge between amino acids of the alpha1 domain and amino acids of the alpha2 domain of said stabilized MHC molecule in case of MHC I, and at least one artificially introduced covalent bridge between amino acids of the alpha1 domain and amino acids of the beta1 domain of said stabilized MHC molecule in case of MHC II, b) contacting said suitably stabilized MHC molecule with a multitude of peptide ligands thereof, to form peptide ligand/MHC (pMHC) molecule complexes, and c) screening said pMHC molecule complexes for TCR-binding.

Item 2. The method according to Item 1, wherein said MHC molecule is HLA, or a multimer of HLA, MHC I or MHC II, selected from the group consisting of a dimer, a trimer and a tetramer.

Item 3. The method according to Item 1 or 2, wherein said at least one artificially introduced covalent bridge between amino acids is selected from a recombinantly introduced disulfide bridge, the introduction of non-natural amino acids to be crosslinked, the introduction of photo-crosslinking amino acids, and chemically introduced crosslinks.

Item 4. The method according to any one of Items 1 to 3, wherein said at least one artificially introduced covalent bridge between amino acids is introduced between α-helices, for example by mutating a tyrosine at position 84 and an alanine at position 139 into cysteines of MHC I.

Item 5. The method according to any one of Items 1 to 4, wherein said multitude of peptide ligands comprises at least about 1,500 different MHC binding peptides, preferably at least about 5,000 different MHC binding peptides, more preferred at least about 15,000 different MHC binding peptides, and most preferred an immunopeptidome preparation with at least about 150,000 MHC binding peptides.

Item 6. The method according to any one of Items 1 to 5, wherein said contacting comprises loading said MHC binding peptides at between about 4° C. to 30° C., preferably at about room temperature.

Item 7. The method according to any one of Items 1 to 6, wherein said loaded HLA/peptide molecules are stable for more than about 1 day, and preferably for more than 1 week at about 4° C.

Item 8. The method according to any one of Items 1 to 7, wherein the sensitivity level for affinity screening of a TCR for binding to pMHC complexes is higher than about $K_d$ $1.0 \times 10^{-9}$, preferably higher than about $K_d$ $1.0 \times 10^{-6}$ M, and more preferred higher than about $K_d$ $1.0 \times 10^{-3}$ M.

Item 9. The method according to any one of items 1 to 8, wherein said TCR is selected from a native TCR, a soluble TCR molecule, and a TCR-like molecule, such as a bs TCR.

Item 10. The method according to any one of items 1 to 9, wherein either the TCR or the MHC molecule is suitably immobilized on a solid surface, such as a chip, biosensor, glass slide or bead.

Item 11. The method according to any one of items 1 to 10, wherein said TCR and/or the MHC molecule is/are label and/or marker-free.

Item 12. The method according to any one of items 1 to 11, wherein said method is performed as a high-throughput screening format.

Item 13. A method for detecting or generating a specific amino acid binding motif for a TCR, comprising performing the method according to any one of items 1 to 12 comprising a preselected TCR, and the additional step of determining and comparing the amino acid sequences of those peptide ligands in said peptide ligand/MHC molecule complexes for which a TCR binding was detected, thereby identifying the specific amino acid binding motif for said preselected TCR.

Item 14. The method according to item 13, wherein said peptide ligand/MHC molecule complexes are used in parallel assay reactions having different concentrations.

Item 15. The method according to item 13 or 14, wherein said method steps are repeated comprising a pool of peptides consisting of modified amino acid binding motifs for said preselected TCR as identified.

Item 16. A method for detecting or determining cross-reactivity of a TCR, comprising performing the method according to item 15, and the additional step of determining and comparing the amino acid sequences of those peptide ligands in said peptide ligand/MHC molecule complexes for which a TCR binding was detected, thereby identifying cross-reactivity of said TCR.

Item 17. A method for detecting or determining cross-reactivity of a TCR, comprising performing the method according to any one of items 1 to 12 comprising a preselected TCR, and the additional step of determining and comparing the amino acid sequences of those peptide ligands in said peptide ligand/MHC molecule complexes for which a TCR binding was detected, thereby identifying cross-reactivity of said TCR.

Item 18. The method according to any one of items 1 to 17, further comprising the step of measuring T cell activation comprising a TCR and a TCR-binding peptide ligand/MHC molecule complex that binds said TCR.

Item 19. A method for activating and/or stimulating and/or expanding a cell population (e.g. specific T cell population) with a peptide ligand/MHC molecule complex carrying stimulation framework, where said framework compromises a peptide ligand/MHC molecule complex immobilized on a carrier, e.g. beads, filaments, nanoparticles, or any carrier capable of carrying said complex, where a suitably stabilized MHC complex can be immobilized onto the carrier and the framework stored in such a state for a prolonged time prior to addition of the peptide ligand, thus significantly increasing the practicability of such a stimulation framework mimicking antigen presenting cells in research or clinical practices.

Item 20. A pharmaceutical composition comprising a suitably stabilized MHC molecule, wherein said MHC molecule comprises at least one artificially introduced covalent bridge between amino acids of the alpha1 domain and amino acids of the alpha2 domain of said stabilized MHC molecule in case of MHC I, and at least one artificially introduced covalent bridge between amino acids of the alpha1 domain and amino acids of the beta1 domain of said stabilized MHC molecule in case of MHC II, wherein said stabilized MHC molecule is bound to a bead, filament, nanoparticle or other suitable carrier.

Item 21. The pharmaceutical composition according to item 20, further comprising one or a combination of more costimulatory molecules and/or a chronological sequence of these costimulatory molecules, such as, for example, an anti CD28 antibody or anti 41BB antibody.

Item 22. The pharmaceutical composition according to item 20 or 21, wherein said stabilized MHC molecule can be stored for a prolonged time prior to addition of the peptide ligand, e.g. at room temperature or 4° C. or about −80° C.

Item 23. Use of the pharmaceutical composition according to any one of items 20 to 22 in a method according to any of items 1 to 19.

The present invention will now be further described in the examples with reference to the accompanying figures, nevertheless, without wanting to be limited thereto. For the purposes of the present invention, all references as cited are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 2A) Binding curve of the 1G4 TCR against immobilized ESO 9V Y84C/A139C HLA-A*02:01 pMHC. (FIG. 2B) Binding curve of the 1G4 TCR against immobilized ESO 9V WT-A*02:01 pMHC. (FIG. 2C) Binding curve of the 1G4 TCR against immobilized empty Y84C/A139C HLA-A*02:01. (FIG. 2D) Binding curve of the 1G4 TCR against immobilized SL9 Y84C/A139C HLA-A*02:01 pMHC.

(FIG. 3A) Binding curve of bs-868Z11-CD3 against immobilized SL9 Y84C/A139C HLA-A*02:01 pMHC. Raw data is shown in FIGS. 3A and 3B, curve fittings in FIGS. 3C and 3D. Measured using 1:2 analyte dilution series starting at 500 nM. (FIG. 3B) Binding curve of bs-868Z11-CD3 against immobilized SL9 WT-A*02:01 pMHC. Raw data is displayed in black, curve fittings in red. Measured using 1:2 analyte dilution series starting at 500 nM. (FIG. 3C) Binding curve of bs-868Z11-CD3 against immobilized empty Y84C/A139C HLA-A*02:01. Measured using 1:2 analyte dilution series starting at 500 nM. (FIG. 3D) Correlation between affinities measured using Y84C/A139C HLA-A*02:01 pMHCs or WT-A*02:01 pMHC complexes generated using UV-exchange. $K_d$s were plotted for 140 different peptide ligands generated using both methods and measured during successive experiments with good curve fittings. $K_d$s were fitted using 500 nM and 158 nM analyte concentrations. $R^2$ is the calculated correlation coefficient, dashed line represents optimal ratio.

(FIG. 4A) Heat map of affinities depending on the amino acid introduced and the exchanged position in the peptide sequence. White squares indicate wild type peptide amino acid. (FIG. 4B) Visualization of the binding motif as seq2logo graph. Size of individual letters inversely represents measured affinity for the respective amino acid at this position, calculated using the inverse $K_d$ value divided by $10^8$ and the PSSM-Logo algorithm. (FIG. 4C) Binding curve of bs-868Z11-CD3 bsTCR against ALYNVLAKV (SEQ ID NO: 1) loaded Y84C/A139C HLA-A*02:01 pMHC. Measured using $1/\sqrt{10}$ analyte dilution series starting at 500 nM.

(FIG. 5A) Measured fold-induction above background for Jurkat cells stimulated at different concentrations of bs-868Z11-CD3 in presence of SL9 wild type peptide loaded T2 target cells. (FIG. 5B) Correlation of measured affinity for the peptide ligands from the positional scanning library with the lowest bsTCR concentration necessary to induce 3-fold luminescence increase over background. Peptides are grouped into 9 different groups depending on the location of the exchange in the wild type sequence. (FIG. 5C) Correlation of measured affinity for the peptide ligands from the positional scanning library with their NetMHC predicted pMHC binding rank. Peptides are grouped into 6 different groups depending on the lowest bsTCR concentration necessary to induce 3-fold luminescence increase over background. (FIG. 5D) Correlation of measured affinities for the cross-reactive peptide ligand candidates with the lowest bsTCR concentration necessary to induce 3-fold luminescence increase over background. (FIG. 5E) Measured fold-induction above background for Jurkat cells stimulated at different concentrations of bs-868Z11-CD3 in presence of ALYNVLAKV (SEQ ID NO: 1) peptide loaded T2 target cells. Error bars represent biological triplicates.

(FIG. 10A) Left axis: pMHC concentration after UV exchange with 25000 ng/ml of UV-sensitive pMHC monomer determined using an anti-β2m ELISA. Dotted line represents ELISA/UV exchange background signal based on an UV exchange without peptide. Error bars represent technical triplicates. Right axis: Ratio of binding responses of soluble pMHC analytes to immobilized bs-868Z11-CD3 on Octet RED384 system. pMHCs were either prepared using UV exchange or by Y84C/A139C HLA-A*02:01 peptide loading. Ratios calculated by dividing UV-A*02:01 response by the Y84C/A139C HLA-A*02:01 response after 60 s of association with similarly loaded anti-F(ab) biosensors. (FIG. 10B) Detailed curve fittings for four peptides with NetMHC ranks 15 and larger. Y84C/A139C HLA-A*02:01 complexes left, WT-A*02:01 complexes right. All measurements were performed using 1:2 analyte dilution series starting at 500 nM.

FIGS. 13A and 13B show a multiple sequence alignment of various HLA alleles and one murine allele. In the sequence alignment the areas for introducing stabilizing amino acids substitutions are highlighted. This alignment provides the skilled person with a basis to determine in each given HLA allele the amino acids to be substituted in order to stabilize the MHC molecule.

Figures 1A, 1B:
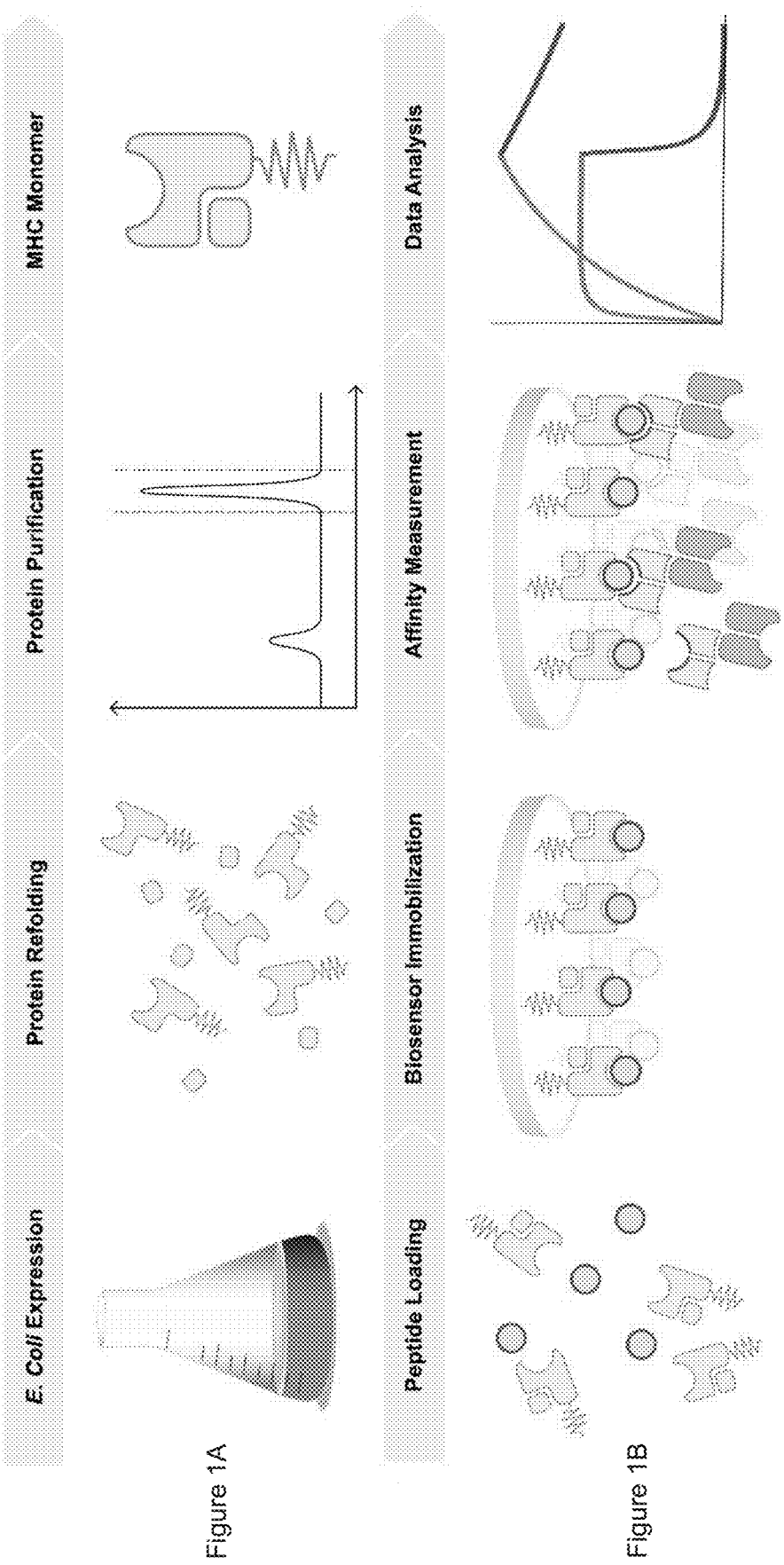
FIG. 1 shows an overview of disulfide-stabilized HLA-A*02:01 production and use for affinity measurements. (a) Expression plasmids of heavy chain and $\beta_2$m are transfected into *E. coli* and proteins of interest expressed in inclusion bodies. HLA monomers are purified using size exclusion. (b) Empty disulfide modified HLA-A*02:01 molecules can be loaded with peptide ligands by incubation at room temperature. For affinity measurements, they are immobilized onto functionalized biosensors, e.g. by biotin streptavidin interaction, and used to record association and dissociation of TCRs or TCR-like molecules.

SEQ ID NOs 1 to 5 and 16 to 325 show peptide sequences as used in the examples, below.

EXAMPLES

1. Peptide Synthesis

All peptides were generated in house using standard Fmoc chemistry with a Syro II peptide synthesizer. Peptides were subsequently analyzed using HPLC and had an average purity of 74%. UV-light sensitive peptides contained a light-sensitive building block with a 2-nitrophenylamino acid residue. The dipeptide GM was procured from Bachem. Before use peptides were solved in DMSO (Sigma, Cat. Nr. 41640), 0.5% TFA (Sigma, Cat. Nr. T6508) at concentrations ranging from 2 mg/ml to 10 mg/ml depending on the desired use case.

2. Generation of MHC Complexes by Refolding and Purification

Recombinant HLA-A*02:01 wild type (WT-A*02:01, SEQ ID NO: 322) or disulfide modified HLA-A*02:01 heavy chains with C-terminal BirA signal sequences and human β2m light chain were produced in *Escherichia coli* as inclusion bodies and purified as previously described (2). HLA-A*02:01 complex refolding reactions were performed as previously described with minor modifications (Saini et al 2013). In brief, WT-A*02:01 or disulfide-modified HLA-A*02:01 heavy chains, β$_2$m light chain and peptide were diluted in refolding buffer (100 mM Tris-Cl pH 8, 0.5 M arginine, 2 mM EDTA, 0.5 mM oxidized glutathione, 5 mM reduced glutathione) and incubated for 2 to 8 days at 4° C. while stirring before concentration. The concentrated protein was purified by size exclusion chromatography (SEC) in 20 mM Tris-HCl, pH 8/150 mM NaCl on an ÄKTAprime system (GE Healthcare) using a HiLoad 26/600 200 pg column (GE Healthcare). Peak fraction was either concentrated directly to 2000 µg/ml, aliquoted and frozen at −80° C. or biotinylated by BirA biotin-protein ligase (Avidity) overnight at 4° C. according to the manufacturer's instructions and subjected to a second gel-filtration before final concentration to 2000 µg/ml, aliquotation and storage at −80° C.

To produce HLA-A*02:01 wild type peptide-MHC complexes 9mer (full length) peptides or UV-light sensitive 9mer peptides (full length) were added to the refolding buffer at a concentration of 30 µM. To produce empty Y84C/A139C HLA-A*02:01 (SEQ ID NO: 323) complexes the dipeptide GM was added to the refolding buffer at a concentration of 10 mM. To produce F22C/S71C HLA-A*02:01 (SEQ ID NO: 324) complexes no peptide was added to the refolding buffer. To produce F22C/S71C W51C/G175C HLA-A*02:01 (SEQ ID NO: 325) complexes no peptide was added to the refolding buffer.

TABLE 1

| | Refolding Method | | |
|---|---|---|---|
| | Full Length Peptide | Dipeptide | Without Peptide |
| HLA-A*02:01 wild type (SEQ ID NO: 322) | + | − | − |
| HLA-A*02:01 84/139 (SEQ ID NO: 323) | + | + | − |
| HLA-A*02:01 22/71 (SEQ ID NO: 324) | n.d. | n.d. | + |
| HLA-A*02:01 22/71 51/175 (SEQ ID NO: 325) | n.d. | n.d. | + |

+: Protein is refoldable;
−: protein is not refoldable.

Table 1 below shows the refolding methods of the different disulfide-modified HLA-A*02:01 molecules and the WT-A*02:01 molecule:

3. Generation of Peptide Exchanged HLA-A*02:01 pMHC Complexes Using UV Mediated Peptide Ligand Exchange or Empty Disulfide-Modified HLA-A*02:01 Molecules Peptide exchange reactions with UV-light cleavable peptides were performed as previously described. In short desired nonamer peptides were mixed with biotinylated UV light-sensitive pMHC complexes at 100 to 1 molar ratio and subjected to at least 30 minutes of 366 nm UV light (Camag).

Peptide loading reactions with empty disulfide-modified HLA-A*02:01 MHC complexes were performed by addition and mixing of desired peptides of at least a 100 to 1 molar ratio to the monomer solution and 5-minute incubation at room temperature.

4. Soluble TCR Production

Soluble TCRs were produced as previously described (20). In short TCR alpha and TCR beta chain constructs were expressed separately in *Escherichia coli* as inclusion bodies and purified. TCR alpha chains are mutated at position 48 by replacing a threonine with a cysteine and TCR beta chains at position 57 by replacing a serine with a cysteine to form an inter-chain disulfide bond.

5. bsTCR Design and Production

The bs-868Z11-CD3 molecule was generated by linking the scTv 868Z11 to the C-terminus of the F(ab')-domain of a humanized antiCD3-antibody (22, 23). To this end the V$_β$-domain of the scTv was directly fused to the upper CH2-region derived from human IgG2 (APPVAG, SEQ ID NO: 2). Cysteine-knock-outs $C_{226}$S and $C_{229}$S within the hinge prevent the formation of F(ab)$_2$ molecules. HCMV-driven expression vectors coding either for the construct described above or the light chain of the humanized antiCD3-antibody were transiently co-transfected in EXPICHO cells (Thermo). After 12 days supernatant was processed by tandem chromatography (protein L followed by preparative size exclusion, GE Biosciences) and highly pure monomeric bsTCR was formulated in PBS

6. OctetRED Based Bio-Layer Interferometry Kinetic Affinity Measurements

The affinity of sTCR or bsTCR molecules for different pMHC complexes was measured on an OctetRED 384 system (Pall Fortebio) using kinetic or steady state binding analysis. All analytes or ligands were diluted to their final concentration in kinetics buffer (PBS, 0.1% BSA, 0.05% TWEEN 20) if not specified otherwise. All biosensors were hydrated for at least 10 minutes in kinetics buffer before use. Loadings and measurements were performed in 384 tilted well plates (Pall Fortebio) with at least 40 µl at a 3 mm sensor offset. Plate temperature was set at 25° C. and shaker speed at 1000 rpm. To allow inter-step correction baselines before association phases and the following dissociation phase were performed in the same well. Kinetics buffer was used as dissociation buffer with DMSO at an appropriate concentration added if necessary to match the analyte composition.

In the case of pMHC immobilization dip and read streptavidin (SA; Pall Fortebio Cat. Nr. 18-5021) biosensors were used to immobilize biotinylated pMHC monomers at a presumed concentration of 25 µg/ml for 60 seconds followed by a 60 seconds baseline and association and dissociation phases of 60 seconds each if not specified otherwise.

In the case of bsTCR immobilization dip and read anti-human Fab-CH1 $2^{nd}$ generation (FAB2G; Pall Fortebio Cat. Nr. 18-5127) biosensors were used to immobilize bsTCR molecules at a concentration of 100 µg/ml for 60 seconds, followed by a 15 seconds baseline and association and dissociation phases of 60 seconds each if not specified otherwise. FAB2G biosensor were regenerated up to 4 times by incubating the loaded biosensors for 5 seconds each in 10 mM Glycine pH1.5 and kinetics buffer consecutively for three times. FAB2G were also pre-conditioned that way before their first ligand immobilization.

All sensorgrams were analyzed using the OctetRED software "Data Analysis HT" version 10.0.3.7 (Pall Fortebio). Raw sensor data was aligned at the Y axis by aligning the data to the end of the baseline step and inter-step correction was used to align the start of the dissociation to the end of the association phase. No Savitzky-Golay filtering was applied. Resulting sensorgrams were then fitted using a 1:1 Langmuir kinetics binding model.

7. Cell Lines

The TAP-deficient HLA-A*02:01 expressing cell line T2 was procured from ATCC (CRL-1992) and cultured in RPMI Medium 1640 GLUTAMAX (Thermo Fisher, Cat. Nr. 61870010) Supplemented with 10% heat inactivated FCS (Life Technologies, Cat. Nr. 10270106) and the antibiotics penicillin and streptomycin (Biozym, Cat. Nr. 882082, 100 µg ml$^{-1}$ each) up until passage number 16 if necessary. The GLORESPONSE NFAT-luc2 Jurkat cell line was procured from Promega (Cat. Nr. CS1764) at passage number 6 and cultured in RPMI Medium 1640 GLUTAMAX (Thermo Fisher, Cat. Nr. 61870010) supplemented with 10% heat inactivated FCS (Life Technologies, Cat. Nr. 10270106), 1% Sodium Pyruvate (C.C.Pro, Cat. Nr. Z-20M) and the antibiotics hygromycin B (Merck Millipore, Cat. Nr. 400052, 200 µg/ml), penicillin and streptomycin (Biozym, Cat. Nr. 882082, 100 µg/ml each) up until passage number 14, if necessary.

8. T Cell Activation Assay

T cell activation assays using GloResponse™ NFAT-luc2 Jurkat cells and peptide loaded T2 target cells were performed according to manufacturer instructions. In short, T2 cells were harvested from continuous cell culture, washed and resuspended in T2 culture medium at a concentration of $3.3 \times 10^6$ cells/ml and transferred to 96 well round bottom plates (Corning Costar®, Cat. Nr. 3799). Peptide in DMSO, 0.5% TFA was added to a final concentration of 100 nM and the suspension incubated for 2 to 3 hours at 37° C., 5% $CO_2$. bsTCR formulated in PBS was diluted in T2 culture medium to desired concentration and 25 µl of the respective dilution was distributed to white 96 well flat bottom plates (Brand, Cat. Nr. 781965). GloResponse™ NFAT-luc2 Jurkat cells were harvested from continuous cell culture, washed and resuspended in T2 culture medium at a concentration of $3.0 \times 10^6$ cells ml$^{-1}$ and 25 µl of the cell suspension was distributed to the white 96 well flat bottom plates with bsTCR dilutions. After peptide loading T2 cells were resuspended and 25 µl distributed to the white 96 well flat bottom plates with bsTCR dilutions and GloResponse™ NFAT-luc2 Jurkat cells for a final effector to target ratio of 1:1 (75.000 cells each). Fully assembled plates were mixed for 5 minutes at 300 rpm on a plate shaker and the incubated for 18 to 20 h at 37° C., 5% $CO_2$. After the incubation period 75 µl of Bio-Glo™ luciferase reagent was added to each well and the plates incubated for minutes at 300 rpm on a plate shaker in the dark before reading luminescence at a 0.5 second integration time with a Synergy2 plate reader (Biotek). Luminescence as measured in relative light units (RLU) was converted to fold induction for each well by dividing measured RLU through those of control wells.

9. Crystallization and Imaging

The Y84C/A139C HLA-A*02:01-SLLMWITQV (SEQ ID NO: 4) complex and the 1G4 TCR were concentrated and mixed in a 1:1 ratio to achieve a concentration of 7 mg/ml for crystallization. A sitting drop vapor diffusion experiment resulted in crystals in the presence of a mother liquor containing 0.1 M ammonium acetate, 0.1 M bis-tris (pH 5.5), and 17% polyethylene glycol (PEG) 10,000. A single crystal was transferred to a cryoprotectant solution containing 0.1 M ammonium acetate, 0.1 M bis-tris (pH 5.5), 20% (w/v) PEG 10,000, and 10% glycerol. The crystal was mounted and cryocooled at 100 K on the EMBL P14 beamline at Deutsche Elektronen-Synchrotron containing an EIGER 16M detector. An x-ray dataset was collected to a resolution of 2.5 Å (Table 2).

TABLE 2

| Data collection and refinement statistics 1G4/Y84C/A139C HLA-A*02:01/SLLMWITQV | |
|---|---|
| | 1G4/Y84C/A139C HLA-A*02:01/SLLMWITQV |
| Data collection | |
| Space group | P2$_1$ |
| Cell dimensions | |
| a, b, c (Å) | 75.44, 53.67, 121.74 |
| α, β, γ (°) | 90.0 98.0 90.0 |
| Resolution (Å) | 2.50 (2.60-2.50)* |
| R$_{pim}$ | 0.037 (0.69) |
| I/σI | 9.6 (1.1) |
| CC (1/2) | 100.0 (0.68) |
| Completeness (%) | 99.3 (99.1) |
| Redundancy | 4.8 (5.0) |
| Refinement | |
| Resolution (Å) | 30-2.50 |
| No. reflections | 33552 |
| R$_{work}$/R$_{free}$ | 0.229 (0.273) |

TABLE 2-continued

Data collection and refinement statistics 1G4/Y84C/A139C
HLA-A*02:01/SLLMWITQV

| | 1G4/Y84C/A139C HLA-A*02:01/SLLMWITQV |
|---|---|
| No. atoms | |
| Protein | 3180 |
| Ligand/ion | 19 |
| Water | 589 |
| B-factors | |
| Protein | 98.1 |
| Ligand/ion | 97.8 |
| Water | 66.2 |
| R.m.s. deviations | |
| Bond lengths (Å) | 0.002 |
| Bond angles (°) | 0.47 |

The data were processed with XDS and scaled with AIMLESS (35, 36). Molecular replacement was performed using MOLREP with the coordinates of the TCR portion of the native complex first, followed by the pMHC [Protein Data Bank (PDB) 2BNR], and the structure was refined with REFMAC5 (37, 38). The engineered disulfide bond was manually built with Coot (39). The structure was refined to an R factor of 22.9% ($R_{free}$ of 27.3%). MolProbity was used to validate the geometry and indicated that 93.9% of the residues were in the allowed regions of the Ramachandran plot [with one glycine residue (Gly143) in the disallowed regions] (40).

10. Motif-Based Identification of Potentially Cross-Reactive Peptide Ligands Searches for nonamer peptide ligands matching one of the potential combinations allowed by the search motif were performed using the NCBI human protein database. This database covers all nonredundant GenBank CDS translations, as well as records from PDB, SwissProt, PIR, and PRF but excluding environmental samples from the whole-genome shotgun projects. The database was directly acquired from the NCBI servers.

11. Seq2Logo Generation

Seq2Logos visualizing the binding motif were created by taking the inverse value of measured $K_d$ values for the respective interaction and dividing them by $10^8$. These values were assembled in the form of a position-specific scoring matrix file and processed using the PSSM-Logo type at the Seq2Logo online resource of the Denmark Technical University Bioinformatics department (27).

12. Peptide Binding Measured by Fluorescence Anisotropy

Peptide binding was evaluated in fluorescence anisotropy assay with 300 nM of purified refolded Y84C/A139C HLA-A*02:01. 100 nM of the fluorescently labeled high-affinity peptide NLVPK$_{FITC}$VATV (Genecast) was added to the folded Y84C/A139C HLA-A*02:01 and kinetic measurements were performed with Tecan Infinite M1000 PRO (Tecan, Crailsheim, Germany) multimode plate reader measuring anisotropy (FITC $\lambda_{ex}$=494 nm, $\lambda_{em}$=517 nm). Y84C/A139C HLA-A*02:01 were either used directly after refolding or preserved at −80° C. in storage buffer (10% Glycerol, 50 mM Tris-HCL, pH 8.0) for the indicated amount of time before measurement. The kinetic measurements were performed at room temperature (22-24° C.) in 50 mM HEPES buffer, pH 7.5. Data was plotted using GraphPad Prism v7.

13. Anti-Beta-2 Microglobulin ELISA

Streptavidin (Molecular Probes, Cat. Nr. S888) at a final concentration of 2 μg/ml in PBS was added to Nunc MAX-Isorp plates (Thermo Fisher, Cat. Nr. 439454) and sealed plates incubated over night at room temperature in a damp environment. The following day plates were washed 4 times with washing buffer (PBS, 0.05% TWEEN-20) using a ELx405 plate washer (Biotek). 300 μl blocking buffer (PBS with 2% BSA) was added to each well and sealed plates incubated at 37° C. for 1 hour. Blocking buffer was discarded before adding 100 μl of a 1:100 dilution in blocking buffer of the respective UV exchange pMHC preparation. A standard series ranging from 500 ng/ml to 15.6 ng/ml based on a conventionally refolded pMHC monomer was included on each plate. Edge wells were filled with 300 μl blocking buffer to reduce edge effects and sealed plates were incubated at 37° C. for 1 hour. Plates were again washed 4 times before adding 100 μl anti-beta 2 microglobulin HRP conjugated secondary antibody (Acris, Cat. Nr. R1065HRP) at a final concentration of 1 μg/ml to each well. Sealed plates were incubated at 37° C. for 1 hour. Plates were washed again 4 times with washing buffer before adding 100 μl of room temperature TMB substrate (Sigma, Cat. Nr. T0440) to each well. Plates were incubated for 5 minutes at room temperature before stopping by adding 50 μl 1N $H_2SO_4$ to each well. Plates were immediately analyzed by reading absorbance at 450 nm for 5 seconds using a Synergy2 plate reader. pMHC concentration was calculated based on standard curve fitting (Log(Y)=A*Log(X)+B) using the Synergy2 software. Data was plotted using GraphPad Prism v7.

14. Flow Cytometric T2 Peptide Binding Assay

The TAP-deficient HLA-A*02:01-expressing cell line T2 was procured from ATCC (CRL-1992) and cultured in RPMI Medium 1640 GLUTAMAX (Thermo Fisher, Cat. Nr. 61870010) Supplemented with 10% heat inactivated FCS (Life Technologies, Cat. Nr. 10270106) and the antibiotics penicillin and streptomycin (Biozym, Cat. Nr. 882082, 100 μg/ml each) up until passage number 16 if necessary. T2 cells were harvested from continuous cell culture, washed and resuspended in T2 culture medium at a concentration of 3.3×10$^6$ cells/ml and transferred to 96 well round bottom plates (Corning Costar®, Cat. Nr. 3799). Peptide in DMSO, 0.5% TFA was added to a final concentration of 10 μM and the suspension incubated for 2 hours 37° C., 5% $CO_2$. Plates were washed twice with PFEA (PBS, 2% FCS, 2 mM EDTA, 0.01% sodium azide) before addition of 50 μl PE labelled anti-human HLA-A2 (Biolegend, Cat. Nr. 343305) Per well diluted 1:250 with PFEA to a final concentration of 0.8 μg/ml. Plates were incubated at 4° C. for 30 minutes before being washed twice with PFEA. Finally, cells were resuspended in fixation solution (PFEA, 1% formaldehyde) and kept at 4° C. before analysis using an iQue Screener (Intellicyt). T2 cells were gated based on the FSC-A/SSC-A signal and doublets removed using an FSC-H/FSC-A doublet exclusion. The PE channel positive gate coordinates were based on an unstained control. Data was plotted using GraphPad Prism v7.

15. Sequence Alignment

Multiple sequence alignments were performed by using Clustal Omega Multiple Sequence Alignment (ebi.ac.uk/

Tools/msa/clustalo/) (Madeira et al. "The EMBL-EBI search and sequence analysis tools APIs in 2019", Nucleic Acids Research, 47:W636-W641, 2019, doi: 10.1093/nar/gkz268).

16. Statistical Analysis

All data were plotted using the GraphPad Prism software version 7. Correlation between x and y datasets were calculated by computing the Pearson correlation coefficient and were reported as $R^2$ using the GraphPad Prism software version 7. $R^2$ and $X^2$ values for curve fittings of biolayer interferometry binding kinetics measurements were calculated using the Octet RED384 system software DataAnalysis HT version 10.0.3.7.

17. Design and Production of Disulfide-Stabilized Empty HLA-A*02:01 Molecules Molecular dynamics simulations of empty and peptide loaded MHC class I molecules have indicated that the former has an increased mobility in the F-pocket that accommodates the C-terminus of the peptide ligand (16). In previous studies with the murine MHC class I molecule H-2K$^b$ introduction of a disulfide bond between opposing residues in the F-pocket by mutating a tyrosine at position 84 and an alanine at position 139 to cysteines was able to stabilize the complex. The mutant could be refolded without full length peptide and was capable of retroactive peptide binding (17, 18).

The inventors hypothesized that the same concept could be applied to the human MHC class I molecule HLA-A*02:01. Modifications resulting in mutations of the tyrosine at position 84 and alanine at position 139 into cysteines were introduced into an HLA-A*02:01 heavy chain expression plasmid. After production as inclusion bodies in *E. coli*, the heavy chain was incubated with similarly produced β$_2$m but without peptide in refolding buffer. After size exclusion chromatography (SEC), no HLA-A*02:01 associated monomer fraction could be observed compared to a wild type control refolded with a 9mer peptide.

In a second approach, the dipeptide GM was added to the refolding: This dipeptide has a very low affinity for the MHC class I complex and assists the refolding (19). During SEC it dissociates quickly from the binding pocket by buffer exchange against the running buffer, yielding purified empty disulfide-stabilized Y84C/A139C HLA-A*02:01. Empty wild type A*02:01 complexes (WT-A*02:01) could not be produced in the same fashion. WT-A*02:01 complexes can be produced with the dipeptide but denature when attempting to remove the dipeptide by buffer exchange.

The inventors also introduced modifications resulting in mutations of phenylalanine at position 22 and serine at position 71 into cysteines into an HLA-A*02:01 heavy chain expression plasmid. After production as inclusion bodies in *E. coli*, the heavy chain was incubated with similarly produced β$_2$m but without peptide in refolding buffer. SEC yielded purified empty disulfide-stabilized F22C/S71C HLA-A*02:01 complexes. The inventors also introduced modifications resulting in mutations of phenylalanine at position 22 and serine at position 71 as well as tryptophan at position 51 and glycine at position 175 into cysteines into an HLA-A*02:01 heavy chain expression plasmid. After production as inclusion bodies in *E. coli*, the heavy chain was incubated with similarly produced β$_2$m but without peptide in refolding buffer. SEC yielded purified empty disulfide-stabilized F22C/S71C W51C/G175C HLA-A*02:01 complexes.

The absence of the dipeptide GM in the purified monomer could be shown by thermal stability analysis through buffer exchange: the empty Y84C/A139C HLA-A*02:01 molecule was less temperature stable (i.e., had a lower melting temperature) than the same molecule still complexed with dipeptide GM (41).

The resulting molecules were either biotinylated at 4° C. overnight and separated from excess biotin by a second SEC run or stored directly at −80° C. prior to use.

18. Peptide Loading and Affinity Measurements Using Soluble TCRs and Wild Type or Disulfide-Modified MHCs Next, the inventors determined whether the disulfide-modified HLA-A*02:01 molecules were capable of peptide-MHC complex formation and TCR ligand binding. Affinity measurements were performed by bio-layer interferometry (BLI) on an OctetRED 384 using the refolded TCR 1G4 as soluble analyte. This TCR recognizes the HLA-A*02:01 specific peptide SLLMWITQC (ESO 9C, SEQ ID NO: 3) derived from the cancer testis antigen NY-ESO-1 or its synthetic variant SLLMWITQV (ESO 9V, SEQ ID NO: 4) (20,21). Biotinylated Y84C/A139C HLA-A*02:01 was either immobilized directly in its empty state or after a short incubation with the peptide ESO 9V on streptavidin-coated biosensors (FIG. 1b). No differences could be detected between peptide incubations of 5 minutes, the minimal time needed to initiate the affinity measurements after assembly, or longer. Further analysis indicated that full exchange was indeed reached within one to two minutes when high peptide concentrations were used. Kinetics were measured across multiple 1G4 concentrations and wild type HLA-A*02:01 directly refolded with ESO 9V served as control.

Figure 2A:
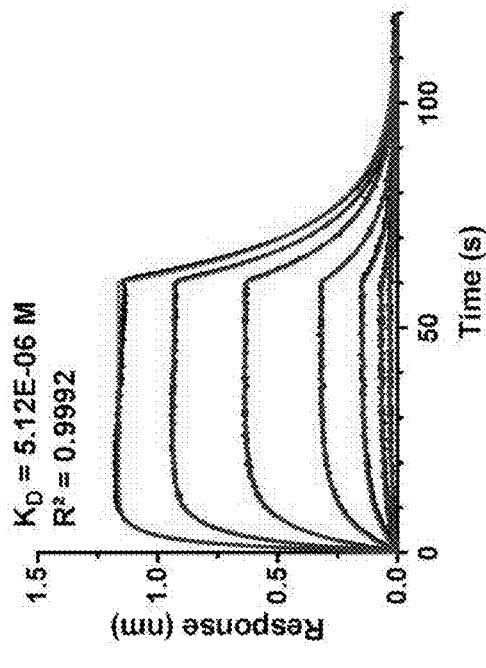
FIGS. 2A-2D show the association and dissociation behavior of 1G4 TCR with different MHC monomers. Raw data is shown in FIGS. 2A and 2B, curve fittings in FIGS. 2C and 2D. All measurements performed as 1:2 analyte dilution series starting at 24 µM.
Figure 2B:
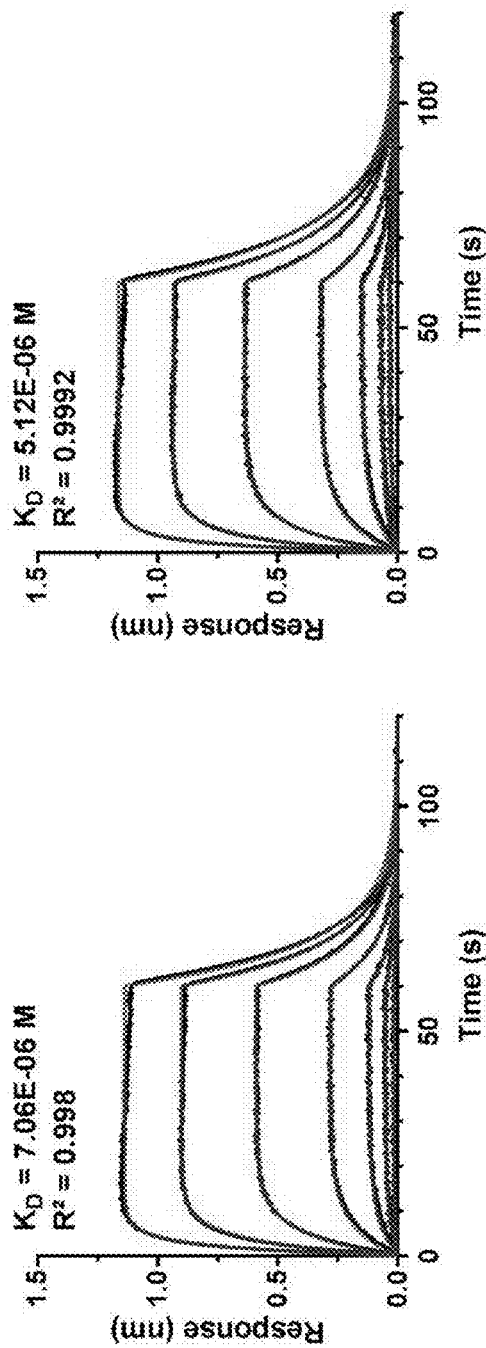
Figure 2C:
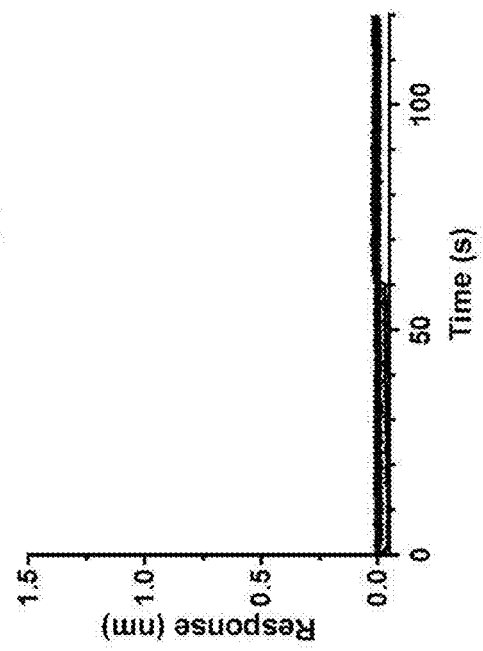
Figure 2D:
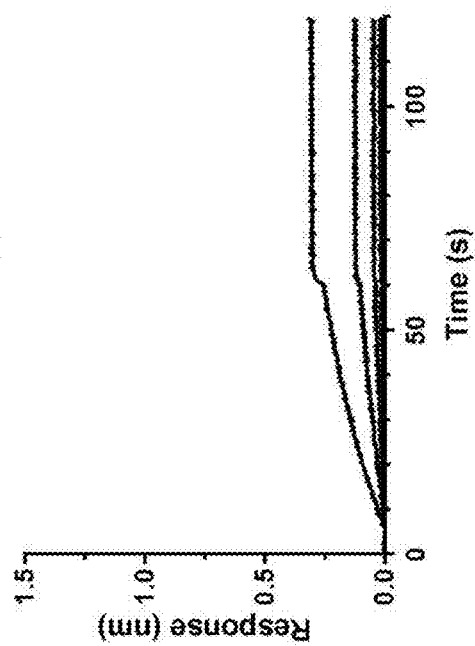
Figure 11A:
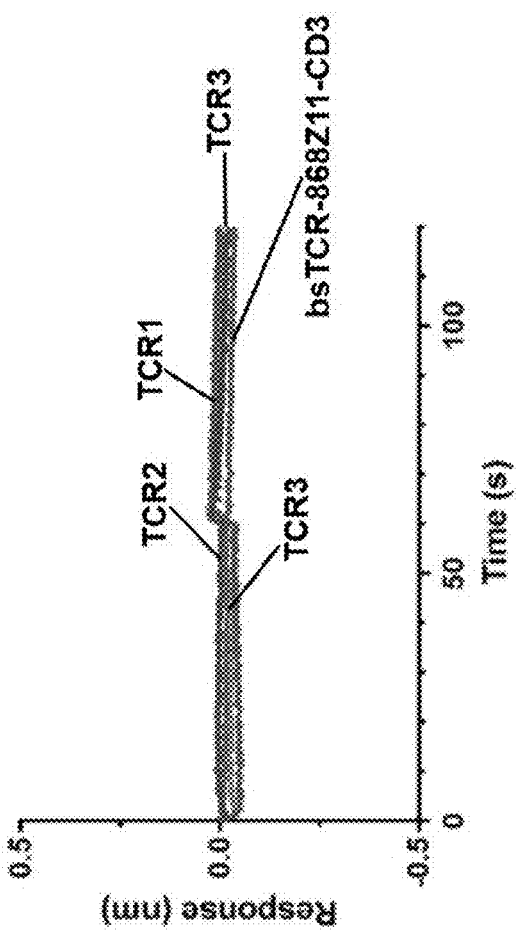
FIG. 11 shows binding of multiple different soluble TCRs and bsTCR bs-868Z11-CD3 to non-loaded Y84C/A139C HLA-A*02:01 or Y84C/A139C HLA-A*02:01 loaded with an irrelevant peptide. (a) Binding of three different HLA-A*02:01 restricted soluble TCRs as well as bs-868Z11-CD3 to functionally-empty Y84C/A139C HLA-A*02:01. Y84C/A139C HLA-A*02:01 was immobilized onto a streptavidin sensor, each TCR supplied at 1 mg/ml (20 µM for soluble TCRs, 13.3 µM for bsTCR). (b) Binding of the same TCRs to Y84C/A139C HLA-A*02:01 loaded with an irrelevant peptide.
Figure 11B:
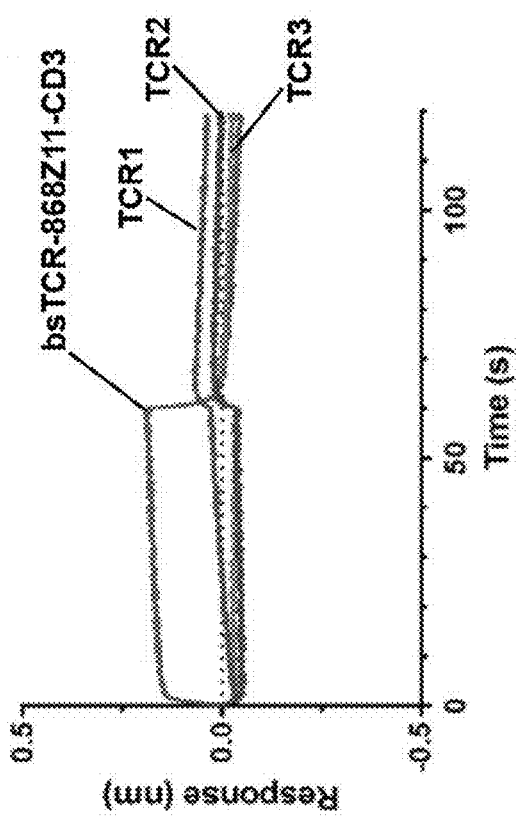

1G4 TCR binding to either Y84C/A139C HLA-A*02:01 9V or WT-A*02:01 ESO 9V was very similar with respect to sensorgrams and $K_d$s resulting from curve fittings (FIGS. 2A and 2B). A weak binding signal (but no dissociation) could be detected for the empty immobilized monomer at high concentrations of 1G4 (FIG. 2C). This binding could be prevented by subsequently adding a peptide that is not recognized by 1G4 like SLYNTVATL (FIG. 2D, SEQ ID NO: 5). The weak signal obtained with empty Y84C/A139C HLA-A*02:01 might be explained by unspecific interactions of the TCR with the empty binding pocket, a state that is typically not encountered by TCRs in vivo. Other A*02:01-restricted soluble TCRs with varying specificities behaved similarly, showing no binding to irrelevantly loaded Y84C/A139C HLA-A*02:01 pMHCs but association to functionally empty molecules, albeit but with a relatively lower response (FIG. 11).

19. Correlation Between Disulfide-Modified HLA-A*02:01 and WT-A*02:01 Affinity Measurements for an Affinity Maturated TCR Having established the usability of the Y84C/A139C HLA-A*02:01 molecule as ligand equivalent to WT-A*02:01 for unmodified TCRs the inventors wanted to expand this analysis towards mutated high affinity TCRs and a larger number of peptide ligands. The inventors employed the maturated single chain TCR (scTv) 868Z11, an affinity maturated variant of a TCR that recognizes the HIV p17 Gag-derived HLA-A*02:01 restricted peptide SLYNTVATL (SL9, SEQ ID NO: 5) (8, 22).

Figure 3A:
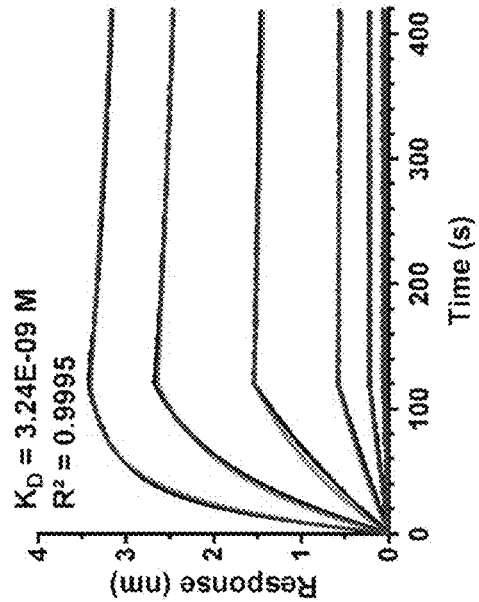
FIGS. 3A-3D show the affinities of the SL9 specific bs-868Z11-CD3 bsTCR with different MHC monomers and peptide ligands.
Figure 3B:
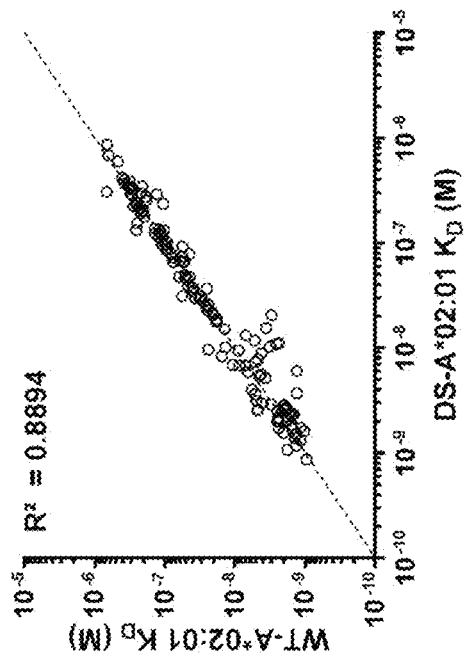
Figure 3C:
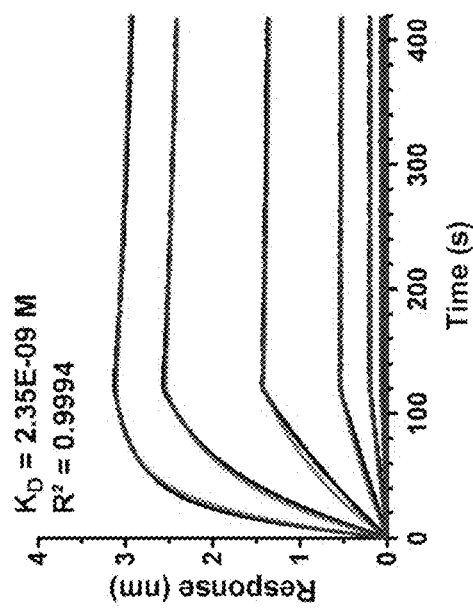
Figure 9:
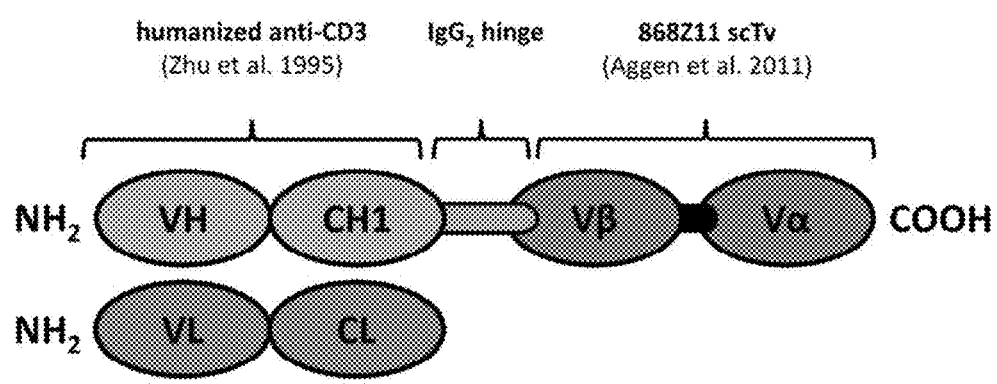
FIG. 9 shows an illustration of bsTCR bs-868Z11-CD3 construct. The 868Z11 domain is based on the SLYNTVATL (SEQ ID NO: 5)-reactive TCR 868 and incorporates affinity enhancing mutations in the CDR2β (YYEEEE (SEQ ID NO: 326) to YVRGEE (SEQ ID NO: 327)) and CDR3α region (CAVRTNSGYALN (SEQ ID NO: 328) to CAVRGAHDYALN (SEQ ID NO: 329)) identified by Varela-Rohena et al. (8). The Vβ and Vα domains of the affinity enhanced TCR were linked through a single chain linker (GSADDAKKDAAKKDGKS (SEQ ID NO: 330)) and further modified with a surface stability conferring mutation in the Vα2 region (F49S) to allow for soluble expression by Aggen et al. (22). To create the bs-868Z11-CD3 molecule, this 868Z11 scTv domain was fused to the F(ab') heavy chain portion of a humanized anti-CD3 antibody through an IgG2 derived CH2 hinge domain (APPVAG (SEQ ID NO: 2)) with two cysteine-knock-outs ($C_{226}S$ and $C_{229}S$), incorporated to prevent the formation of F(ab')$_2$ homodimers on expression.
Figure 14:
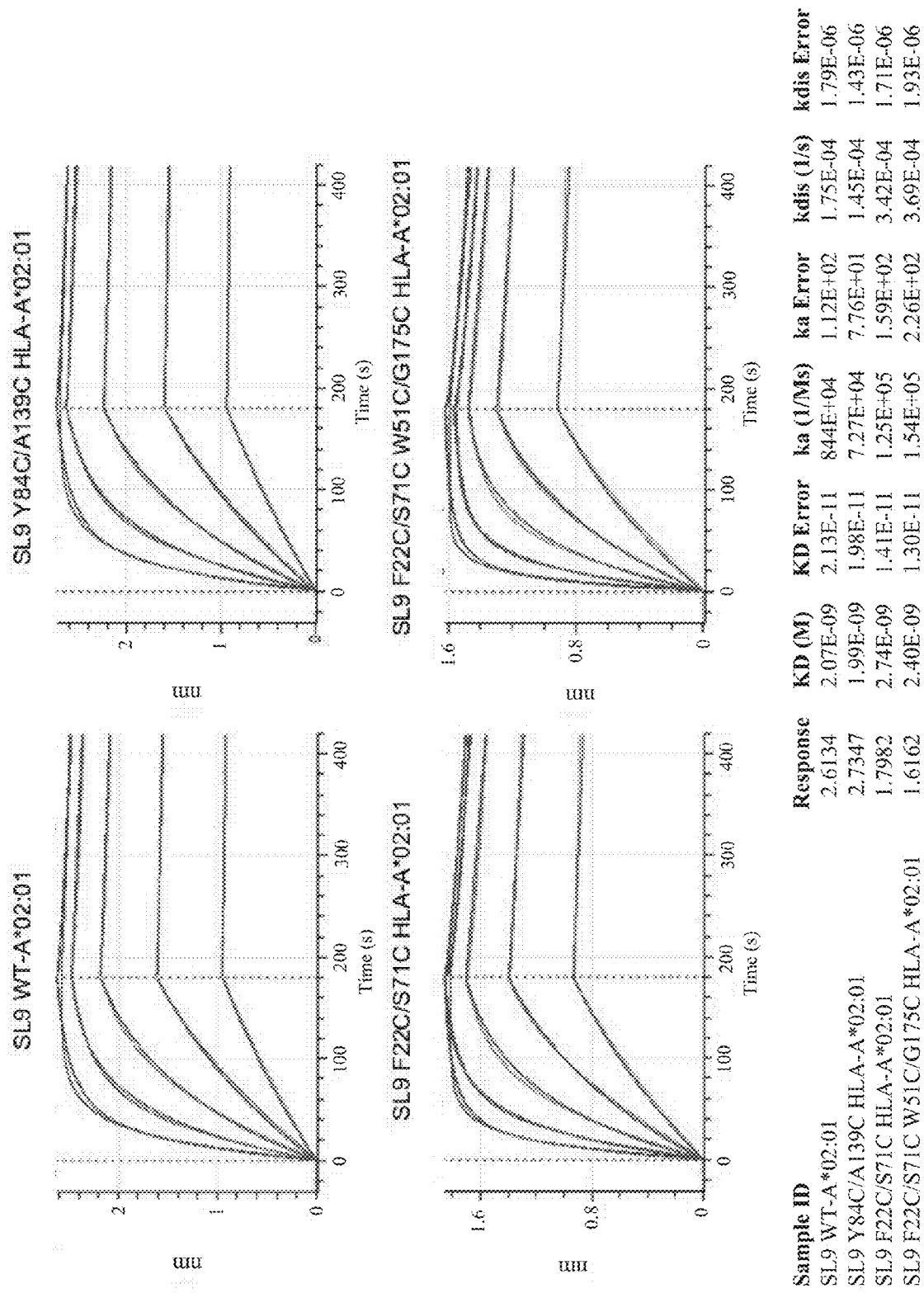
FIG. 14 shows the affinities of the SL9 specific bs-868Z11-CD3 bsTCR towards SL9 pMHC produced with different disulfide-modified HLA-A*02:01 complexes. Binding curves show bs-868Z11-CD3 association and dissociation against immobilized SL9 pMHCs. Measured using 1:2 analyte dilution series starting at 500 nM. Binding curve of the bs-868Z11-CD3 bsTCR against immobilized SL9 WT-HLA*02:01 pMHC (upper left graphic). Binding curve of the bs-868Z11-CD3 bsTCR against immobilized SL9 Y84C/A139C HLA*02:01 pMHC (upper right graphic). Binding curve of the bs-868Z11-CD3 bsTCR against immobilized SL9 F22C/S71C HLA*02:01 (lower left graphic). Binding curve of the bs-868Z11-CD3 bsTCR against immobilized SL9 F22C/S71C W51C/G175C HLA-A*02:01 pMHC (lower right graphic).

The inventors performed affinity measurements by immobilization of empty or SL9 peptide loaded disulfide-modified HLA-A*02:01 molecules on streptavidin biosensor and measurements against soluble bs-868Z11-CD3, a bsTCR variant of the 868Z11 scTv expressed in fusion with a humanised anti-CD3 antibody (FIG. 9)(23). Binding affinity for SL9 disulfide-modified HLA-A*02:01 pMHC complexes using either Y84C/A139C HLA-A*02:01, F22C/S71C HLA-A*02:01 or F22C/S71C W51C/G175C HLA-A*02:01, was similar to the SL9 WT-A*02:01 pMHC produced by performing an UV-light mediated peptide ligand exchange (25) with 2.35 nM and 3.24 nM, respectively (FIG. 3a and, also FIG. 14). No binding was measurable with empty MHC molecules for this bsTCR (FIG. 3c) and with irrelevantly loaded Y84C/A139C HLA-A*02:01 complexes at a high molar concentrations of 13.3 µM.

Next, the inventors analysed bs-868Z11-CD3 binding affinities towards a positional scanning library based on the SL9 peptide sequence. This library was created by exchanging an amino acid at one position of the wild type SL9 peptide against the 18 remaining proteinogenic amino acids while maintaining all other positions, resulting in 162 distinct peptides when performed at all positions of the nonamer (cysteine was excluded because of its propensity to dimerize) (24). pMHC complexes were generated by the inventors either by addition to Y84C/A139C HLA-A*02:01 molecules as before or by performing UV-light mediated peptide ligand exchange, a technology used for pMHC complex generation (25). Respective pMHC complexes were immobilized on streptavidin and kinetics measured at two different bs-868Z11-CD3 concentrations. As expected, using alternated peptide ligands resulted in a wide range of different $K_d$s, ranging from undetectable within the sensitivity limits of the chosen setup to comparable or even stronger than the interaction with the unmodified SL9 peptide.

Figure 3D:
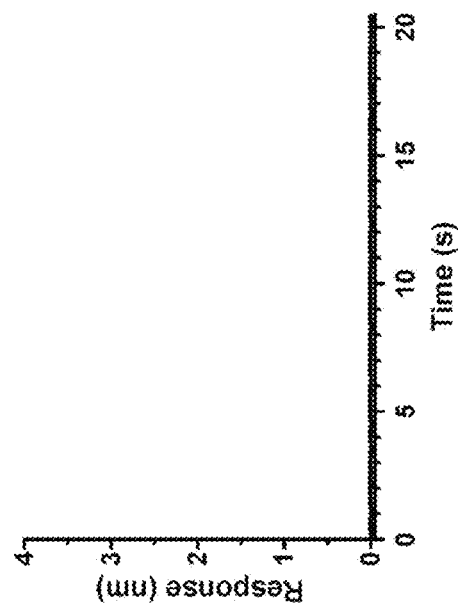

For direct comparison, all measured pMHC complexes were selected that had evaluable signals at both analyte concentrations and curve fittings with $R^2$ values of at least 0.9, representative of signals within the selected $K_d$ sensitivity range. $K_d$ values for the resulting 140 peptide ligands were very similar across the whole affinity range when plotted against each other, a finding supported by the high correlation coefficient value (FIG. 3d). Discrepancies were within 2-fold range for over 90% of the pMHC pairs and 6.82-fold differences at most. Within the group with higher than 2-fold changes a trend towards a larger dissociation constant for measurements with the Y84C/A139C HLA-A*02:01 molecule was observed.

The amount of functional pMHC immobilized on each biosensor expressed by the reported $R_{max}$ value for 140 different peptide ligands from the positional scanning library was comparable for both wild-type and disulfide-stabilized pMHCs (correlation coefficient $R^2$=0.9459).

Figure 15:
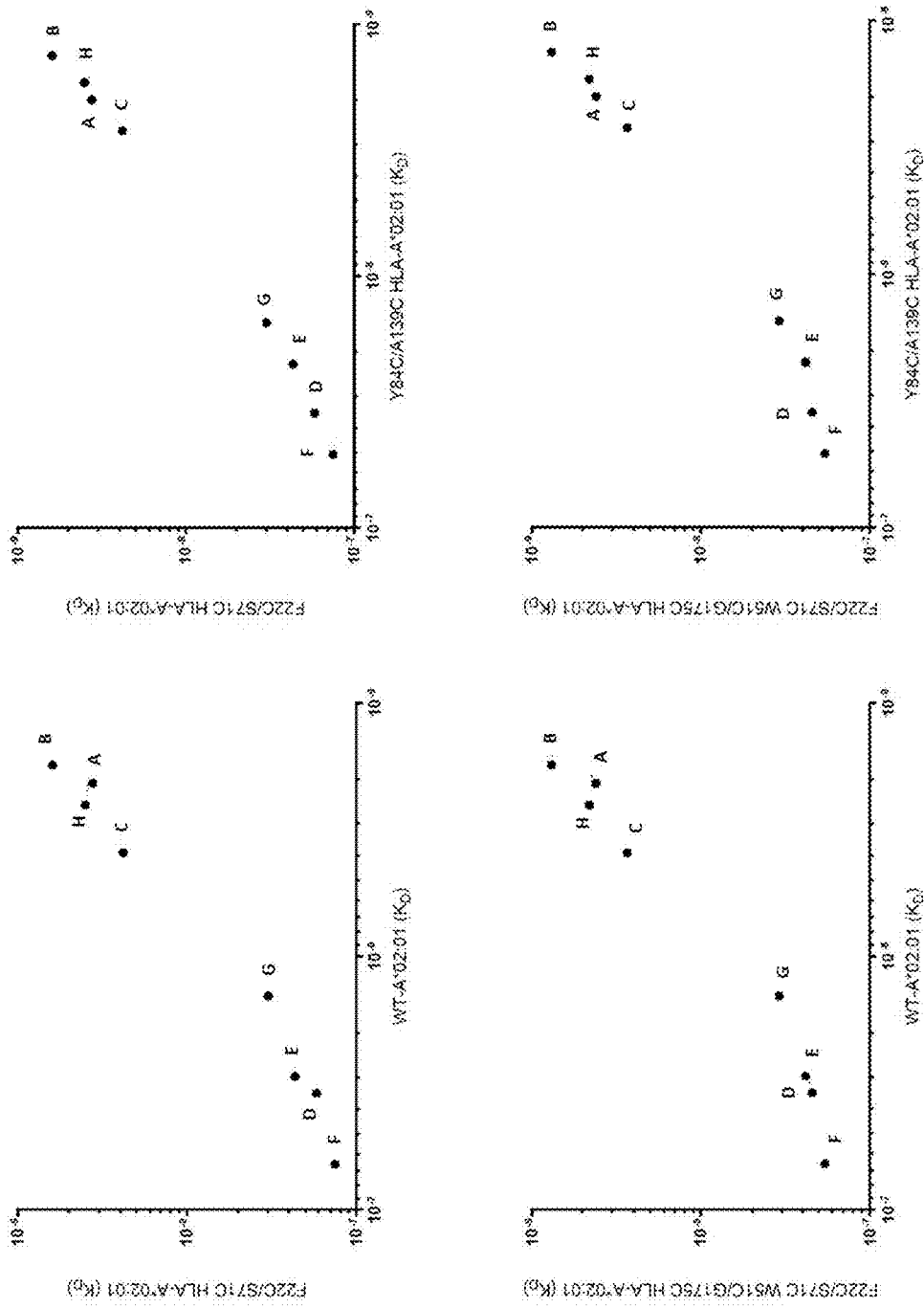
FIG. 15 shows $K_d$ values of a high affinity TCR to different pMHC complexes. In each case the $K_d$ of the WT-A*02:01 molecule is shown on the X-axis and the $K_d$ of the two different disulfide-modified HLA-A*02:01 MHC molecules is shown on the y-axis and each dot represents one of different peptides loaded in the MHC molecule.

FIG. 15 shows $K_d$ values of a high affinity TCR to different pMHC complexes. In each case the $K_d$ of the WT-A*02:01 molecules or the Y84C/A139C HLA-A*02:01 molecule is shown on the X-axis and the $K_d$ of the two different disulfide-modified HLA-A*02:01 MHC molecules is shown on the y-axis and each dot represents one of different peptides loaded in the MHC molecule. In each square in FIG. 15 the following peptides are represented:

A: HIV-005 WT
(SLYNTVATL, SEQ ID NO: 5)

B: HIV-005 6I
(SLYNTIATL, SEQ ID NO: 110)

C: HIV-005 8V
(SLYNTVAVL, SEQ ID NO: 145)

D: HIV-005 3F
(SLFNTVATL, SEQ ID NO: 59)

E: HIV-005 3F6I8V
(SLFNTIAVL), SEQ ID NO: 318)

F: HIV-005 3F8V
(SLFNTVAVL, SEQ ID NO: 319)

G: HIV-005 3F6I
(SLFNTIATL, SEQ ID NO: 320)

H: HIV-005 6I8V
(SLYNTIAVL, SEQ ID NO: 321)

In the upper left panel the $K_d$ for each above-listed peptide for the WT-A*02:01 pMHC complex is plotted against the $K_d$ of the disulfide-modified F22C/S71C HLA-A*02:01 pMHC complex. The disulfide-modified F22C/S71C HLA-A*02:01 pMHC complex shows almost identical $K_D$ values to the WT-A*02:01 pMHC complex for each of the investigated peptides. In the lower left panel the $K_d$ for each above-listed peptide for the WT-A*02:01 pMHC complex is plotted against the $K_D$ of the disulfide-modified F22C/S71C W51C/G175C HLA-A*02:01 pMHC complex and shows also almost identical $K_d$ values to the WT-A*02:01 pMHC complex for each of the investigated peptides.

In the upper right panel the $K_d$ for each above-listed peptide for the Y84C/A139C HLA-A*02:01 pMHC complex is plotted against the $K_d$ of the disulfide-modified F22C/S71C HLA-A*02:01 pMHC complex. In the lower right panel the $K_d$ for each above-listed peptide for the Y84C/A139C HLA-A*02:01 pMHC complex is plotted against the $K_d$ of the disulfide-modified F22C/S71C W51C/G175C HLA-A*02:01 pMHC complex. The disulfide-modified pMHC complexes of the F22C/S71C and the F22C/S71C W51C/G175C mutant have almost identical $K_d$ values compared to the Y84C/A139C HLA-A*02:01 pMHC complex for each of the investigated peptides. It can thus, be concluded that disulfide-modified HLA-A*02:01 molecules loaded with different peptides and forming pMHC complexes are comparably recognized by a respective affinity-maturated TCR to the WT HLA-A*02:01 pMHC complex. Therefore, the function of the disulfide-modified HLA-A*02:01 molecules loaded with peptides (pMHC complexes) is unaffected by the introduction of stabilizing amino acid mutations into the HLA-A*02:01 molecule.

The results shown in FIG. 15 make it credible for the skilled person that the disulfide-modified HLA-A*02:01 molecules according to the present invention loaded with peptide ligands and forming disulfide-modified pMHC complexes elicit a T-cell response upon binding to their respective TCR.

20. High-Throughput Kinetic Screenings for Binding Motif Generation

Quick and flexible generation of pMHCs facilitates the collection of large binding affinity datasets against many different pMHCs. One example of such a dataset is screening of a positional scanning library to generate a pMHC-bsTCR binding motif, which can serve as one component in a bsTCR safety screening approach. To perform such measurements, the pMHC should ideally be used as a soluble analyte because this offers multiple advantages. First, immobilizing the same ligand with known activity repeatedly, for example, a bsTCR, allows better interpretation of the fitting results, especially the reported $R_{max}$ value. Second, using pMHC complexes as soluble analytes instead of immobilizing is preferable for quick and cost effective high throughput screenings, since a broad variety of regeneratable biosensors capable of reversibly immobilizing bispecific TCR constructs exists. These biosensors are typically coated with antibodies and can be used at least 20 times for kinetic measurements without loss of readout quality. Third, immobilizing the bsTCR is the only orientation available for measuring monovalent affinity when a bsTCR or antibody has multiple pMHC binding moieties, because, with immobilized pMHCs, only avidity can be measured.

Figure 10A:
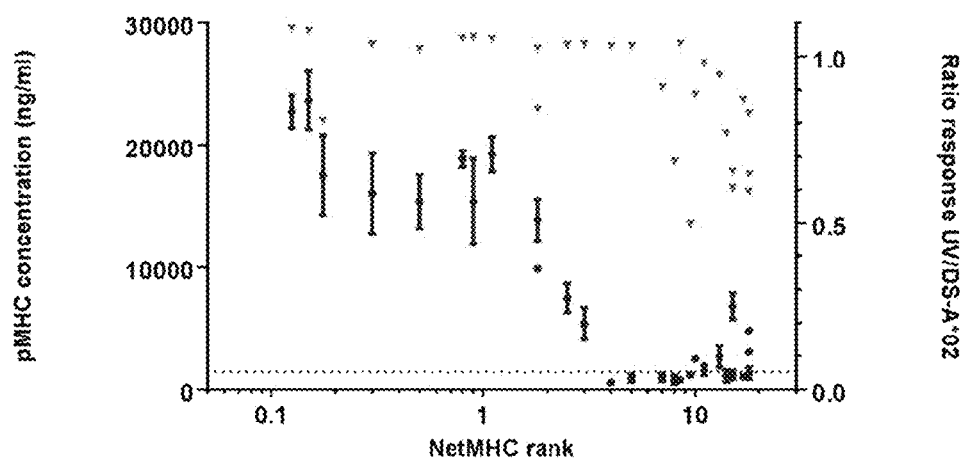
FIGS. 10A and 10B show an analysis of UV exchange efficiency and Octet measurement results for 28 different peptides selected from SLYNTVATL (SEQ ID NO: 5) based positional scanning library.
Figure 10B:
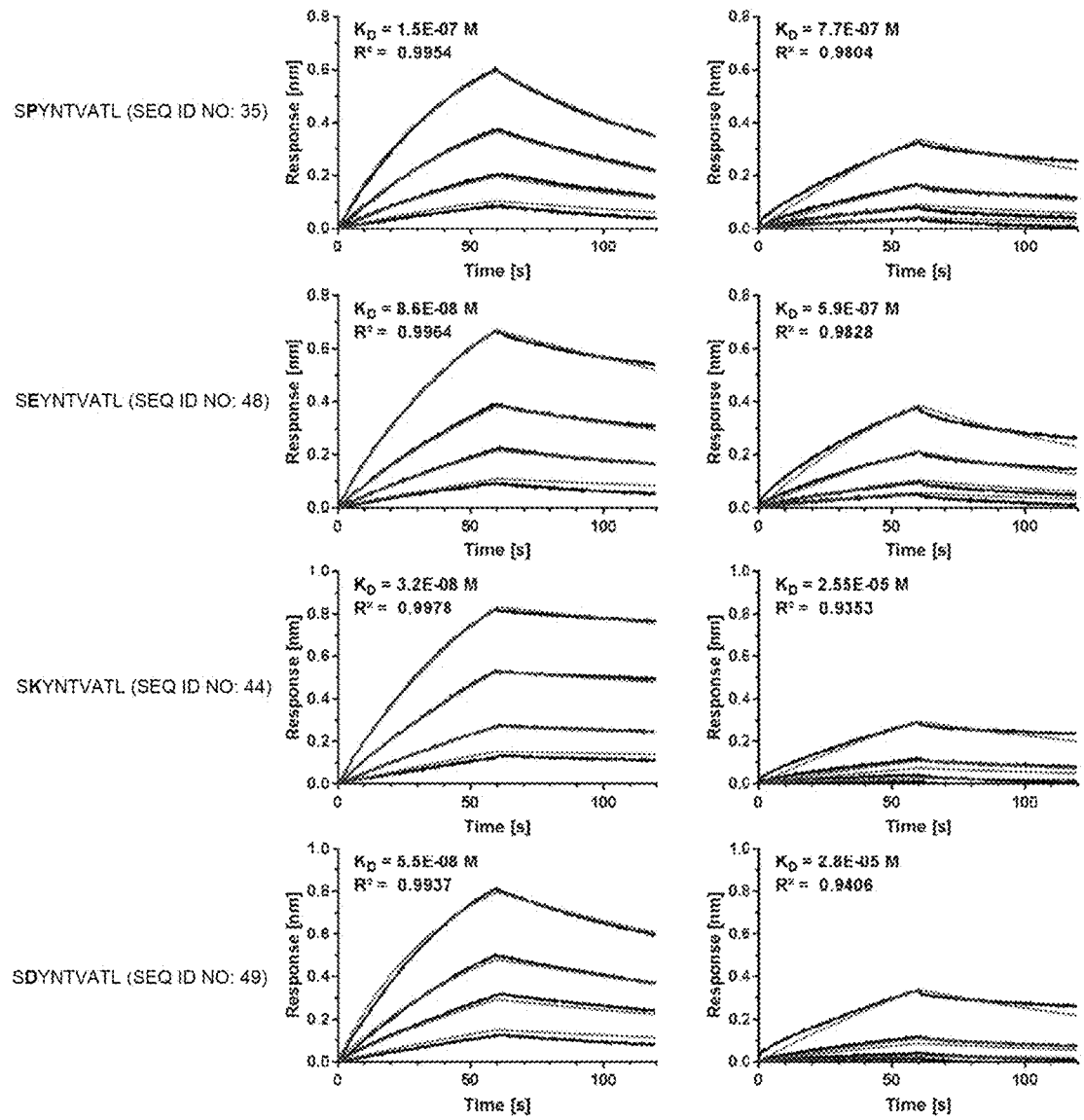

While the UV mediated peptide ligand exchange can generate a high number of different pMHC complexes, the exchange efficiency varies depending on the peptide and its affinity for binding to the respective MHC class I allele, resulting in different pMHC concentrations in the samples (FIG. 10). This uncertainty is a problem for affinity measurements with pMHCs used as soluble analytes, as precise knowledge of the concentration is desired to determine accurate affinities. Since the disulfide-stabilized Y84C/A139C HLA-A*02:01 mutant is stable without any peptide, this restriction does not apply. If the peptides are added at a concentration high enough to saturate the empty MHC complexes, the effective concentration of pMHC is known, significantly increasing the accuracy of the measurements and avoiding false negatives. Examples for this behavior could be detected in the positional scanning library, resulting in bad fitting data and miscalculation of the affinity when UV exchange preparations were used compared to Y84C/A139C HLA-A*02:01 peptide loadings (FIGS. 5, 6, 10) (26). Accurately measuring bsTCR affinities for such peptides can be important in the context of binding motif generations, because these substitutions may result in relevant MHC binders when combined with substitutions at other positions. Tolerance of the amino acids by the bsTCR should thus, be reflected correctly in a comprehensive binding motif.

Figure 4A:
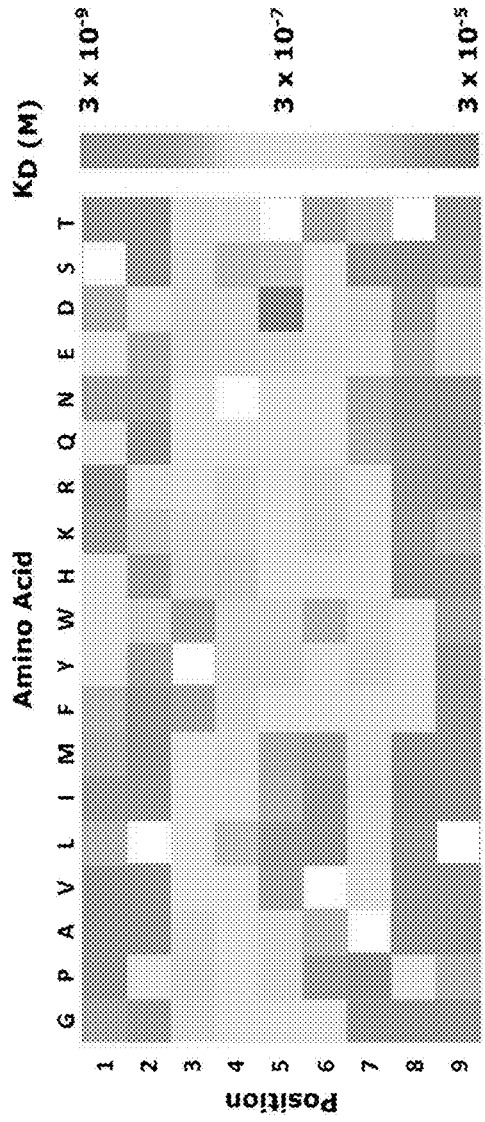
FIGS. 4A-4C show the binding motif of bs-868Z11-CD3 generated using Y84C/A139C HLA-A*02:01 generated mutated amino acid sequence library as soluble analyte and immobilized bsTCR. $K_d$s were fitted using curves from at least one and up of the inventors' analyte concentrations with at least a peak signal of 0.05 nm for curves to be included. Positions with no fittable curves were assigned a $K_d$ of $5\times10^{-6}$ M. Measured using $1/\sqrt{10}$ analyte dilution series starting at 500 nM.
Figure 8:
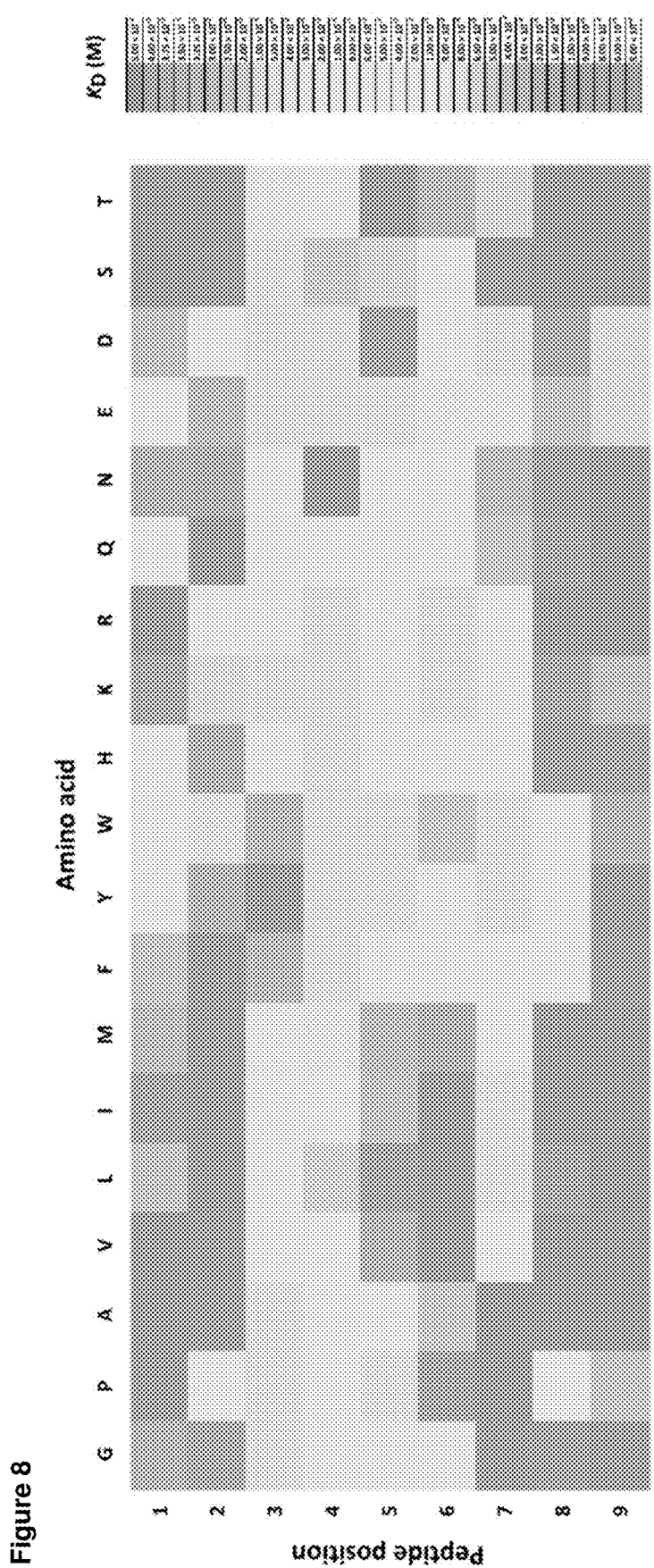
FIG. 8 shows the binding motif of bs-868Z11-CD3 generated using Y84C/A139C HLA-A*02:01 generated positional scanning library as soluble analyte and immobilized bsTCR. Measurements were performed using four soluble analyte concentrations. Positions with no fittable curves were assigned a $K_d$ of $5\times10^{-6}$ M. Soluble analyte concentration range produced by 1/analyte dilution series starting at 500 nM. Heat map of affinities depending on the amino acid introduced and the exchanged position in the peptide sequence.

By immobilizing the bs-868Z11-CD3 bsTCR the inventors were able to analyze the positional scanning library at four different soluble pMHC concentrations for each peptide ligand, ranging from 500 to 15.8 nM, within 4 hours of unattended measurement time at a 20-fold reduced price tag. All curves reaching at least a signal level of 0.05 nm were included in the fittings, resulting in a comprehensive TCR binding motif (FIGS. 4a, 8, Table 3).

Table 3: bs-868Z11-CD3 binding affinity for SV9 peptide SLYNTVATL (SEQ ID NO: 5) and peptides from positional scanning library (SEQ ID NOS: 16-177). Table includes $K_D$, $k_{on}$ and $k_{off}$ values determined by curve fittings following a 1:1 Langmuir binding model using the Fortebio Data Analysis HT 10.0.3.7 software. Respective errors are reported as well as accuracy of the fit according to the model. Peptides reported as "No fit" had no evaluable curves reaching at least a peak signal of 0.05 nm at any concentration.

TABLE 3 bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ ($M^{-1}s^{-1}$) | $k_{on}$ Error | $k_{off}$ ($s^{-1}$) | $k_{off}$ Error | Full $X^2$ | Full $R^2$ |
|---|---|---|---|---|---|---|---|---|
| SLYNTVATL (5) | 3.81E-09 | 1.49E-10 | 1.03E+05 | 1.45E+02 | 3.91E-04 | 1.53E-05 | 0.262 | 0.9993 |
| GLYNTVATL (16) | 3.05E-08 | 3.55E-10 | 1.04E+05 | 3.42E+02 | 3.19E-03 | 3.56E-05 | 1.0915 | 0.9966 |
| PLYNTVATL (17) | 8.54E-09 | 3.46E-10 | 9.65E+04 | 3.03E+02 | 8.24E-04 | 3.33E-05 | 1.2363 | 0.9969 |
| ALYNTVATL (18) | 5.82E-09 | 3.18E-10 | 1.04E+05 | 3.14E+02 | 6.04E-04 | 3.29E-05 | 1.2791 | 0.9969 |
| VLYNTVATL (19) | 5.74E-09 | 2.24E-10 | 1.05E+05 | 2.27E+02 | 6.04E-04 | 2.35E-05 | 0.6719 | 0.9984 |
| LLYNTVATL (20) | 4.99E-08 | 2.99E-10 | 1.04E+05 | 2.67E+02 | 5.17E-03 | 2.80E-05 | 0.5623 | 0.9981 |
| ILYNTVATL (21) | 1.35E-08 | 2.35E-10 | 1.06E+05 | 2.40E+02 | 1.43E-03 | 2.47E-05 | 0.6748 | 0.9982 |
| MLYNTVATL (22) | 4.19E-08 | 2.95E-10 | 1.09E+05 | 2.93E+02 | 4.56E-03 | 2.96E-05 | 0.6922 | 0.9978 |
| FLYNTVATL (23) | 5.22E-08 | 3.07E-10 | 1.15E+05 | 3.20E+02 | 6.02E-03 | 3.13E-05 | 0.6452 | 0.9976 |
| YLYNTVATL (24) | 1.24E-07 | 5.65E-10 | 1.15E+05 | 4.01E+02 | 1.43E-02 | 4.21E-05 | 0.4931 | 0.9972 |
| WLYNTVATL (25) | 4.62E-07 | 4.57E-09 | 1.66E+05 | 1.48E+03 | 7.66E-02 | 3.27E-04 | 0.1216 | 0.9955 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ ($M^{-1}s^{-1}$) | $k_{on}$ Error | $k_{off}$ ($s^{-1}$) | $k_{off}$ Error | Full $X^2$ | Full $R^2$ |
|---|---|---|---|---|---|---|---|---|
| HLYNTVATL (26) | 3.43E-07 | 2.50E-09 | 1.34E+05 | 8.87E+02 | 4.60E-02 | 1.43E-04 | 0.1908 | 0.9961 |
| KLYNTVATL (27) | 1.91E-08 | 2.14E-10 | 9.03E+04 | 1.67E+02 | 1.73E-03 | 1.91E-05 | 0.3239 | 0.999 |
| RLYNTVATL (28) | 4.42E-09 | 5.15E-10 | 8.86E+04 | 3.93E+02 | 3.92E-04 | 4.56E-05 | 2.0699 | 0.9944 |
| QLYNTVATL (29) | 1.38E-07 | 5.55E-10 | 9.85E+04 | 3.05E+02 | 1.36E-02 | 3.50E-05 | 0.3534 | 0.9981 |
| NLYNTVATL (30) | 3.13E-08 | 3.42E-10 | 9.84E+04 | 2.98E+02 | 3.08E-03 | 3.23E-05 | 0.9466 | 0.9973 |
| ELYNTVATL (31) | 4.85E-07 | 4.84E-09 | 9.29E+04 | 8.66E+02 | 4.50E-02 | 1.63E-04 | 0.4525 | 0.9948 |
| DLYNTVATL (32) | 4.49E-08 | 3.46E-10 | 9.55E+04 | 2.77E+02 | 4.28E-03 | 3.06E-05 | 0.7816 | 0.9977 |
| TLYNTVATL (33) | 6.94E-09 | 2.07E-10 | 1.02E+05 | 1.98E+02 | 7.07E-04 | 2.10E-05 | 0.544 | 0.9988 |
| SGYNTVATL (34) | 1.86E-08 | 4.56E-10 | 8.40E+04 | 3.18E+02 | 1.56E-03 | 3.79E-05 | 1.3876 | 0.9964 |
| SPYNTVATL (35) | 1.65E-07 | 2.27E-09 | 6.80E+04 | 7.29E+02 | 1.12E-02 | 9.66E-05 | 2.2025 | 0.9852 |
| SAYNTVATL (36) | 1.00E-08 | 1.28E-10 | 1.02E+05 | 1.23E+02 | 1.02E-03 | 1.30E-05 | 0.2052 | 0.9995 |
| SVYNTVATL (37) | 8.47E-09 | 1.64E-10 | 1.01E+05 | 1.55E+02 | 8.57E-04 | 1.65E-05 | 0.3327 | 0.9992 |
| SIYNTVATL (38) | 8.68E-09 | 9.77E-11 | 1.02E+05 | 9.42E+01 | 8.89E-04 | 9.97E-06 | 0.1192 | 0.9997 |
| SMYNTVATL (39) | 6.55E-09 | 2.07E-10 | 1.01E+05 | 1.95E+02 | 6.61E-04 | 2.08E-05 | 0.4808 | 0.9987 |
| SFYNTVATL (40) | 8.52E-09 | 3.97E-10 | 9.54E+04 | 3.41E+02 | 8.13E-04 | 3.77E-05 | 1.5251 | 0.996 |
| SYYNTVATL (41) | 3.26E-08 | 3.90E-10 | 5.83E+04 | 1.62E+02 | 1.90E-03 | 2.21E-05 | 0.23 | 0.9989 |
| SWYNTVATL (42) | 8.16E-08 | 1.74E-09 | 4.46E+04 | 4.66E+02 | 3.64E-03 | 6.77E-05 | 0.9827 | 0.991 |
| SHYNTVATL (43) | 2.73E-08 | 8.86E-10 | 6.92E+04 | 4.66E+02 | 1.89E-03 | 5.99E-05 | 2.1947 | 0.9915 |
| SKYNTVATL (44) | 7.43E-08 | 1.57E-09 | 5.08E+04 | 5.00E+02 | 3.77E-03 | 7.06E-05 | 2.0162 | 0.9899 |
| SRYNTVATL (45) | 1.02E-07 | 2.33E-09 | 4.84E+04 | 6.42E+02 | 4.95E-03 | 9.17E-05 | 0.6946 | 0.9837 |
| SQYNTVATL (46) | 9.41E-09 | 2.19E-10 | 1.09E+05 | 2.35E+02 | 1.03E-03 | 2.37E-05 | 0.6976 | 0.9984 |
| SNYNTVATL (47) | 2.45E-08 | 6.68E-10 | 6.85E+04 | 3.45E+02 | 1.68E-03 | 4.50E-05 | 1.7367 | 0.9953 |
| SEYNTVATL (48) | 4.09E-08 | 1.77E-09 | 5.16E+04 | 6.23E+02 | 2.11E-03 | 8.78E-05 | 4.5691 | 0.9843 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ ($M^{-1}s^{-1}$) | $k_{on}$ Error | $k_{off}$ ($s^{-1}$) | $k_{off}$ Error | Full $X^2$ | Full $R^2$ |
|---|---|---|---|---|---|---|---|---|
| SDYNTVATL (49) | 1.01E-07 | 1.68E-09 | 6.51E+04 | 6.61E+02 | 6.56E-03 | 8.69E-05 | 3.2507 | 0.9854 |
| SSYNTVATL (50) | 8.17E-09 | 1.97E-10 | 9.64E+04 | 1.72E+02 | 7.88E-04 | 1.89E-05 | 0.4063 | 0.999 |
| STYNTVATL (51) | 5.41E-09 | 1.49E-10 | 9.87E+04 | 1.35E+02 | 5.34E-04 | 1.47E-05 | 0.2427 | 0.9994 |
| SLGNTVATL (52) | No fit | | | | | | | |
| SLPNTVATL (53) | No fit | | | | | | | |
| SLANTVATL (54) | No fit | | | | | | | |
| SLVNTVATL (55) | 5.11E-07 | 5.80E-09 | 1.95E+05 | 2.01E+03 | 9.96E-02 | 4.80E-04 | 0.0769 | 0.9966 |
| SLLNTVATL (56) | 1.32E-07 | 8.45E-10 | 1.21E+05 | 6.09E+02 | 1.60E-02 | 6.33E-05 | 1.038 | 0.9944 |
| SLINTVATL (57) | 4.77E-07 | 5.50E-09 | 1.40E+05 | 1.48E+03 | 6.69E-02 | 3.15E-04 | 0.325 | 0.9939 |
| SLMNTVATL (58) | 1.07E-06 | 5.52E-08 | 2.35E+05 | 1.12E+04 | 2.50E-01 | 5.13E-03 | 0.1244 | 0.979 |
| SLFNTVATL (59) | 3.47E-08 | 1.92E-10 | 9.54E+04 | 1.59E+02 | 3.31E-03 | 1.75E-05 | 0.2445 | 0.9992 |
| SLWNTVATL (60) | 3.36E-08 | 1.91E-10 | 9.34E+04 | 1.53E+02 | 3.14E-03 | 1.71E-05 | 0.2479 | 0.9992 |
| SLHNTVATL (61) | 9.09E-08 | 3.31E-10 | 1.16E+05 | 2.84E+02 | 1.06E-02 | 2.85E-05 | 0.3676 | 0.9984 |
| SLKNTVATL (62) | No fit | | | | | | | |
| SLRNTVATL (63) | 5.55E-07 | 5.54E-09 | 9.64E+04 | 9.00E+02 | 5.35E-02 | 1.88E-04 | 0.1675 | 0.9957 |
| SLQNTVATL (64) | 6.29E-07 | 9.45E-09 | 2.62E+05 | 3.51E+03 | 1.65E-01 | 1.11E-03 | 0.0384 | 0.9961 |
| SLNNTVATL (65) | 4.74E-07 | 5.90E-09 | 1.81E+05 | 2.05E+03 | 8.59E-02 | 4.48E-04 | 0.1049 | 0.9953 |
| SLENTVATL (66) | No fit | | | | | | | |
| SLDNTVATL (67) | No fit | | | | | | | |
| SLSNTVATL (68) | No fit | | | | | | | |
| SLTNTVATL (69) | 3.01E-06 | 3.45E-06 | 1.88E+05 | 2.15E+05 | 5.66E-01 | 6.50E-02 | 0.1123 | 0.9199 |
| SLYGTVATL (70) | 5.33E-07 | 1.20E-08 | 2.07E+05 | 4.15E+03 | 1.11E-01 | 1.12E-03 | 0.5678 | 0.9842 |
| SLYPTVATL (71) | 5.54E-07 | 1.44E-08 | 3.62E+05 | 8.18E+03 | 2.00E-01 | 2.58E-03 | 0.0884 | 0.9892 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ ($M^{-1}s^{-1}$) | $k_{on}$ Error | $k_{off}$ ($s^{-1}$) | $k_{off}$ Error | Full $X^2$ | Full $R^2$ |
|---|---|---|---|---|---|---|---|---|
| SLYATVATL (72) | 1.15E-07 | 6.46E-10 | 1.40E+05 | 6.09E+02 | 1.60E-02 | 5.72E-05 | 0.9354 | 0.9952 |
| SLYVTVATL (73) | 1.80E-07 | 9.65E-10 | 1.31E+05 | 5.98E+02 | 2.35E-02 | 6.64E-05 | 0.4669 | 0.9962 |
| SLYLTVATL (74) | 6.70E-08 | 3.12E-10 | 1.11E+05 | 2.85E+02 | 7.44E-03 | 2.89E-05 | 0.5152 | 0.9981 |
| SLYITVATL (75) | 5.25E-07 | 5.68E-09 | 1.18E+05 | 1.18E+03 | 6.19E-02 | 2.55E-04 | 0.2208 | 0.9949 |
| SLYMTVATL (76) | 1.88E-06 | 2.10E-06 | 3.58E+05 | 3.96E+05 | 6.72E-01 | 1.11E-01 | 0.09 | 0.876 |
| SLYFTVATL (77) | No fit | | | | | | | |
| SLYYTVATL (78) | No fit | | | | | | | |
| SLYWTVATL (79) | No fit | | | | | | | |
| SLYHTVATL (80) | 8.11E-08 | 6.16E-10 | 1.38E+05 | 7.03E+02 | 1.12E-02 | 6.26E-05 | 1.8422 | 0.9923 |
| SLYKTVATL (81) | No fit | | | | | | | |
| SLYRTVATL (82) | No fit | | | | | | | |
| SLYQTVATL (83) | 2.84E-07 | 3.23E-09 | 1.71E+05 | 1.73E+03 | 4.86E-02 | 2.53E-04 | 0.6721 | 0.9898 |
| SLYETVATL (84) | No fit | | | | | | | |
| SLYDTVATL (85) | No fit | | | | | | | |
| SLYSTVATL (86) | 5.95E-08 | 2.69E-10 | 1.27E+05 | 3.13E+02 | 7.57E-03 | 2.87E-05 | 0.5404 | 0.9981 |
| SLYTTVATL (87) | 1.61E-07 | 7.59E-10 | 1.35E+05 | 5.34E+02 | 2.18E-02 | 5.63E-05 | 0.3965 | 0.9968 |
| SLYNGVATL (88) | 6.03E-07 | 1.50E-07 | 5.42E+05 | 1.29E+05 | 3.27E-01 | 2.34E-02 | 0.0452 | 0.9399 |
| SLYNPVATL (89) | No fit | | | | | | | |
| SLYNAVATL (90) | 9.66E-08 | 5.82E-10 | 1.27E+05 | 5.41E+02 | 1.22E-02 | 5.20E-05 | 0.9944 | 0.995 |
| SLYNVVATL (91) | 3.07E-08 | 4.63E-10 | 9.09E+04 | 3.58E+02 | 2.79E-03 | 4.06E-05 | 1.3333 | 0.9958 |
| SLYNLVATL (92) | 1.46E-08 | 3.05E-10 | 9.80E+04 | 2.73E+02 | 1.43E-03 | 2.97E-05 | 0.917 | 0.9976 |
| SLYNIVATL (93) | 4.85E-08 | 3.37E-10 | 8.41E+04 | 2.21E+02 | 4.08E-03 | 2.62E-05 | 0.4314 | 0.9984 |
| SLYNMVATL (94) | 4.26E-08 | 3.52E-10 | 1.20E+05 | 4.09E+02 | 5.12E-03 | 3.86E-05 | 1.2415 | 0.9962 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | $K_D$ (M) | KD Error | $k_{on}$ ($M^{-1}s^{-1}$) | $k_{on}$ Error | $k_{off}$ ($s^{-1}$) | $k_{off}$ Error | Full $X^2$ | Full $R^2$ |
|---|---|---|---|---|---|---|---|---|
| SLYNFVATL (95) | 7.26E-07 | 3.75E-08 | 2.97E+05 | 1.36E+04 | 2.16E-01 | 5.09E-03 | 0.3346 | 0.9697 |
| SLYNYVATL (96) | 4.60E-06 | 9.88E-06 | 1.37E+05 | 2.94E+05 | 6.31E-01 | 9.34E-02 | 0.1113 | 0.8904 |
| SLYNWVATL (97) | No fit | | | | | | | |
| SLYNHVATL (98) | 6.23E-07 | 4.07E-08 | 4.00E+05 | 2.26E+04 | 2.49E-01 | 8.17E-03 | 0.2106 | 0.9526 |
| SLYNKVATL (99) | 2.24E-07 | 1.05E-09 | 1.35E+05 | 5.55E+02 | 3.02E-02 | 6.82E-05 | 0.2572 | 0.9973 |
| SLYNRVATL (100) | 7.78E-07 | 7.24E-08 | 3.54E+05 | 3.19E+04 | 2.76E-01 | 6.54E-03 | 0.02 | 0.9899 |
| SLYNQVATL (101) | 4.72E-07 | 7.25E-09 | 2.10E+05 | 2.90E+03 | 9.91E-02 | 6.64E-04 | 0.131 | 0.9936 |
| SLYNNVATL (102) | 1.19E-07 | 5.68E-10 | 1.32E+05 | 4.88E+02 | 1.58E-02 | 4.76E-05 | 0.5956 | 0.9966 |
| SLYNEVATL (103) | No fit | | | | | | | |
| SLYNDVATL (104) | 3.91E-05 | 5.33E-04 | 1.23E+04 | 1.67E+05 | 4.79E-01 | 5.67E-02 | 0.1685 | 0.904 |
| SLYNSVATL (105) | 6.91E-08 | 3.75E-10 | 1.21E+05 | 3.86E+02 | 8.39E-03 | 3.68E-05 | 0.7181 | 0.997 |
| SLYNTGATL (106) | 1.34E-07 | 6.48E-10 | 1.37E+05 | 5.33E+02 | 1.84E-02 | 5.26E-05 | 0.5267 | 0.9965 |
| SLYNTPATL (107) | 1.54E-08 | 1.56E-10 | 1.19E+05 | 1.93E+02 | 1.83E-03 | 1.82E-05 | 0.3561 | 0.999 |
| SLYNTAATL (108) | 5.48E-08 | 3.74E-10 | 1.10E+05 | 3.59E+02 | 6.05E-03 | 3.62E-05 | 0.8843 | 0.9967 |
| SLYNTLATL (109) | 9.08E-09 | 1.01E-10 | 1.12E+05 | 1.15E+02 | 1.02E-03 | 1.13E-05 | 0.15 | 0.9996 |
| SLYNTIATL (110) | 8.74E-09 | 1.86E-10 | 9.97E+04 | 1.72E+02 | 8.71E-04 | 1.85E-05 | 0.3788 | 0.999 |
| SLYNTMATL (111) | 2.72E-08 | 3.66E-10 | 9.75E+04 | 3.17E+02 | 2.65E-03 | 3.46E-05 | 0.9551 | 0.9966 |
| SLYNTFATL (112) | 5.79E-07 | 6.47E-09 | 7.96E+04 | 8.39E+02 | 4.61E-02 | 1.69E-04 | 0.1416 | 0.9946 |
| SLYNTYATL (113) | 4.43E-07 | 8.76E-09 | 4.61E+04 | 8.61E+02 | 2.04E-02 | 1.33E-04 | 0.1286 | 0.9831 |
| SLYNTWATL (114) | 1.74E-05 | 1.28E-05 | 1.91E+03 | 1.41E+03 | 3.33E-02 | 2.40E-04 | 0.0063 | 0.9878 |
| SLYNTHATL (115) | 1.75E-07 | 1.46E-09 | 7.39E+04 | 4.94E+02 | 1.30E-02 | 6.42E-05 | 0.3653 | 0.9929 |
| SLYNTKATL (116) | No fit | | | | | | | |
| SLYNTRATL (117) | No fit | | | | | | | |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|
| SLYNTQATL (118) | 2.71E-07 | 1.50E-09 | 1.19E+05 | 5.86E+02 | 3.22E-02 | 7.94E-05 | 0.1392 | 0.9969 |
| SLYNTNATL (119) | 1.79E-07 | 7.80E-10 | 1.20E+05 | 4.42E+02 | 2.15E-02 | 5.03E-05 | 0.2983 | 0.9974 |
| SLYNTEATL (120) | 1.43E-06 | 5.11E-08 | 5.54E+04 | 1.93E+03 | 7.94E-02 | 5.83E-04 | 0.0772 | 0.99 |
| SLYNTDATL (121) | 6.04E-07 | 7.08E-09 | 1.12E+05 | 1.22E+03 | 6.77E-02 | 2.89E-04 | 0.1139 | 0.995 |
| SLYNTSATL (122) | 1.66E-07 | 6.43E-10 | 1.43E+05 | 4.69E+02 | 2.38E-02 | 4.93E-05 | 0.2673 | 0.9979 |
| SLYNTTATL (123) | 3.37E-08 | 4.58E-10 | 1.07E+05 | 4.51E+02 | 3.59E-03 | 4.64E-05 | 1.7673 | 0.9938 |
| SLYNTVGTL (124) | 8.29E-09 | 4.59E-10 | 8.24E+04 | 3.12E+02 | 6.83E-04 | 3.77E-05 | 1.2283 | 0.996 |
| SLYNTVPTL (125) | 3.71E-09 | 4.42E-10 | 1.22E+05 | 5.76E+02 | 4.51E-04 | 5.36E-05 | 4.052 | 0.9904 |
| SLYNTVVTL (126) | 5.99E-07 | 1.07E-08 | 1.44E+05 | 2.37E+03 | 8.64E-02 | 6.15E-04 | 0.1883 | 0.9892 |
| SLYNTVLTL (127) | No fit | | | | | | | |
| SLYNTVITL (128) | No fit | | | | | | | |
| SLYNTVMTL (129) | 1.02E-07 | 4.28E-10 | 6.90E+04 | 1.80E+02 | 7.04E-03 | 2.31E-05 | 0.1333 | 0.9988 |
| SLYNTVFTL (130) | 5.14E-07 | 1.01E-08 | 1.72E+05 | 3.07E+03 | 8.85E-02 | 7.06E-04 | 0.1274 | 0.9897 |
| SLYNTVYTL (131) | No fit | | | | | | | |
| SLYNTVWTL (132) | No fit | | | | | | | |
| SLYNTVHTL (133) | 1.14E-07 | 2.51E-10 | 8.42E+04 | 1.27E+02 | 9.63E-03 | 1.53E-05 | 0.0763 | 0.9995 |
| SLYNTVKTL (134) | 1.20E-06 | 5.58E-08 | 5.35E+04 | 2.43E+03 | 6.42E-02 | 6.41E-04 | 0.0792 | 0.9775 |
| SLYNTVRTL (135) | 1.28E-06 | 2.41E-08 | 2.49E+04 | 4.61E+02 | 3.20E-02 | 9.10E-05 | 0.0547 | 0.9967 |
| SLYNTVQTL (136) | 5.38E-08 | 7.00E-10 | 6.84E+04 | 3.40E+02 | 3.68E-03 | 4.43E-05 | 0.9296 | 0.9952 |
| SLYNTVNTL (137) | 4.11E-08 | 8.02E-10 | 7.22E+04 | 4.32E+02 | 2.97E-03 | 5.51E-05 | 1.5878 | 0.9921 |
| SLYNTVETL (138) | 1.61E-06 | 2.46E-07 | 5.74E+03 | 8.80E+02 | 9.22E-03 | 1.00E-04 | 0.007 | 0.989 |
| SLYNTVDTL (139) | No fit | | | | | | | |
| SLYNTVSTL (140) | 1.04E-08 | 4.47E-10 | 9.80E+04 | 4.00E+02 | 1.02E-03 | 4.36E-05 | 1.9634 | 0.9944 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | $K_D$ (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|
| SLYNTVTTL (141) | 6.90E-08 | 2.99E-10 | 9.23E+04 | 2.09E+02 | 6.37E-03 | 2.36E-05 | 0.2893 | 0.9987 |
| SLYNTVAGL (142) | 1.14E-08 | 1.42E-10 | 1.14E+05 | 1.65E+02 | 1.30E-03 | 1.61E-05 | 0.302 | 0.9992 |
| SLYNTVAPL (143) | 2.34E-07 | 1.20E-09 | 1.35E+05 | 6.11E+02 | 3.16E-02 | 7.71E-05 | 0.3155 | 0.9969 |
| SLYNTVAAL (144) | 8.50E-09 | 1.51E-10 | 1.14E+05 | 1.75E+02 | 9.69E-04 | 1.72E-05 | 0.3504 | 0.9991 |
| SLYNTVAVL (145) | 6.98E-09 | 1.19E-10 | 1.05E+05 | 1.20E+02 | 7.31E-04 | 1.25E-05 | 0.1881 | 0.9995 |
| SLYNTVALL (146) | 1.58E-08 | 1.20E-10 | 9.58E+04 | 1.03E+02 | 1.51E-03 | 1.14E-05 | 0.1259 | 0.9996 |
| SLYNTVAIL (147) | 4.16E-09 | 7.48E-10 | 9.74E+04 | 6.62E+02 | 4.05E-04 | 7.28E-05 | 5.8607 | 0.9834 |
| SLYNTVAML (148) | 7.69E-09 | 5.22E-10 | 9.75E+04 | 4.63E+02 | 7.50E-04 | 5.08E-05 | 2.7181 | 0.9922 |
| SLYNTVAFL (149) | 1.93E-07 | 1.68E-09 | 9.29E+04 | 6.77E+02 | 1.80E-02 | 8.45E-05 | 0.9456 | 0.9906 |
| SLYNTVAYL (150) | 4.00E-07 | 3.75E-09 | 9.61E+04 | 8.32E+02 | 3.85E-02 | 1.39E-04 | 0.2451 | 0.994 |
| SLYNTVAWL (151) | 2.09E-07 | 1.94E-09 | 9.65E+04 | 7.69E+02 | 2.01E-02 | 9.70E-05 | 1.0358 | 0.9893 |
| SLYNTVAHL (152) | 1.09E-08 | 5.55E-10 | 9.19E+04 | 4.47E+02 | 1.00E-03 | 5.07E-05 | 2.6388 | 0.9925 |
| SLYNTVAKL (153) | 1.73E-08 | 2.87E-10 | 1.02E+05 | 2.76E+02 | 1.77E-03 | 2.90E-05 | 0.9054 | 0.9975 |
| SLYNTVARL (154) | 7.93E-09 | 3.98E-10 | 1.06E+05 | 4.06E+02 | 8.37E-04 | 4.19E-05 | 2.1201 | 0.9946 |
| SLYNTVAQL (155) | 1.59E-08 | 6.14E-10 | 1.01E+05 | 5.74E+02 | 1.61E-03 | 6.13E-05 | 4.0059 | 0.9888 |
| SLYNTVANL (156) | 1.08E-08 | 6.43E-10 | 1.01E+05 | 6.03E+02 | 1.09E-03 | 6.46E-05 | 4.5943 | 0.9874 |
| SLYNTVAEL (157) | 4.73E-08 | 2.37E-10 | 9.22E+04 | 1.79E+02 | 4.36E-03 | 2.02E-05 | 0.291 | 0.999 |
| SLYNTVADL (158) | 2.12E-08 | 3.17E-10 | 8.90E+04 | 2.40E+02 | 1.88E-03 | 2.77E-05 | 0.6889 | 0.9979 |
| SLYNTVASL (159) | 4.68E-09 | 2.55E-10 | 1.09E+05 | 2.71E+02 | 5.08E-04 | 2.76E-05 | 0.918 | 0.9977 |
| SLYNTVATG (160) | 7.71E-09 | 4.30E-10 | 1.01E+05 | 4.05E+02 | 7.79E-04 | 4.34E-05 | 2.1199 | 0.9943 |
| SLYNTVATP (161) | 5.03E-08 | 1.57E-09 | 3.41E+04 | 3.34E+02 | 1.72E-03 | 5.08E-05 | 0.6961 | 0.9945 |
| SLYNTVATA (162) | 6.74E-09 | 4.88E-10 | 1.13E+05 | 5.56E+02 | 7.61E-04 | 5.49E-05 | 3.6905 | 0.9904 |
| SLYNTVATV (163) | 8.41E-09 | 6.00E-10 | 1.04E+05 | 5.95E+02 | 8.76E-04 | 6.23E-05 | 4.752 | 0.988 |

TABLE 3-continued bs-868Z11-CD3 binding affinity for SV9 peptide SLYNTVATL (SEQ ID NO: 5) and peptides from positional scanning library (SEQ ID NOS: 16-177). Table includes $K_D$, $K_{on}$ and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|
| SLYNTVATI (164) | 6.70E-09 | 2.87E-10 | 1.13E+05 | 3.25E+02 | 7.53E-04 | 3.22E-05 | 1.2712 | 0.9968 |
| SLYNTVATM (165) | 7.45E-09 | 2.48E-10 | 9.88E+04 | 2.26E+02 | 7.36E-04 | 2.44E-05 | 0.6922 | 0.9982 |
| SLYNTVATF (166) | 1.19E-08 | 2.46E-10 | 7.18E+04 | 1.37E+02 | 8.51E-04 | 1.76E-05 | 0.2228 | 0.9992 |
| SLYNTVATY (167) | 1.02E-08 | 3.37E-10 | 7.11E+04 | 1.85E+02 | 7.24E-04 | 2.39E-05 | 0.4625 | 0.9985 |
| SLYNTVATW (168) | 3.32E-08 | 5.59E-10 | 3.70E+04 | 1.34E+02 | 1.23E-03 | 2.02E-05 | 0.0824 | 0.9991 |
| SLYNTVATH (169) | 1.37E-08 | 3.64E-10 | 4.75E+04 | 1.19E+02 | 6.51E-04 | 1.72E-05 | 0.089 | 0.9993 |
| SLYNTVATK (170) | 4.57E-08 | 1.20E-09 | 2.70E+04 | 2.00E+02 | 1.23E-03 | 3.11E-05 | 0.0929 | 0.9982 |
| SLYNTVATR (171) | 5.71E-09 | 2.30E-10 | 9.59E+04 | 1.99E+02 | 5.48E-04 | 2.20E-05 | 0.5532 | 0.9986 |
| SLYNTVATQ (172) | 5.88E-09 | 3.12E-10 | 8.96E+04 | 2.41E+02 | 5.27E-04 | 2.79E-05 | 0.7397 | 0.9978 |
| SLYNTVATN (173) | 9.10E-09 | 3.77E-10 | 9.76E+04 | 3.36E+02 | 8.88E-04 | 3.67E-05 | 1.5971 | 0.9961 |
| SLYNTVATE (174) | 6.96E-06 | 9.43E-06 | 3.79E+02 | 5.13E+02 | 2.64E-03 | 8.02E-05 | 0.1997 | 0.9908 |
| SLYNTVATD (175) | 7.18E-06 | 8.48E-06 | 3.95E+02 | 4.67E+02 | 2.83E-03 | 7.30E-05 | 0.1137 | 0.9924 |
| SLYNTVATS (176) | 7.19E-09 | 2.13E-10 | 1.16E+05 | 2.54E+02 | 8.33E-04 | 2.46E-05 | 0.7637 | 0.9981 |
| SLYNTVATT (177) | 5.66E-09 | 1.27E-10 | 1.12E+05 | 1.42E+02 | 6.32E-04 | 1.41E-05 | 0.2627 | 0.9994 |

TABLE 4

Cross-reactive peptide ligand search motif for bs-868Z11-CD3 based on the affinities measured using the positional scanning library. All amino acids of the 19 proteinogenic amino acids investigated at each position that increased the respective affinity of the bsTCR above 50 nM were removed to reach the search motif.

| Peptide Position | Permitted Amino Acids |
|---|---|
| 1 | GPAVLIMKRNDST |
| 2 | GAVLIMFYHQNEST |
| 3 | FYW |
| 4 | N |
| 5 | VLIMT |
| 6 | PVLIMT |
| 7 | GPANS |
| 8 | GAVLIMHKRQNEDST |
| 9 | GAVLIMFYWHKRQNST |

Figure 12:
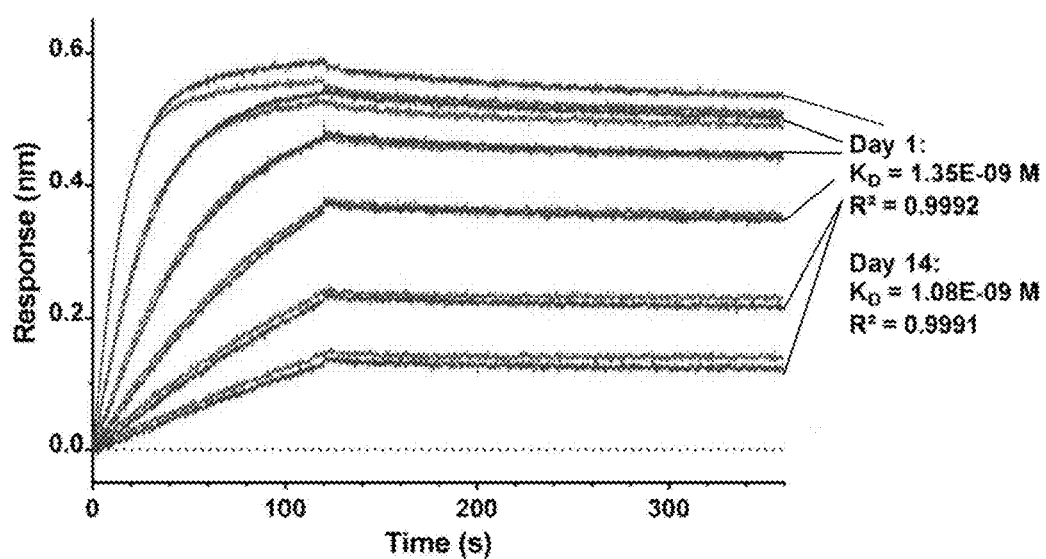
FIG. 12 shows octet affinity measurements for Y84C/A139C HLA-A*02:01 SLYNTVATL (SEQ ID NO: 5) pMHC with immobilized bs-868Z11-CD3 directly after exchange and after 2 weeks of storage at 4° C. Both measurements were performed using 1:2 analyte dilution series starting at 277.8 nM.

Soluble Y84C/A139C HLA-A*02:01 pMHC preparations can be stored for at least 2 weeks at 4° C. without loss of quality and used for multiple analyses (FIG. 12; Day 1: $K_D=1.35E^{-09}$ M, $R^2=0.9992$; Day 14: $K_D=1.08E^{-09}$ M, $R^2=0.9991$).

The 868Z11 TCR displayed an expected pattern of recognition: changes of amino acids between positions 3 to 7 had the biggest influence on the bsTCR binding affinity. Interestingly, only one amino acid change resulted in an increased binding affinity by bs-868Z11-CD3 compared to the interaction with the wild type peptide, showcasing the remarkable affinity the TCR has for the target in its affinity maturated state. This behavior can also be graphically illustrated when visualizing the binding motif as Seq2Logo graph (FIG. 4B) (27).

21. Identification of Peptide Ligands Cross-Reactive with Bs-868Z11-CD3

The inventors further wanted to explore whether they could use the generated binding motif to identify cross-reactive peptide ligands from the human genome. The inventors created a peptide ligand search motif from the affinity dataset by introducing an exemplary $K_d$ threshold of 50 nM: all single amino acid substitutions increasing the bs-868Z11-CD3 $K_d$ above that threshold were excluded from the motif (Table 4). Based on this motif the inventors performed a search in the NCBI human non-redundant protein sequence database for nonamer sequences matching combinations allowed by the motif. The search identified over 400 hits within the human genome, with sequence identity to the wild type sequence SLYNTVATL (SEQ ID NO: 5) ranging from 1 to 6 identical positions. 140 peptides were selected, sampled to be representative of the sequence identity distribution in the larger group, synthesized and used for affinity measurements (Table 5; SEQ ID NOS: 178-317). The inventors were able to detect binding affinities of single digit μM $K_d$s or higher for 91 of those peptides.

TABLE 5 the bs-868Z11-CD3 binding motif. Peptide sequences and associated genes according to the NCbi data base are reported and peptides are sorted by decreasing $K_d$s. Table includes $K_D$, $K_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | KD (M) | KD Error | $k_{on}$ (M⁻¹s⁻¹) | $k_{on}$ Error | $k_{off}$ (s⁻¹) | $k_{off}$ Error | Full X² | Full R² |
|---|---|---|---|---|---|---|---|---|---|
| RVYNTVPLV (178) | HIPK3 | 1.32E-08 | 1.76E-10 | 9.50E+04 | 1.69E+02 | 1.26E-03 | 1.66E-05 | 0.2908 | 0.9993 |
| RMYNLVSRI (179) | CUL1 | 1.91E-08 | 2.52E-10 | 9.25E+04 | 2.28E+02 | 1.76E-03 | 2.29E-05 | 0.5429 | 0.9986 |
| SLYNMVPSI (180) | OVOS | 1.97E-08 | 1.71E-10 | 1.31E+05 | 2.89E+02 | 2.57E-03 | 2.16E-05 | 0.586 | 0.9987 |
| TVYNMVPSI (181) | OVOS | 2.07E-08 | 1.54E-10 | 1.28E+05 | 2.50E+02 | 2.66E-03 | 1.91E-05 | 0.4228 | 0.999 |
| ALYNVIAMA (182) | SECISBP2L | 2.11E-08 | 1.51E-10 | 9.28E+04 | 2.25E+02 | 1.96E-03 | 1.32E-05 | 0.114 | 0.9997 |
| AIYNLLPDI (183) | NCAPD2 | 2.33E-08 | 1.82E-10 | 1.01E+05 | 1.90E+02 | 2.36E-03 | 1.79E-05 | 0.3299 | 0.9992 |
| STYNLVSTS (184) | KIAA2018 | 2.47E-08 | 2.16E-10 | 7.07E+04 | 1.28E+02 | 1.75E-03 | 1.49E-05 | 0.1772 | 0.9995 |
| SVYNMVPSI (185) | OVOS2 | 2.68E-08 | 1.96E-10 | 1.32E+05 | 3.26E+02 | 3.53E-03 | 2.43E-05 | 0.6471 | 0.9984 |
| RTYNVLAIL (186) | ATP8B1 | 3.11E-08 | 1.55E-10 | 7.54E+04 | 9.93E+01 | 2.34E-03 | 1.12E-05 | 0.0937 | 0.9997 |
| SVYNLVSIA (187) | KPTN | 3.65E-08 | 2.01E-10 | 7.97E+04 | 2.13E+02 | 2.91E-03 | 1.40E-05 | 0.0926 | 0.9997 |
| RAYNLIGTV (188) | LOC100128501 | 3.72E-08 | 1.71E-10 | 8.94E+04 | 1.40E+02 | 3.33E-03 | 1.43E-05 | 0.1721 | 0.9995 |
| ALFNLIPVG (189) | FGF12 | 3.83E-08 | 3.22E-10 | 6.64E+04 | 1.71E+02 | 2.54E-03 | 2.04E-05 | 0.266 | 0.999 |
| RIYNVIGTL (190) | FOLH1, FOLH1B | 4.53E-08 | 3.00E-10 | 5.75E+04 | 1.28E+02 | 2.61E-03 | 1.62E-05 | 0.1095 | 0.9994 |
| RIYNVVGTI (191) | NAALAD2 | 5.15E-08 | 4.13E-10 | 5.94E+04 | 1.81E+02 | 3.06E-03 | 2.27E-05 | 0.2723 | 0.9989 |
| TLFNLVPNS (192) | CLASP2 | 5.40E-08 | 3.31E-10 | 9.76E+04 | 2.90E+02 | 5.28E-03 | 2.82E-05 | 0.4822 | 0.9981 |

TABLE 5-continued the bs-868Z11-CD3 binding motif. Peptide sequences and associated genes according to the NCbi data base are reported and peptides are sorted by decreasing $K_D$s. Table includes $K_D$, $k_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | $K_D$ (M) | $K_D$ Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|---|
| SLFNVISIL (193) | KCNK12, KCNK13 | 5.83E-08 | 3.11E-10 | 6.94E+04 | 1.64E+02 | 4.05E-03 | 1.94E-05 | 0.2068 | 0.9992 |
| STFNLVAIS (194) | CCKAR | 6.06E-08 | 2.91E-10 | 4.96E+04 | 9.98E+01 | 3.01E-03 | 1.31E-05 | 0.0436 | 0.9996 |
| TLFNLIPVG (195) | FGF12, FGF13, FGF14 | 6.32E-08 | 3.97E-10 | 6.72E+04 | 1.98E+02 | 4.25E-03 | 2.36E-05 | 0.3044 | 0.9988 |
| TIFNLIPNS (196) | CLASP1 | 6.41E-08 | 2.67E-10 | 8.97E+04 | 1.99E+02 | 5.75E-03 | 2.03E-05 | 0.2655 | 0.999 |
| ALYNVLAKV (197) | IFFO1, IFFO2 | 6.59E-08 | 2.96E-10 | 1.02E+05 | 2.63E+02 | 6.75E-03 | 2.49E-05 | 0.3602 | 0.9986 |
| AVFNLLPHT (198) | SMYD4 | 7.11E-08 | 2.72E-10 | 8.53E+04 | 1.82E+02 | 6.07E-03 | 1.93E-05 | 0.2344 | 0.9991 |
| RMYNLLGHM (199) | ZNF710 | 8.71E-08 | 7.55E-10 | 5.30E+04 | 2.55E+02 | 4.62E-03 | 3.33E-05 | 0.2278 | 0.9977 |
| STWNTPPNM (200) | KIAA0922 | 8.98E-08 | 3.45E-10 | 9.05E+04 | 2.28E+02 | 8.13E-03 | 2.36E-05 | 0.2591 | 0.9989 |
| NIYNLIAII (201) | BICD2 | 9.32E-08 | 3.91E-10 | 1.06E+05 | 3.10E+02 | 9.84E-03 | 2.95E-05 | 0.3894 | 0.9983 |
| RIYNLPPEL (202) | WRAP53 | 9.95E-08 | 3.78E-10 | 9.47E+04 | 2.51E+02 | 9.42E-03 | 2.56E-05 | 0.3026 | 0.9988 |
| TTFNLPSAA (203) | WDR17 | 1.02E-07 | 6.71E-10 | 7.87E+04 | 3.47E+02 | 8.04E-03 | 3.91E-05 | 0.579 | 0.997 |
| MFFNVIAIV (204) | UGGT2 | 1.06E-07 | 1.29E-09 | 5.21E+04 | 3.95E+02 | 5.52E-03 | 5.23E-05 | 0.0772 | 0.9934 |
| SLWNTVSGI (205) | HHLA1 | 1.08E-07 | 5.04E-10 | 8.88E+04 | 2.94E+02 | 9.60E-03 | 3.14E-05 | 0.3873 | 0.9982 |
| MLWNLLALR (206) | COX7A2 | 1.17E-07 | 1.03E-08 | 1.26E+06 | 1.05E+05 | 1.47E-01 | 4.25E-03 | 0.0448 | 0.9675 |
| VFWNLLPTV (207) | C12orf74 | 1.20E-07 | 7.20E-10 | 1.24E+05 | 5.97E+02 | 1.49E-02 | 5.29E-05 | 0.9116 | 0.9955 |
| STFNTTSNG (208) | QSER1 | 1.52E-07 | 6.60E-09 | 1.76E+05 | 7.05E+03 | 2.67E-02 | 4.39E-04 | 0.0311 | 0.9225 |
| GFFNLLSHV (209) | PCP2 | 1.59E-07 | 9.88E-09 | 6.24E+05 | 3.64E+04 | 9.94E-02 | 2.08E-03 | 0.0321 | 0.9717 |
| LLYNVPAVA (210) | APP | 1.67E-07 | 1.27E-08 | 7.41E+05 | 5.29E+04 | 1.24E-01 | 3.21E-03 | 0.0164 | 0.9712 |
| ALFNTISQG (211) | VTA1 | 1.83E-07 | 8.26E-10 | 7.15E+04 | 2.68E+02 | 1.31E-02 | 3.28E-05 | 0.2214 | 0.9984 |
| TTFNTLAGS (212) | MUC16 | 1.97E-07 | 8.70E-10 | 9.03E+04 | 3.44E+02 | 1.78E-02 | 3.98E-05 | 0.1556 | 0.9981 |
| SLWNLLGNA (213) | LMAN2L | 2.14E-07 | 3.02E-08 | 1.02E+06 | 1.35E+05 | 2.19E-01 | 1.07E-02 | 0.0324 | 0.952 |
| SLYNLLNLT (214) | SLC4A5 | 2.19E-07 | 8.40E-10 | 6.75E+04 | 2.24E+02 | 1.48E-02 | 2.85E-05 | 0.094 | 0.9988 |
| GVWNLLSIV (215) | ZSWIM8 | 2.52E-07 | 4.59E-08 | 1.09E+06 | 1.86E+05 | 2.74E-01 | 1.73E-02 | 0.0545 | 0.9403 |

TABLE 5-continued the bs-868Z11-CD3 binding motif. Peptide sequences and associated genes according to the NCbi data base are reported and peptides are sorted by decreasing $K_D$s. Table includes $K_D$, $k_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | $K_D$ (M) | $K_D$ Error | $k_{on}$ (M$^{-1}$s$^{-1}$) | $k_{on}$ Error | $k_{off}$ (s$^{-1}$) | $k_{off}$ Error | Full $X^2$ | Full $R^2$ |
|---|---|---|---|---|---|---|---|---|---|
| ALFNVVNSI (216) | SLC38A11 | 2.55E-07 | 2.10E-09 | 6.83E+04 | 4.99E+02 | 1.74E-02 | 6.59E-05 | 0.2897 | 0.9956 |
| VIYNLLGLA (217) | SH3TC2 | 2.64E-07 | 1.88E-09 | 1.07E+05 | 7.25E+02 | 2.83E-02 | 5.92E-05 | 0.2115 | 0.9983 |
| SIFNIVAIA (218) | GPR50 | 2.84E-07 | 1.60E-09 | 4.44E+04 | 2.37E+02 | 1.26E-02 | 2.25E-05 | 0.0369 | 0.9995 |
| TVYNTVSEG (219) | SLC39A6 | 3.04E-07 | 2.50E-09 | 4.71E+04 | 3.50E+02 | 1.43E-02 | 4.99E-05 | 0.2538 | 0.997 |
| DLWNTLSSL (220) | EFCAB13, ITGB3 | 3.39E-07 | 2.60E-08 | 4.15E+05 | 3.02E+04 | 1.41E-01 | 3.55E-03 | 0.0238 | 0.9752 |
| IFFNLLAVL (221) | POMT1 | 3.50E-07 | 4.75E-08 | 8.47E+05 | 1.08E+05 | 2.97E-01 | 1.35E-02 | 0.023 | 0.9688 |
| DLFNLLPDV (222) | PSMD7 | 3.60E-07 | 1.08E-08 | 7.69E+04 | 2.15E+03 | 2.77E-02 | 3.14E-04 | 0.0881 | 0.9367 |
| LSWNVVPNA (223) | SPCS3 | 3.67E-07 | 2.91E-08 | 4.13E+05 | 3.09E+04 | 1.52E-01 | 3.89E-03 | 0.0234 | 0.9734 |
| MLWNLLALH (224) | COX7A2P2 | 3.67E-07 | 2.04E-08 | 1.07E+06 | 4.75E+04 | 3.94E-01 | 1.33E-02 | 0.1159 | 0.9595 |
| TIFNTVNTS (225) | TIMMDC1 | 3.87E-07 | 2.77E-09 | 4.20E+04 | 2.80E+02 | 1.63E-02 | 4.19E-05 | 0.0304 | 0.9978 |
| KTFNLIPAV (226) | MRPL4 | 4.13E-07 | 2.59E-09 | 1.12E+05 | 6.52E+02 | 4.62E-02 | 1.07E-04 | 0.1185 | 0.9979 |
| NLFNVTPLI (227) | ZNF66P | 4.28E-07 | 1.38E-07 | 1.05E+06 | 3.19E+05 | 4.49E-01 | 4.68E-02 | 0.0447 | 0.9139 |
| SYWNIISTV (228) | OR2D3 | 4.39E-07 | 4.84E-09 | 4.56E+04 | 4.74E+02 | 2.00E-02 | 7.23E-05 | 0.1373 | 0.9952 |
| GVENLIAVL (229) | AC002365.5, LOC100288814 | 4.59E-07 | 4.94E-09 | 7.59E+04 | 7.70E+02 | 3.48E-02 | 1.26E-04 | 0.3268 | 0.9946 |
| RLFNITSSA (230) | IFITM10 | 4.74E-07 | 4.12E-08 | 2.51E+05 | 2.08E+04 | 1.19E-01 | 3.08E-03 | 0.0167 | 0.9706 |
| NLWNLVAVI (231) | WDR17 | 4.97E-07 | 1.16E-08 | 2.07E+05 | 4.34E+03 | 1.03E-01 | 1.04E-03 | 0.256 | 0.9836 |
| RIFNLIGMM (232) | HCN1, HCN3 | 4.98E-07 | 1.26E-08 | 2.29E+04 | 5.51E+02 | 1.14E-02 | 8.55E-05 | 0.0712 | 0.9889 |
| RLFNVVSRG (233) | TRPV2 | 5.02E-07 | 6.55E-09 | 6.50E+04 | 8.05E+02 | 3.26E-02 | 1.34E-04 | 0.1875 | 0.9931 |
| LVFNVIPTL (234) | ABCB6 | 5.35E-07 | 3.99E-09 | 1.33E+05 | 9.21E+02 | 7.13E-02 | 2.00E-04 | 0.0445 | 0.9982 |
| TTWNILSSA (235) | COX1 | 5.36E-07 | 4.08E-08 | 2.26E+05 | 1.65E+04 | 1.21E-01 | 2.63E-03 | 0.0214 | 0.9794 |
| KLFNVLSTL (236) | NUP210P2 | 5.76E-07 | 3.35E-08 | 2.97E+05 | 1.65E+04 | 1.71E-01 | 2.83E-03 | 0.0131 | 0.9912 |
| RVYNLTAKS (237) | VWA3B | 5.95E-07 | 4.57E-09 | 4.53E+04 | 3.35E+02 | 2.69E-02 | 5.65E-05 | 0.0219 | 0.9981 |
| LTFNTISLS (238) | ENTHD1 | 7.09E-07 | 2.12E-07 | 4.78E+05 | 1.37E+05 | 3.39E-01 | 2.72E-02 | 0.0387 | 0.929 |

TABLE 5-continued the bs-868Z11-CD3 binding motif. Peptide sequences and associated genes according to the NCbi data base are reported and peptides are sorted by decreasing $K_d$s. Table includes $K_D$, $k_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|---|
| AQFNLLSST (239) | TP73 | 7.13E-07 | 9.97E-09 | 8.59E+04 | 1.15E+03 | 6.12E-02 | 2.58E-04 | 0.1658 | 0.9947 |
| VVYNVLSEL (240) | SP100, SP140L | 7.35E-07 | 6.29E-08 | 1.84E+05 | 1.52E+04 | 1.35E-01 | 2.89E-03 | 0.0255 | 0.9785 |
| KVYNTPSTS (241) | AEBP2 | 7.51E-07 | 1.39E-08 | 1.71E+05 | 2.91E+03 | 1.28E-01 | 9.13E-04 | 0.0718 | 0.9945 |
| GIFNIIPST (242) | CAPN7 | 7.90E-07 | 8.67E-09 | 1.32E+05 | 1.36E+03 | 1.04E-01 | 4.00E-04 | 0.0364 | 0.9979 |
| NIYNTLSGL (243) | UBR4 | 8.73E-07 | 1.71E-08 | 1.59E+05 | 2.89E+03 | 1.38E-01 | 9.89E-04 | 0.0564 | 0.9947 |
| RLFNLTSTF (244) | FLJ44715, FUT11 | 9.32E-07 | 2.82E-08 | 1.72E+05 | 4.83E+03 | 1.60E-01 | 1.79E-03 | 0.0525 | 0.9894 |
| TVWNTLSSL (245) | DNAH9 | 9.39E-07 | 1.22E-08 | 4.52E+04 | 5.73E+02 | 4.25E-02 | 1.20E-04 | 0.0344 | 0.9971 |
| RLFNMLSAV (246) | CFAP221, PCDP1 | 9.71E-07 | 3.06E-08 | 1.73E+05 | 5.09E+03 | 1.68E-01 | 1.94E-03 | 0.0714 | 0.9892 |
| SIWNVTAIA (247) | HTR5A | 1.10E-06 | 5.12E-07 | 3.21E+05 | 1.45E+05 | 3.54E-01 | 3.47E-02 | 0.0576 | 0.9051 |
| ALFNLMSGI (248) | EGR4 | 1.19E-06 | 3.21E-08 | 9.57E+04 | 2.48E+03 | 1.14E-01 | 8.53E-04 | 0.0645 | 0.9931 |
| IVYNLLSAM (249) | SLC39A10 | 1.30E-06 | 1.62E-07 | 1.61E+05 | 1.98E+04 | 2.10E-01 | 4.82E-03 | 0.0245 | 0.987 |
| ISFNMLPSI (250) | GPR98 | 1.37E-06 | 4.65E-08 | 1.24E+05 | 4.04E+03 | 1.70E-01 | 1.70E-03 | 0.0581 | 0.991 |
| NTYNILPGS (251) | C9orf173 | 1.38E-06 | 1.17E-07 | 1.14E+05 | 9.57E+03 | 1.57E-01 | 2.30E-03 | 0.025 | 0.9925 |
| RLWNMVNVT (252) | IL12RB2 | 1.39E-06 | 2.57E-07 | 1.52E+05 | 2.77E+04 | 2.11E-01 | 6.87E-03 | 0.049 | 0.9763 |
| SAFNITSLI (253) | WAC | 1.41E-06 | 3.21E-07 | 1.65E+05 | 3.70E+04 | 2.32E-01 | 9.29E-03 | 0.0314 | 0.9682 |
| NIFNLPNIV (254) | OMD | 1.48E-06 | 6.62E-07 | 4.19E+05 | 1.85E+05 | 6.20E-01 | 4.90E-02 | 0.0905 | 0.9596 |
| GVYNLPGAS (255) | GPX2 | 1.58E-06 | 3.07E-07 | 1.17E+05 | 2.23E+04 | 1.84E-01 | 5.65E-03 | 0.0488 | 0.9756 |
| GTYNVISLV (256) | TRPC4, TRPC5 | 1.64E-06 | 4.18E-07 | 1.23E+05 | 3.10E+04 | 2.02E-01 | 8.00E-03 | 0.0666 | 0.965 |
| SIFNTLSDI (257) | SGSM3 | 1.97E-06 | 5.86E-08 | 4.07E+04 | 1.20E+03 | 8.01E-02 | 3.78E-04 | 0.0856 | 0.9957 |
| TIFNILSGI (258) | ABCA3 | 2.66E-06 | 2.37E-07 | 4.68E+04 | 4.13E+03 | 1.24E-01 | 1.66E-03 | 0.1728 | 0.9807 |
| LLFNLISSS (259) | MON1A | 2.79E-06 | 2.57E-06 | 1.51E+05 | 1.38E+05 | 4.20E-01 | 4.10E-02 | 0.0599 | 0.9183 |
| RTFNLTAGS (260) | PDXDC1 | 2.85E-06 | 5.89E-07 | 4.63E+04 | 9.54E+03 | 1.32E-01 | 2.56E-03 | 0.0356 | 0.9845 |
| TVFNILPGG (261) | PAFAH2 | 3.23E-06 | 1.06E-06 | 3.69E+04 | 1.21E+04 | 1.19E-01 | 3.22E-03 | 0.025 | 0.968 |

TABLE 5-continued the bs-868Z11-CD3 binding motif. Peptide sequences and associated genes according to the NCbi data base are reported and peptides are sorted by decreasing $K_d$s. Table includes $K_D$, $K_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|---|
| GLFNIPPAS (262) | CYP2S1 | 3.91E-06 | 4.13E-06 | 8.52E+04 | 8.97E+04 | 3.33E-01 | 2.74E-02 | 0.0395 | 0.9216 |
| RMFNIISDS (263) | RASA1 | 3.99E-06 | 4.08E-07 | 1.51E+04 | 1.54E+03 | 6.02E-02 | 4.39E-04 | 0.0509 | 0.9862 |
| TTFNIVGTT (264) | GABRA3 | 6.79E-06 | 3.10E-06 | 8.68E+03 | 3.96E+03 | 5.89E-02 | 8.72E-04 | 0.0351 | 0.9743 |
| ALFNLMSGV (265) | EGR4 | 7.87E-06 | 1.14E-05 | 3.17E+04 | 4.60E+04 | 2.50E-01 | 1.45E-02 | 0.1115 | 0.9454 |
| SVFNITAIA (266) | MTNR1B | 1.96E-05 | 2.39E-04 | 2.58E+04 | 3.15E+05 | 5.06E-01 | 1.06E-01 | 0.2805 | 0.7869 |
| KIYNTPSAS (267) | NCAM1 | 2.56E-05 | 2.88E-05 | 8.86E+03 | 9.95E+03 | 2.27E-01 | 5.62E-03 | 0.2474 | 0.9662 |
| LLYNLLGSS (268) | ABCC9 | 1.41E-04 | 6.82E-03 | 3.21E+03 | 1.55E+05 | 4.54E-01 | 5.27E-02 | 0.1153 | 0.9007 |
| SLYNMMGEA (269) | TMTC2 | No fit | | | | | | | |
| SLWNLMGNA (270) | LMAN2L | No fit | | | | | | | |
| GLYNIVGNA (271) | SUMF1 | No fit | | | | | | | |
| LTWNLTPKA (272) | DLEC1 | No fit | | | | | | | |
| LIFNVTGLA (273) | ZDHHC23 | No fit | | | | | | | |
| SIFNITGIA (274) | MTNR1A | No fit | | | | | | | |
| LTFNLVSDA (275) | CASP8AP2 | No fit | | | | | | | |
| MQWNILAQA (276) | CCRN4L | No fit | | | | | | | |
| LSWNLVPEA (277) | COL7A1 | No fit | | | | | | | |
| DLWNTLSEA (278) | TRHDE | No fit | | | | | | | |
| GLFNIPPAF (279) | CYP2S1 | No fit | | | | | | | |
| LIWNILASF (280) | TTC29 | No fit | | | | | | | |
| LLFNMLPGG (281) | EXT2 | No fit | | | | | | | |
| LVYNIMSSG (282) | FAM120B | No fit | | | | | | | |
| IIYNVPGTG (283) | RNF133 | No fit | | | | | | | |
| VIYNVTSDG (284) | TTN | No fit | | | | | | | |

TABLE 5-continued the bs-868Z11-CD3 binding motif. Peptide sequences and associated genes according to the NCbi data base are reported and peptides are sorted by decreasing $K_D$s. Table includes $K_D$, $K_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|---|
| GTFNLPSDG (285) | BAG6 | No fit | | | | | | | |
| KLWNTLNLI (286) | ENPP5 | No fit | | | | | | | |
| LMWNIISII (287) | VTCN1 | No fit | | | | | | | |
| GLFNTTSNI (288) | SEMA3E | No fit | | | | | | | |
| LIFNTLSLI (289) | PDCD6IP | No fit | | | | | | | |
| SVFNLMNAI (290) | SLC38A6 | No fit | | | | | | | |
| LTFNILGQI (291) | DOCK11 | No fit | | | | | | | |
| GLFNMVSSL (292) | RRN3 | No fit | | | | | | | |
| KIFNIIINSL (293) | FER1L5 | No fit | | | | | | | |
| AVWNVLGNL (294) | BAG5 | No fit | | | | | | | |
| KVFNIVSDL (295) | FSIP2 | No fit | | | | | | | |
| DLWNVVSHL (296) | DDX60L | No fit | | | | | | | |
| LQFNTVSKL (297) | JAM2 | No fit | | | | | | | |
| MSFNTVSEL (298) | ZNF33A, ZNF33B | No fit | | | | | | | |
| ASWNIVNLL (299) | TRPA1 | No fit | | | | | | | |
| ISFNIISAL (300) | MS4A18 | No fit | | | | | | | |
| AFFNILNEL (301) | FNBP1L | No fit | | | | | | | |
| LVFNLLPIM (302) | ABCB7 | No fit | | | | | | | |
| KIFNTVPDM (303) | ARHGAP26 | No fit | | | | | | | |
| MLFNLIGLS (304) | OR10J1 | No fit | | | | | | | |
| LLFNLPPGS (305) | VGLL1 | No fit | | | | | | | |
| MTFNLIGES (306) | CR1, CR1L | No fit | | | | | | | |
| KVYNIPGIS (307) | KLI1L10 | No fit | | | | | | | |

TABLE 5-continued the bs-868Z11-CD3 binding motif. Peptide sequences and associated genes according to the NCbi data base are reported and peptides are sorted by decreasing $K_d$s. Table includes $K_D$, $K_{on}$, and $k_{off}$ values determined by curve fittings following a 1:1 Langmuir binding model using the Fortébio Data Analysis HT 10.0.3.7 software. Respective errors are reported as well as accuracy of the fit according to the model. Peptides reported as "No fit" had no evaluable curves reaching at least a peak signal of 0.05 nm at any concentration.

| Peptide | Associated Gene | KD (M) | KD Error | $k_{on}$ (M$^{-1}$s$^{-1}$) | $k_{on}$ Error | $k_{off}$ (s$^{-1}$) | $k_{off}$ Error | Full X$^2$ | Full R$^2$ |
|---|---|---|---|---|---|---|---|---|---|
| GIYNIPGDS (308) | TNS1 | No fit | | | | | | | |
| GLYNLMNIT (309) | INSR | No fit | | | | | | | |
| LTWNMINTT (310) | LRIT3 | No fit | | | | | | | |
| IVFNVLSDT (311) | HCN3 | No fit | | | | | | | |
| IVFNVVSDT (312) | HCN2, HCN4 | No fit | | | | | | | |
| LIFNITASV (313) | SVEP1 | No fit | | | | | | | |
| IVFNLTNNV (314) | MNAT1 | No fit | | | | | | | |
| KSFNVLSSV (315) | ZNF557 | No fit | | | | | | | |
| LAFNILGMV (316) | SLC46A1 | No fit | | | | | | | |
| VSWNITGTV (317) | SEH1L | No fit | | | | | | | |

One of them, ALYNVLAKV (SEQ ID NO: 1), was worth of special notice. It was selected as a theoretical peptide but found in addition on tissue samples and cell lines according to the XPRESIDENT® immunopeptidomics database. This database combines quantitative HLA peptidomics based on LC-MS analysis and quantitative transcriptomics provided by RNAseq from healthy tissues and tumor tissues to identify peptides presented exclusively or predominately on tumor tissue (28, 29).

Figure 4C:
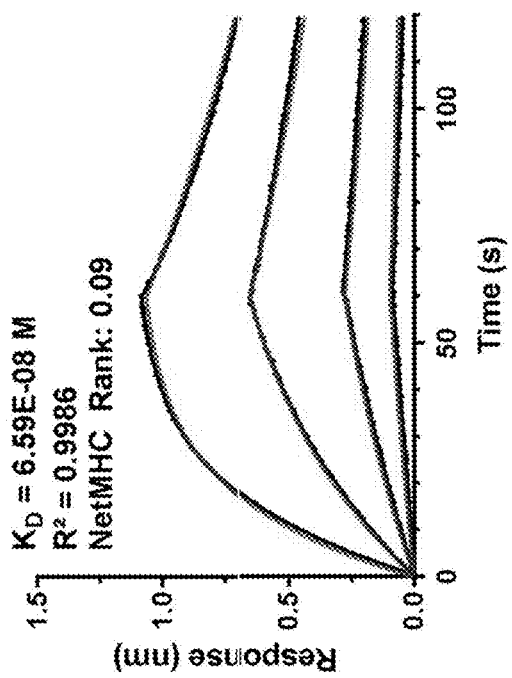
Figure 4B:
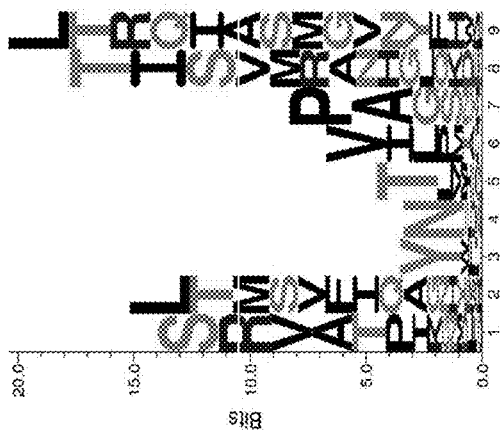

ALYNVLAKV (SEQ ID NO: 1), an antigen from intermediate filament family orphan 1 or 2 (IFFO1/2), was detected on multiple healthy tissue and tumor tissue samples, ranging from head and neck, spleen, or kidney to non-small cell lung carcinoma or renal cell carcinoma. The pMHC-bsTCR binding affinity was measured with a $K_D$ of 65.9 nM (FIG. 4c). The inventors were able to identify a second LC-MS detected peptide, KTFNLIPAV (SEQ ID NO: 226), with a lower $K_d$ of 413 nM detected on three tumor tissue samples.

22. Correlation of bsTCR Affinity with T Cell Activation

Figure 5A:
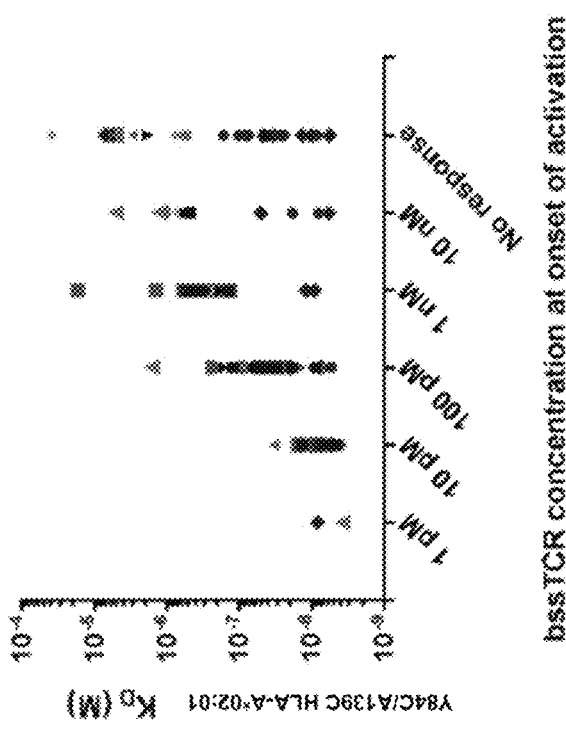
FIGS. 5A-5E show the result of coincubation assays with peptide loaded target cells, Jurkat effector cells and bs-868Z11-CD3 at six different concentrations.
Figure 5B:
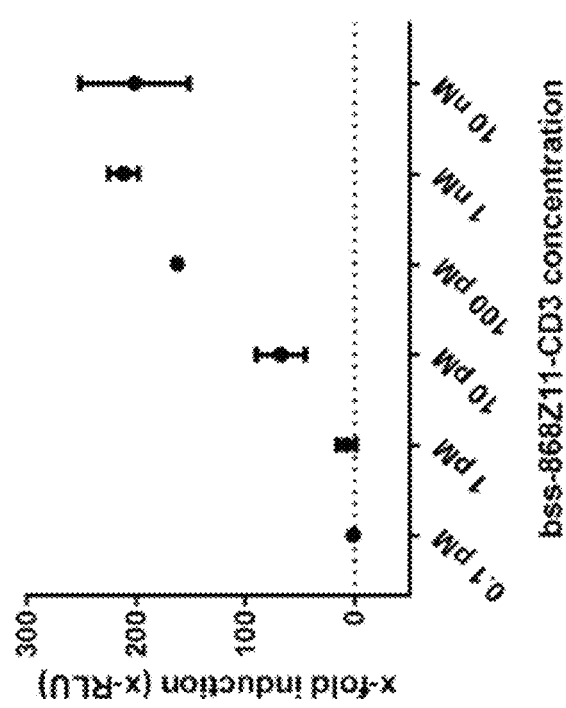
Figure 5C:
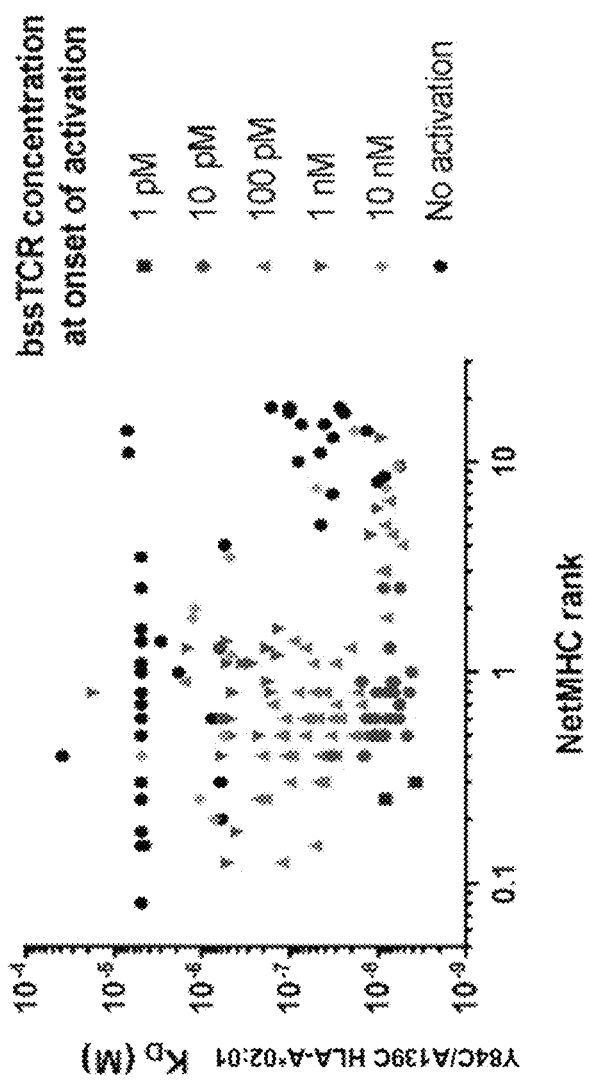
Figure 6A:
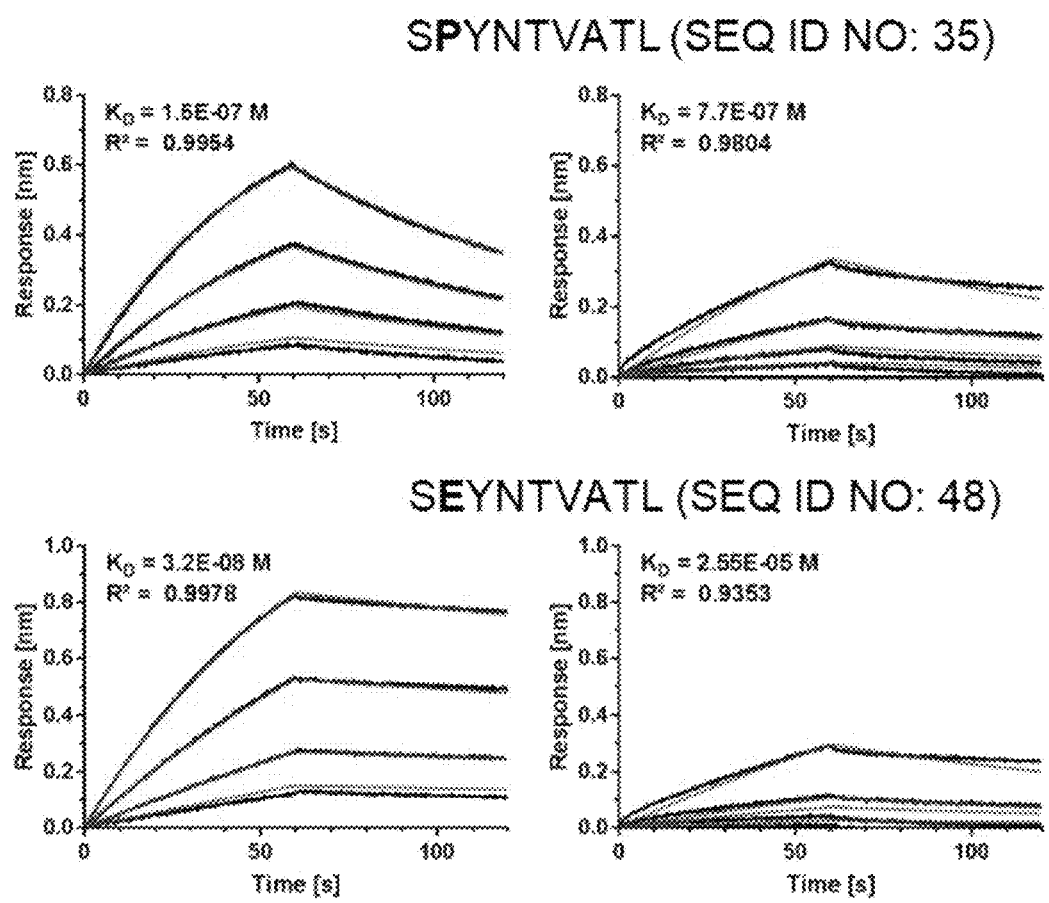
FIGS. 6A and 6B show the comparison of Y84C/A139C HLA-A*02:01 or UV exchange generated WT-A*02:01 pMHC complexes as soluble analytes for affinity measurements with immobilized bs-868Z11-CD3. Y84C/A139C HLA-A*02:01 complexes left, WT-A*02:01 complexes right. All measurements were performed using 1:2 analyte dilution series starting at 500 nM.
Figure 6B:
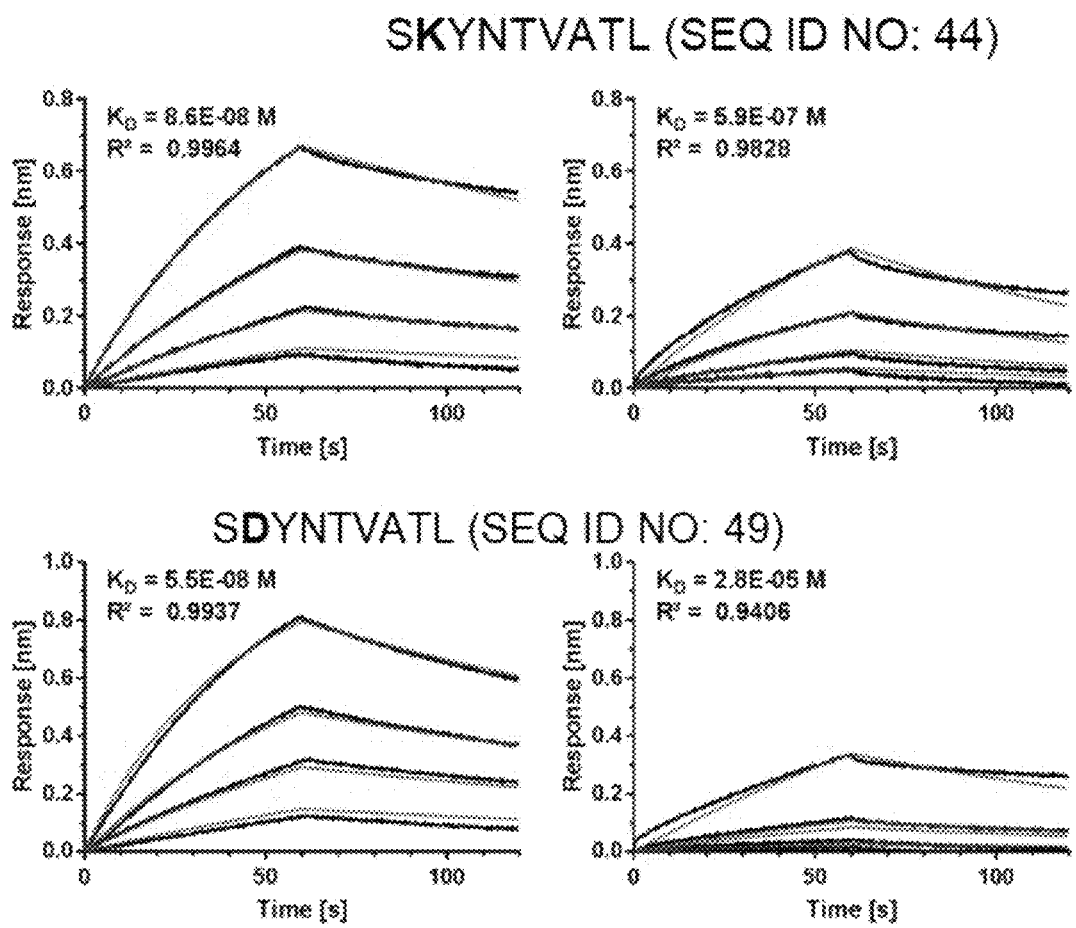

The pMHC-bsTCR binding affinity can be measured using this high-throughput screening platform, but should be consistent with the in vitro activity as functional T cell engaging bsTCR to be even more useful. Commonly, in vitro co-incubations of target and effector cells coupled with an appropriate readout are used to characterize these constructs. GloResponse™ NFAT-luc2 Jurkat effector cells, a cell line that expresses a luciferase reporter gene driven by a NFAT-response element, and peptide-loaded T2 target cells, a TAP-deficient A*02:01 cell line with restorable pMHC presentation through exogenous peptide loading, were incubated in the presence of bs-868Z11-CD3 to corroborate the significance of the kinetic screening in this context. T2 cells were loaded separately with respective peptides from the positional scanning library at a concentration of 100 nM and subsequently co-incubated with Jurkats and different bsTCR concentrations for 18 hours before readout. As expected the inventors encountered a broad spectrum of results, ranging from no detectable T cell activation at any bsTCR concentration to strong responses starting at low concentrations, e.g. for the wild type peptide (FIG. 5A). Since EC50 values could not be determined for many of the interactions in the selected bsTCR concentration range the inventors categorized the individual peptides by onset of T cell activation, defined as the lowest bsTCR concentration that was able to induce a 3-fold increased signal above. Onset values were plotted against the respectively measured Kos (FIG. 5B).

Overall, the inventors detected a good correlation between the determined $K_d$ values and T cell activation with one notable group of outliers with strong pMHC-bsTCR binding affinities but late T cell activation onset or no activation at all. The inventors were able to identify a direct connection between these peptides and their NetMHC predicted binding strength to the MHC (FIG. 5C) (26). This offered a potential explanation because different peptide binding affinities could result in different presentation levels of the respective pMHCs on the target cells after exogenous loading. These levels might, in turn, influence pMHC-bsTCR complex numbers and ultimately Jurkat effector (T cell) activation. To corroborate the hypothesis, the inventors performed a flow cytometric T2 peptide binding assay using an anti-HLA-A2 antibody and could detect less elevated HLA-A2 surface levels after peptide loading for peptides with lower binding affinities, especially NetMHC ranks of 2 and above, supporting the initial hypothesis. pMHC-bsTCR binding affinity correlated well with T cell activation onset for peptide ligands between NetMHC rank 0.05 and 2, whereas above that threshold T cell activation decreased with further increasing NetMHC ranks largely irrespective of pMHC-bsTCR binding affinity.

Figure 5E:
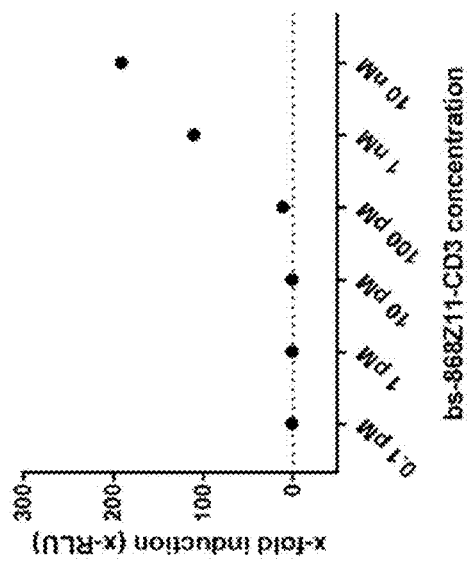
Figure 5D:
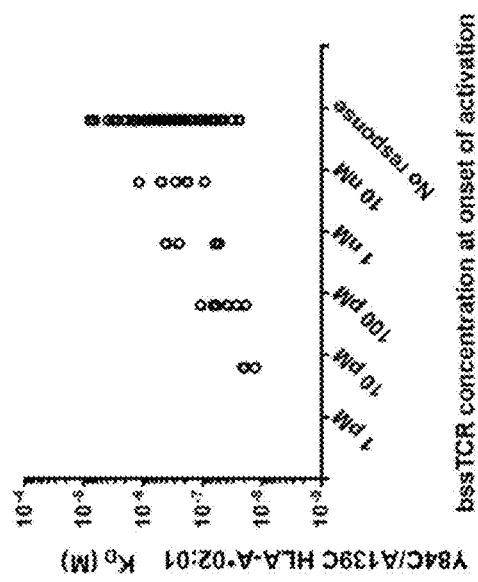

The inventors also performed T cell activation assays for the 140 peptide ligands selected by binding motif search, 24 were capable of inducing a 3-fold T cell activation over background with at least one of the supplied bsTCR concentrations (FIG. 5D). Measured $K_d$s correlated with the onset of T cell activation similarly to the results obtained by the positional scanning library. The previously highlighted IFFO1 antigen ALYNVLAKV (SEQ ID NO: 1) was also reactive in the reporter assay (FIG. 5E).

The inventors showed that pMHC-bsTCR binding affinity is a good indicator for the in vitro function of the scTv 868Z11 coupled with an anti-CD3 T cell engager. This highlights the value of the pMHC-bsTCR binding kinetics screening platform because it allows quick but adequate characterization of bsTCRs early in the development of such molecules.

23. Crystal Structure of the 1G4 Y84C/A139C HLA-A*02:01:01 ESO 9V TCR-pMHC

Figure 7A:
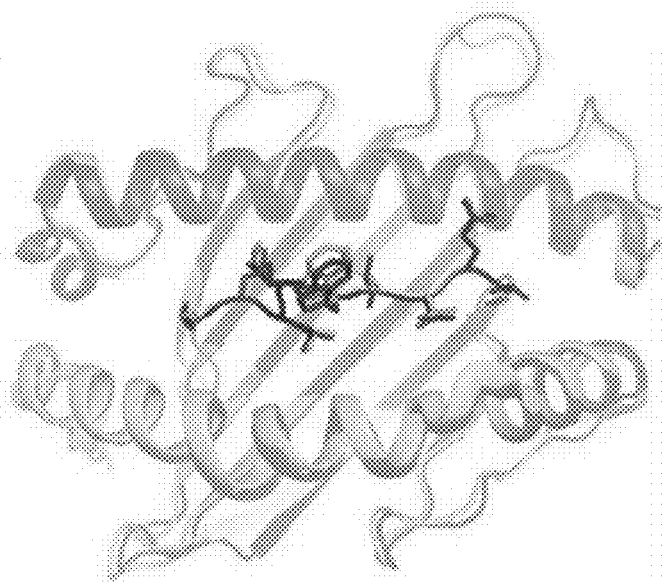
FIG. 7 shows the crystal structure of ESO 9V Y84C/A139C HLA-A*02:01 and ESO 9V WT-A*02:01 in complex with 1G4. (a) Overlay of WT and Y84C/A139C HLA-A*02:01 structure with a focus on peptide and amino acid side-chain orientation. (b) Close-up of the F-pocket and the introduced disulfide bond between α1 and α2. (c) Overlay of the 1G4 CDR loops interacting with the peptide and the MHC backbone. (d) Overlay of both crystal structures from a lateral perspective. Error bars represent biological triplicates.
Figure 7B:
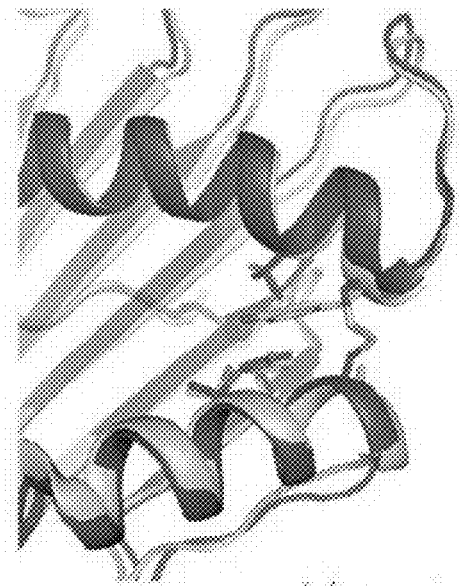
Figure 7C:
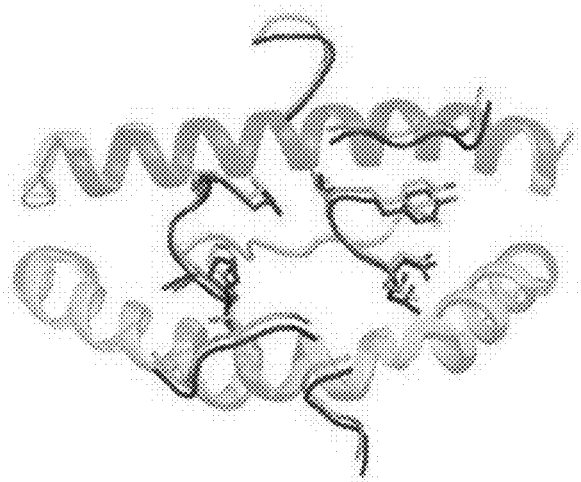
Figure 7D:
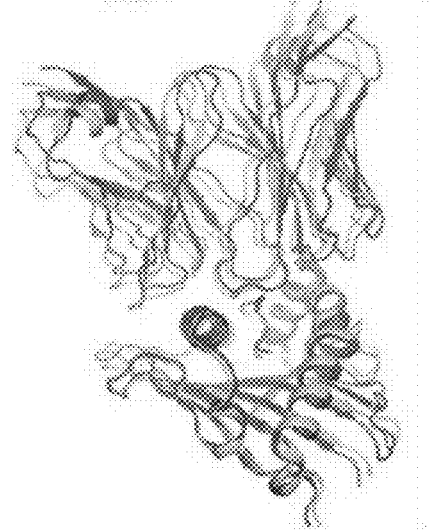

To further confirm that the 1G4 TCR recognizes ESO 9V Y84C/A139C HLA-A*02:01 indistinguishably from ESO 9V WT-A*02:01. TCR and disulfide-stabilized MHC refolded with ESO 9V were cocrystallized, as reported previously for the wild-type ESO 9V HLA-A*02:01 molecule and analyzed by x-ray crystallography (Table 2) (21). Comparison of the crystal structures revealed a high degree of structural overlap between both complexes. The backbone of both HLA-A*02:01 molecules aligned almost perfectly with a root mean square deviation (RMSD) value of 1.14 Å calculated over Cα (constant portion of the α chain of a T cell receptor; FIG. 7A). The same was true for both bound peptides including their side chains with an RMSD value of 1.27 Å calculated over all atoms, even when in close vicinity to the disulfide bond (FIG. 7B).

Similar conclusions could be made for the interaction with the 1G4 TCR. The complementarity-determining region (CDR) loop regions interacting with the peptide and the MHC backbone did show slight deviations of the interface and a small change in the docking angle of 4.13°, when comparing WT-A*02:01 1G4 with the Y84C/A139C HLA-A*02:01 1G4 crystal structure. This shift was still within the range of expected deviations for the same complex when crystallized repeatedly (FIGS. 7, C and D). Together, determined binding affinities and crystal structure showcase peptide receptiveness and similar properties of the Y84C/A139C HLA-A*02:01 pMHC complexes compared with wild-type complexes with respect to TCR binding. The crystal structure of the 1G4 Y84C/A139C HLA-A*02:01 ESO 9V complex has been deposited in the PDB under the accession number 6Q3S.

24. Discussion

Here, the inventors have presented disulfide-stabilized and functionally empty HLA-A*02:01 molecules, which can be refolded and purified without the use of typically required high-affinity peptides e.g. the dipeptide GM. The resulting monomers can form pMHCs after addition of peptides in a one-step loading procedure. Although the disulfide bridge enhances the stability of the MHC molecule, introduction does not inhibit or significantly alter binding of TCRs to disulfide-modified HLA*02:01 pMHC complexes compared with the wild type. This technique represents a great tool to quickly produce large pMHC libraries that are suitable for affinity measurements. Combining disulfide modified HLA*02:01-produced pMHC complex libraries with bio-layer interferometry-based analysis results in a platform capable of high-throughput pMHC-bsTCR binding kinetics screenings. This setup could also be useful for the analysis of other biologics targeting pMHC complexes, like monoclonal antibodies or bispecifics, such as bispecific T cell engagers. In one application of this platform, the inventors were able to quickly collect a pMHC-bsTCR binding affinity dataset for the HIV-specific bsTCR bs-868Z11-CD3. bsTCR binding affinities for respective pMHCs were indicative of in vitro activity when coupled with the presented T cell engager and tested in a cellular reporter assay, making these datasets valuable for bsTCR characterization. Analysis of the relationship between binding affinity and bsTCR-mediated cellular activation over a wide range of pMHC-bsTCR affinities has been difficult, thus far as a result of the limited tools available to feasibly collect such datasets.

The collected binding motif revealed similarities to the binding motif of the wild-type TCR 868. Analysis of an 868-SV9 crystal structure, as well as an accompanying alanine scan by Cole et al. (34), revealed prominent interactions between the CDR3a region and the amino acids 4N and 5T of SLYNTVATL (SEQ ID NO: 5). This behavior seems to be conserved although a significant part of the CDR3a is mutated in the 868Z11 construct. Using the binding motif and a model search strategy, the inventors were able to identify multiple peptides from the human proteome, which demonstrated high-affinity interactions with the bsTCR and the potential to induce bsTCR-mediated Jurkat effector activation when presented on target cells.

Note that TCR binding motifs derived from single amino acid substitution libraries may still not reflect all possible peptides a specific TCR (sTCR) can recognize, because the exchange of multiple amino acids, at the same time, might have different effects than the isolated exchanges. Alternative approaches include screening of more complex libraries, for example, through target cell loading with high diversity peptide pools, each randomized at all but one position of the peptide, or screenings against randomized peptide libraries presented as pMHC complexes on yeast surfaces (10, 32, 33). Further research directly comparing these approaches will be necessary to gain a deeper understanding of the respective strengths and weaknesses. Ultimately, safety screenings of clinical candidates should always be composed of multiple approaches, for example, by combining binding motif guided analysis together with cellular screenings of large panels of healthy tissue-derived cell lines, to minimizing risks. The results presented herein highlight the capability of this approach to identifying potentially relevant off-target interactions in combination with the pMHC-bsTCR binding kinetics screening platform. Because it offers quick analysis of complex pMHC libraries, it can be used early in the development process to select promising candidates and thus, complements established methods. This platform can also facilitate larger and more comprehensive screenings of late-stage candidates, potentially against mass spectrometry data-driven tissue-specific pMHC libraries covering the known immunopeptidome. Because of its stability and low-effort peptide loading procedure, the disulfide-modified HLA*02:01 molecules could potentially enable even higher-throughput platforms. Thanks to these properties, it could be perfectly suited for the creation of high complexity pMHC microarrays with thousands of different pMHC complexes, for example, by combining large-scale coating of disulfide-modified HLA*02:01 molecules and modern high-throughput peptide microarray inkjet printers.

REFERENCES AS CITED

1. Rammensee, H. G., Falk, K. & Rötzschke, O. Peptides naturally presented by MHC class I molecules. *Annu. Rev. Immunol.* 11, 213-44 (1993).
2. Garboczi, D. N. et al. HLA-A2-peptide complexes: refolding and crystallization of molecules expressed in *Escherichia coli* and complexed with single antigenic peptides. *Proc. Natl. Acad. Sci. U.S.A* 89, 3429-3433 (1992).
3. Altman, J. D. et al. Phenotypic analysis of antigen-specific T lymphocytes. *Science (80-.).* 274, 94-96 (1996).
4. Hadrup, S. R. et al. High-throughput T-cell epitope discovery through MHC peptide exchange. *Methods Mol. Biol.* 524, 383-405 (2009).
5. Garcia, K. C. et al. Alphabeta T cell receptor interactions with syngeneic and allogeneic ligands: affinity measurements and crystallization. *Proc. Natl. Acad. Sci. U.S.A.* 94, 13838-43 (1997).
6. Stone, J. D. & Kranz, D. M. Role of T Cell Receptor Affinity in the Efficacy and Specificity of Adoptive T Cell Therapies. *Front. Immunol.* 4, 1-16 (2013).
7. Robbins, P. F. et al. Single and dual amino acid substitutions in TCR CDRs can enhance antigen-specific T cell functions. *J. Immunol.* 180, 6116-6131 (2008).
8. Varela-Rohena, A. et al. Control of HIV-1 immune escape by CD8 T cells expressing enhanced T-cell receptor. *Nat. Med.* 14, 1390-1395 (2008).
9. Oates, J., Hassan, N. J. & Jakobsen, B. K. ImmTACs for targeted cancer therapy: Why, what, how, and which. *Mol. Immunol.* 67, 67-74 (2015).
10. Wooldridge, L. et al. A single autoimmune T cell receptor recognizes more than a million different peptides. *J. Biol. Chem.* 287, 1168-1177 (2012).
11. Cameron, B. J. et al. Identification of a Titin-derived HLA-A1-presented peptide as a cross-reactive target for engineered MAGE A3-directed T cells. *Sci. Trans. Med.* 5, 197ra103 (2013).
12. Linette, G. P. et al. Cardiovascular toxicity and titin cross-reactivity of affinity-enhanced T cells in myeloma and melanoma. *Blood* 122, 863-871 (2013).
13. Raman, M. C. C. et al. Direct molecular mimicry enables off-target cardiovascular toxicity by an enhanced affinity TCR designed for cancer immunotherapy. *Sci. Rep.* 6, 18851 (2016).
14. Bijen, H. M. et al. Preclinical Strategies to Identify Off-Target Toxicity of High-Affinity TCRs. *Mol. Ther.* (2018). doi:10.1016/J.YMTHE.2018.02.017
15. Shao, W. et al. The SysteMHC Atlas project. *Nucleic Acids Res.* 46, D1237-D1247 (2018).
16. Zacharias, M. & Springer, S. Conformational Flexibility of the MHC Class I α1-α2 Domain in Peptide Bound and Free States: A Molecular Dynamics Simulation Study. *Biophys. J.* 87, 2203-2214 (2004).
17. Hein, Z. et al. Peptide-independent stabilization of MHC class I molecules breaches cellular quality control. *J. Cell Sci.* 127, 2885-97 (2014).
18. Saini, S. K. et al. Not all empty MHC class I molecules are molten globules: Tryptophan fluorescence reveals a two-step mechanism of thermal denaturation. *Mol. Immunol.* 54, 386-396 (2013).
19. Saini, S. K. et al. Dipeptides promote folding and peptide binding of MHC class I molecules. *Proc. Natl. Acad. Sci.* 110, 15383-15388 (2013).
20. Boulter, J. M. et al. Stable, soluble T-cell receptor molecules for crystallization and therapeutics. *Protein Eng.* 16, 707-711 (2003).
21. Chen, J.-L. et al. Structural and kinetic basis for heightened immunogenicity of T cell vaccines. *J. Exp. Med.* 201, 1243-55 (2005).
22. Aggen, D. H. et al. Identification and engineering of human variable regions that allow expression of stable single-chain T cell receptors. *Protein Eng. Des. Sel.* 24, 361-372 (2011).
23. Zhu, Z. & Carter, P. Identification of heavy chain residues in a humanized anti-CD3 antibody important for efficient antigen binding and T cell activation. *J. Immunol.* 155, 1903-10 (1995).
24. Burrows, S. R., Rodda, S. J., Suhrbier, A., Geysen, H. M. & Moss, D. J. The specificity of recognition of a cytotoxic T lymphocyte epitope. *Eur. J. Immunol.* 22, 191-195 (1992).
25. Rodenko, B. et al. Generation of peptide-MHC class I complexes through UV-mediated ligand exchange. *Nat. Protoc.* 1, 1120-1132 (2006).
26. Andreatta, M. & Nielsen, M. Gapped sequence alignment using artificial neural networks: application to the MHC class I system. *Bioinformatics* 32, 511-517 (2016).
27. Thomsen, M. C. F. & Nielsen, M. Seq2Logo: a method for construction and visualization of amino acid binding motifs and sequence profiles including sequence weighting, pseudo counts and two-sided representation of amino acid enrichment and depletion. *Nucleic Acids Res.* 40, W281-7 (2012).
28. Weinschenk, T. et al. Integrated functional genomics approach for the design of patient-individual antitumor vaccines. *Clin. Cancer Res.* 62, 5818-5827 (2002).
29. Fritsche, J. et al. Translating Immunopeptidomics to Immunotherapy-Decision-Making for Patient and Personalized Target Selection. *Proteomics* 18, 1700284 (2018).
30. Elliott, T., Willis, A., Cerundolo, V. & Townsend, A. Processing of major histocompatibility class I-restricted antigens in the endoplasmic reticulum. *J. Exp. Med.* 181, 1481-1491 (1995).
31. Bossi, G. et al. Examining the presentation of tumor-associated antigens on peptide-pulsed T2 cells. *Oncoimmunology* 2, e26840 (2013).
32. Birnbaum, M. E. et al. Deconstructing the peptide-MHC specificity of t cell recognition. *Cell* 157, 1073-1087 (2014).
33. Gee, M. H. et al. Antigen Identification for Orphan T Cell Receptors Expressed on Tumor-Infiltrating Lymphocytes. *Cell* 172, 549-563.e16 (2018).
34. Cole, D. K. et al. Dual molecular mechanisms govern escape at immunodominant HLA A2-restricted HIV epitope. *Front. Immunol.* 8, 1503 (2017).
35. Kabsch, W. XDS. *Acta Crystallogr. D Biol. Crystalogr.* 66, 125-132 (2010).
36. Evans, P. Scaling and assessment of data quality. *Acta Crystallogr. Sect. D Biol. Crystallogr.* 62, 72-82 (2006).

37. Vagin, A. et al. Molecular replacement with MOLREP. *Acta Crystollogr. Sect. D Biol. Crystallogr.* 66, 22-25 (2010).
38. Kovalevskiy, O. et al. Overview of refinement procedures within REFMAC 5: Utilizing data from different sources. *Acta Crystallogr. Sect. D Struct. Biol.* 74, 215-227 (2018).
39. Emsley, P. et al. Features and development of Coot. *Acta Crystallogr. Sect. D Biol. Crystallogr.* 66, 486-501 (2010).
40. Chen, V. B. et al. MolProbity: All-atom structure validation for macromolecular crystallography. *Acta Crystallogr. Sect. D Biol. Crystallogr.* 66, 12-21 (2010).
41. S. K. Saini, T. Tamhane, R. Anjanappa, A. Saikia, S. Ramskov, M. Donia, I. M. Svane, S. N. Jakobsen, M. Garcia-Alai, M. Zacharias, R. Meijers, S. Springer, S. R. Hadrup, Empty peptide-receptive MHC class I molecules for efficient detection of antigen-specific T cells. *Sci. Immunol.* 4, 37 eaau9039, 07-19 (2019).

The invention claimed is:

1. A polypeptide comprising a stabilized human HLA-A*0201 molecule capable of binding to a peptide ligand,
wherein said HLA-A molecule comprises an artificially introduced covalent bridge between a first amino acid within the β1 unit at the amino acid position 22 in the alpha 1 domain and a second amino acid within the α1 unit at the amino acid position 71 in the alpha 1 domain of the HLA-A molecule based on IGMT numbering excluding the first 24 amino acids,
wherein the first and the second amino acids are each modified to a cysteine forming a first disulfide bridge,
wherein the first amino acid at position 22 is modified from phenylalanine (F) to cysteine (C) and the second amino acid at position 71 is modified from serine (S) to cysteine (C), and
wherein the first disulfide bridge stabilizes the HLA-A molecule in the absence of the peptide ligand.

2. A pharmaceutical composition comprising the polypeptide of claim 1
wherein said stabilized HLA-A molecule is bound to a bead, filament, nanoparticle or other suitable carrier, and
wherein the composition is produced by contacting the peptide ligand with the stabilized HLA-A molecule and forming a peptide ligand-loaded HLA-A molecule thereby.

3. The pharmaceutical composition according to claim 2, further comprising an anti-CD28 antibody or an anti-4-1BB antibody.

4. A vaccine comprising the pharmaceutical composition according to claim 2.

5. The polypeptide according to claim 1, wherein the HLA-A molecule further comprises a third amino acid modified in the α1 unit of the alpha 1 domain at the amino acid position 51 and a fourth amino acid modified within the alpha 2 domain at the amino acid position 175 based on IGMT numbering excluding the first 24 amino acids, wherein the third and the fourth amino acids are each modified to a cysteine forming a second disulfide bridge.

6. The pharmaceutical composition according to claim 3, wherein the composition comprises the anti-CD28 antibody.

7. The pharmaceutical composition according to claim 3, wherein the composition comprises the anti-4-1BB antibody.

8. The polypeptide of claim 1, comprising SEQ ID NO: 324.

9. The polypeptide of claim 5, wherein the polypeptide comprises SEQ ID NO: 325.

10. A pharmaceutical composition comprising the polypeptide of claim 5,
wherein the stabilized HLA-A molecule is bound to a bead, filament, nanoparticle or other suitable carrier, and
wherein the composition is produced by contacting the peptide ligand with the stabilized HLA-A molecule and forming a peptide ligand-loaded HLA-A molecule thereby.

11. The pharmaceutical composition of claim 10, further comprising an anti-CD28 antibody or an anti-4-1BB antibody.

* * * * *